(12) United States Patent
Jaffrey et al.

(10) Patent No.: US 10,316,000 B2
(45) Date of Patent: Jun. 11, 2019

(54) COUPLED RECOGNITION/DETECTION SYSTEM FOR IN VIVO AND IN VITRO USE

(75) Inventors: Samie R. Jaffrey, New York, NY (US); Jeremy S. Paige, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/202,250

(22) PCT Filed: Feb. 18, 2010

(86) PCT No.: PCT/US2010/024622
§ 371 (c)(1),
(2), (4) Date: Jun. 11, 2012

(87) PCT Pub. No.: WO2010/096584
PCT Pub. Date: Aug. 26, 2010

(65) Prior Publication Data
US 2012/0252699 A1 Oct. 4, 2012

Related U.S. Application Data

(60) Provisional application No. 61/207,897, filed on Feb. 18, 2009.

(51) Int. Cl.
*G01N 21/64* (2006.01)
*C12N 15/63* (2006.01)
(Continued)

(52) U.S. Cl.
CPC ........ *C07D 233/96* (2013.01); *A61K 49/0032* (2013.01); *A61K 49/0054* (2013.01); *C07D 403/06* (2013.01); *C09B 23/04* (2013.01)

(58) Field of Classification Search
CPC ................................. G01N 21/64; C40B 40/06
(Continued)

(56) References Cited

U.S. PATENT DOCUMENTS 6,458,559 B1 10/2002 Shi et al.
7,125,660 B2 10/2006 Stanton et al.
(Continued)

FOREIGN PATENT DOCUMENTS

EP 0422900 A2 10/1990
FR 2919608 A1 1/2007
(Continued)

OTHER PUBLICATIONS

Bellobono et al., Kinetics of Base-catalysed Condensation of 5-Methylfuran-2(3H)-one with 2-Hydroxybenzaldehyde, J. Chem. Soc. Perkin Trans. Phys. Org. Chem., 1975, 15, 1773-1776.*
(Continued)

*Primary Examiner* — Amy M Bunker
(74) *Attorney, Agent, or Firm* — Pepper Hamilton LLP

(57) ABSTRACT

The present invention relates to novel fluorophores and their use in combination with novel nucleic acid molecules, called aptamers, that bind specifically to the fluorophore and thereby enhance the fluorescence signal of the fluorophore upon exposure to radiation of suitable wavelength. Molecular complexes formed between the novel fluorophores, novel nucleic acid molecules, and their target molecules are described, and the use of multivalent aptamer constructs as fluorescent sensors for target molecules of interest are also described.

11 Claims, 24 Drawing Sheets

Specification includes a Sequence Listing.

RNA switches on fluorophore *only* in the presence of target X

(51) Int. Cl.
*C40B 60/00* (2006.01)
*C07D 233/96* (2006.01)
*A61K 49/00* (2006.01)
*C07D 403/06* (2006.01)
*C09B 23/04* (2006.01)

(58) Field of Classification Search
USPC ...................................................... 506/9, 16
See application file for complete search history.

(56) References Cited

U.S. PATENT DOCUMENTS

| | | | |
|---|---|---|---|
| 2002/0111358 A1 | 8/2002 | Nishiyama et al. | |
| 2003/0211516 A1 | 11/2003 | Davis | |
| 2004/0138227 A1* | 7/2004 | Nishiyama et al. | 514/253.05 |
| 2006/0172320 A1 | 8/2006 | Stojanovic | |

FOREIGN PATENT DOCUMENTS

| | | |
|---|---|---|
| JP | 2006-178325 | 7/2006 |
| WO | 2007147159 A2 | 12/2007 |
| WO | WO 2007147159 A2 * | 12/2007 |

OTHER PUBLICATIONS

Bourotte et al., Fluorophores Related to the Green Fluorescent Protein, Tetrahedron Letters, 2004, 45, 6343-6348.*
Szent-Gyorgyi et al., Fluorogen-Activating Single-Chain Antibodies for Imaging Cell Surface Proteins, Nature Biotechnology, 2008, 26(2), 235-240.*
Babendure et al., Aptamers Switch on Fluorescence of Triphenylmethane Dyes, Journal of the American Chemical Society, 2003, 14716-14717.*
Pakhomov et al., GFP Family: Structural Insights into Spectral Tuning, Chemistry & Biology Review, 2008, 755-764.*
Zhang et al., Reviews, Creating New Fluorescent Probes for Cell Biology, Nature, 2002, 3, 906-918.*
Shaner et al., Advances in Fluorescent Protein Technology, Journal of Cell Science, 2007, 120, 4247-4260.*
Fischer et al., Massively Parallel Interrogation of Aptamer Sequence, Structure and Function, PLoS One, 2008, 3(7), 1-9.*
Ajmera et al. "Cns-Depressant and Anticonvulsant Activities of 1-Substituted Phenyl (Aryl)-2-Methyl-4 (3,4,5, Trimethoxybenzylidene)-5-Imidazolones," Drugs Expt Clin Res 6(3):171-176 (1980).
Nichols et al. "Serotoin Receptors," Chem Rev 108:1614-1641 (2008).
Bourotte et al. "Fluorophores Related to the Green Fluorescent Protein," Tetrahedron Letters 45:343-6348 (2004).
He et al. "Synthesis and Spectroscopic Studies of Model Red Fluorescent Protein Chromophores," Organic Letters 4 (9):1523-1526 (2002).
You et al. "Fluorophores Related to the Green Fluorescent Protein and Their Use in Optoelectronic Devices," Advanced Materials 12(22):1678-1681 (2000).
Badr et al. "Synthesis of 1,2-Disubstituted 4-Benzylidene-2-Innidazolin-5-ones and their Thione Derivatives," Indian Jour of Chem 18B(3):240-242 (1979) (Abstract only).
Grate et al. "Laser-mediated, Site-specific Inactivation of RNA Transcripts," Proc Natl Acad Sci USA 96:6131-6136 (1999).
Lerestif et al. "Cycloaddition with Stabilized Imidates as Potential Azomethines Ylides : A New Route to 2-Imidazoline and 4-Yliden-5-Imidazolinone," Tetrahedron Letters 34(29):4639-4642 (1993).
Stanlis et al., "Single-strand DNA Aptamers as Probes for Protein Localization in Cells," J. Histochem Cytochem. 51(6):797-808 (2003).
Stojanovic et al., "Modular Aptameric Sensors," JACS 126:9266-9270 (2004).
PCT International Search Report and Written Opinion for PCT/US10/24622, both dated Jul. 30, 2010.
Supplementary International Search Report and Written Opinion dated Dec. 5, 2012, for EP Patent Application No. 10744308.7.
Yarmoluk et al., "Interaction of Cyanine Dyes with Nucleic Acids—XXVII: Synthesis and Spectral Properties of Novel Homodi- and Homotrimeric Monomethine Cyanine Dyes," Dyes and Pigments 50:21-28 (2001).
Dong et al., "Isomerization in Fluorescent Protein Chromophores Involves Addition/Elimination," J. Am. Chem. Soc. 130:14096-14098 (2008).
Lotfy Aly et al., "Intercalating Nucleic Acids with Insertion of 5-[(Pyren-1-yl)methylidene]hydantoin-Substituted Butane-1,2-diol," Helvetica Chimica Acta 88:3137-3144 (2005).
Narang et al., "CXXXV.—Studies in Chemotherapy (Antimalarials). Part I. A Derivative of Glyoxalinoquinoline," J. Chem. Soc. p. 976 (Jan. 1, 1931).
Petersen et al., "Synthesis and Characterization of Model Compounds for the Neutral Green Fluorescent Protein Chromophore," Synthesis 23:3635-3638 (2007).
Socher et al., "FIT Probes: Peptide Nucleic Acid Probes with a Fluorescent Base Surrogate Enable Real-Time DNA Quantification and Single Nucleotide Polymorphism Discovery," Analyt. Biochem. 375:318-330 (2008).
Stafforst et al., "Synthesis of Alaninyl and N-(2-Aminoethyl)glycinyl Amino Acid Derivatives Containing the Green Fluorescent Protein Chromophore in their Side Chains for Incorporation into Peptides and Peptide Nucleic Acids," Eur. J. Org. Chem. 899-911 (2007).

* cited by examiner

A
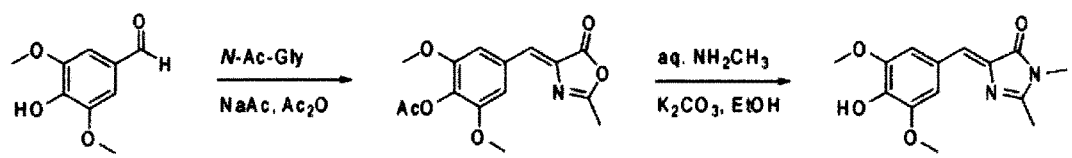
B
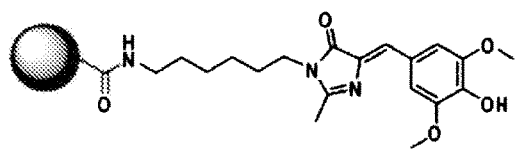
C
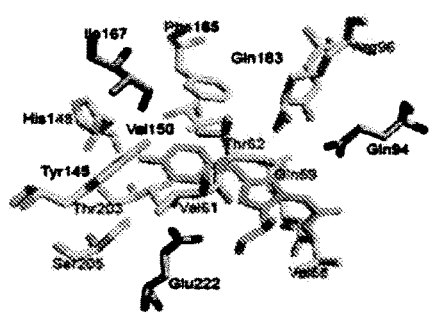
Figures 1A-C

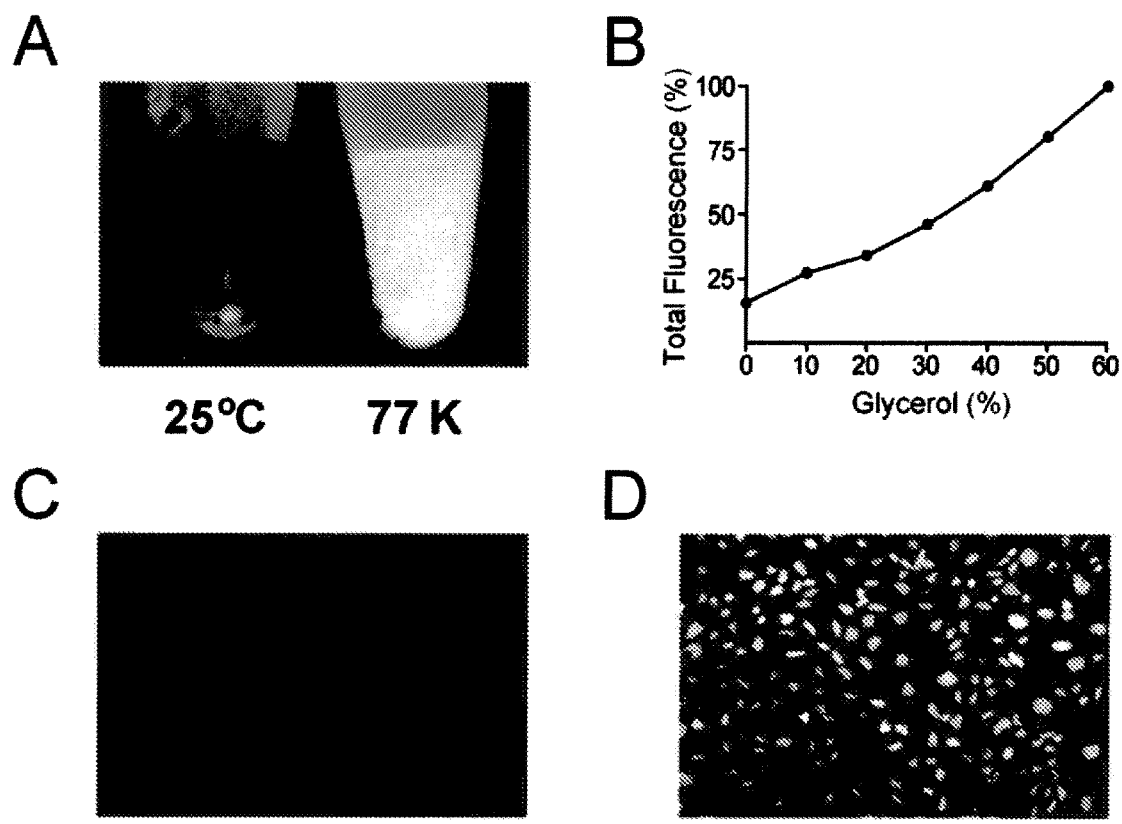
Figures 2A-D

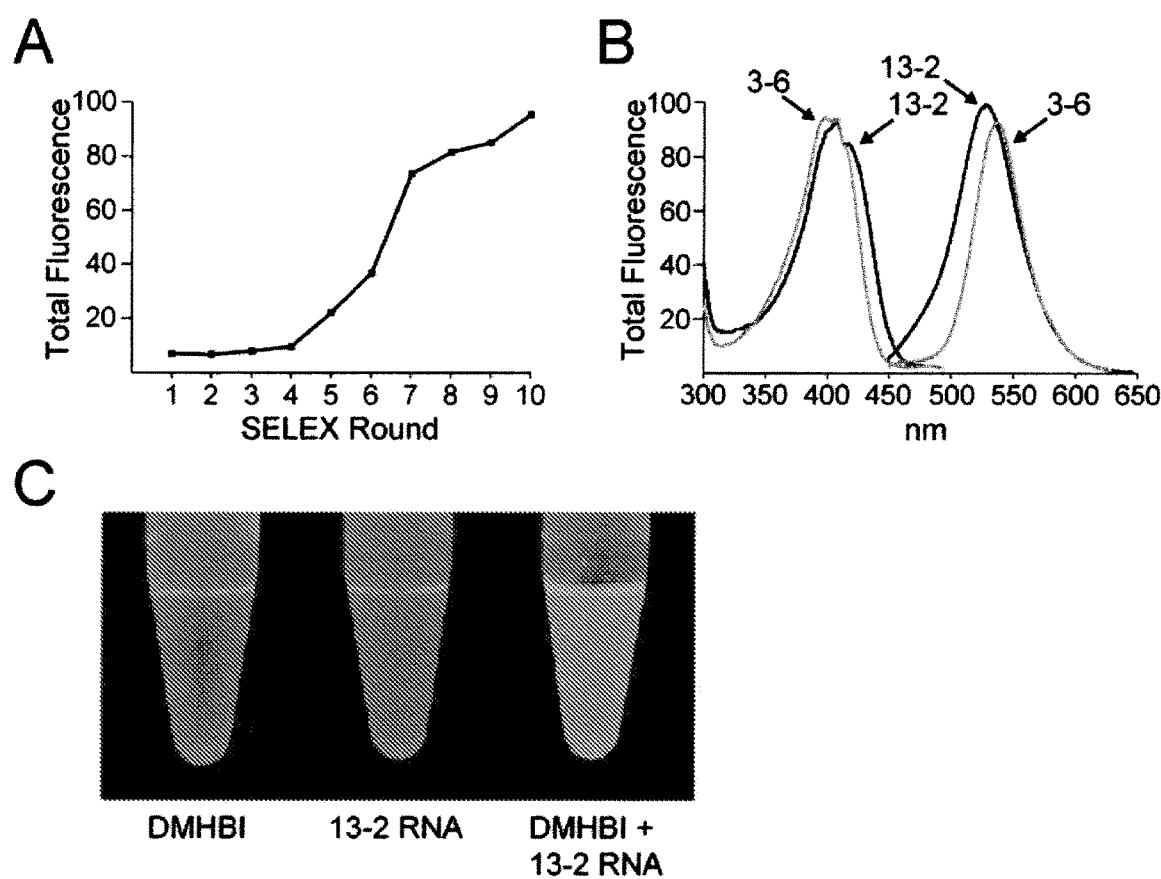
Figures 3A-C

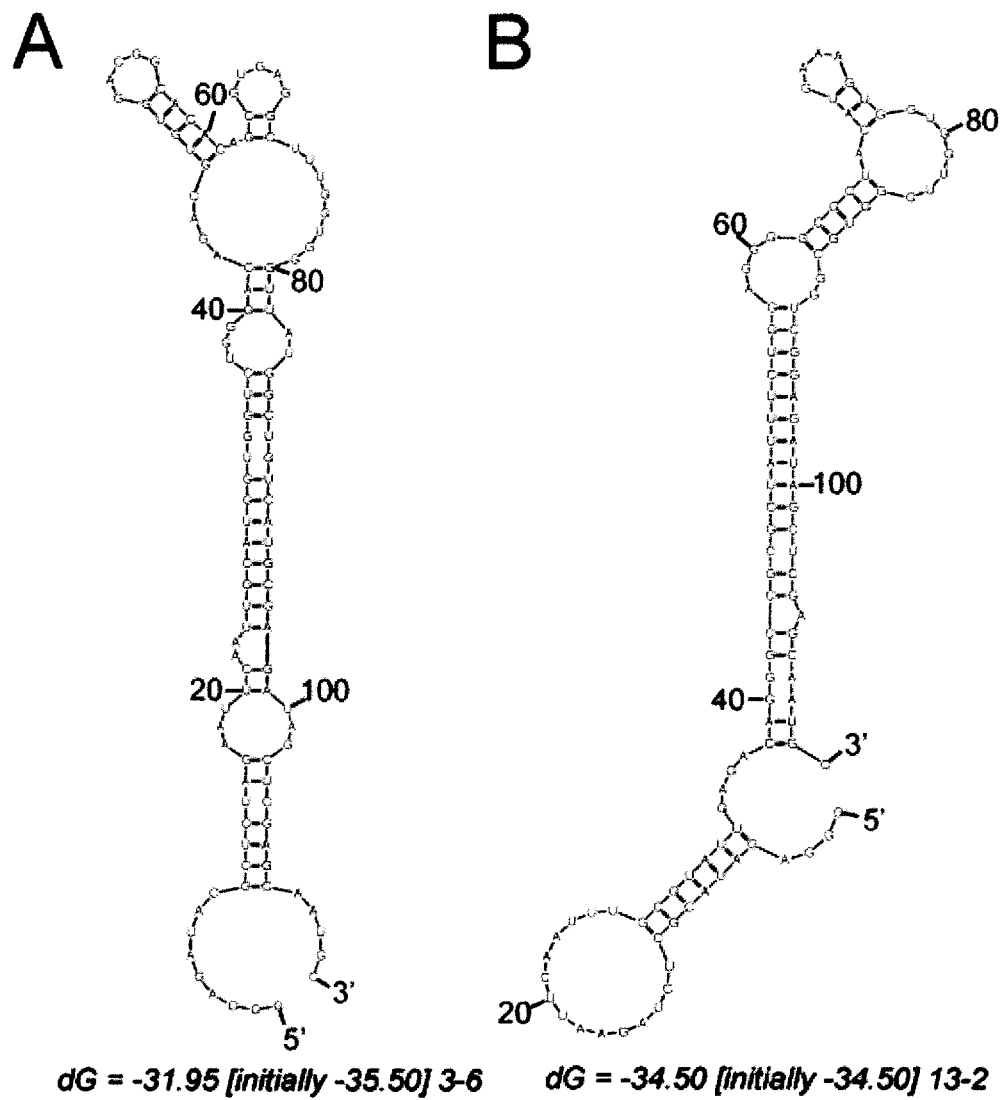
Figures 4A-B

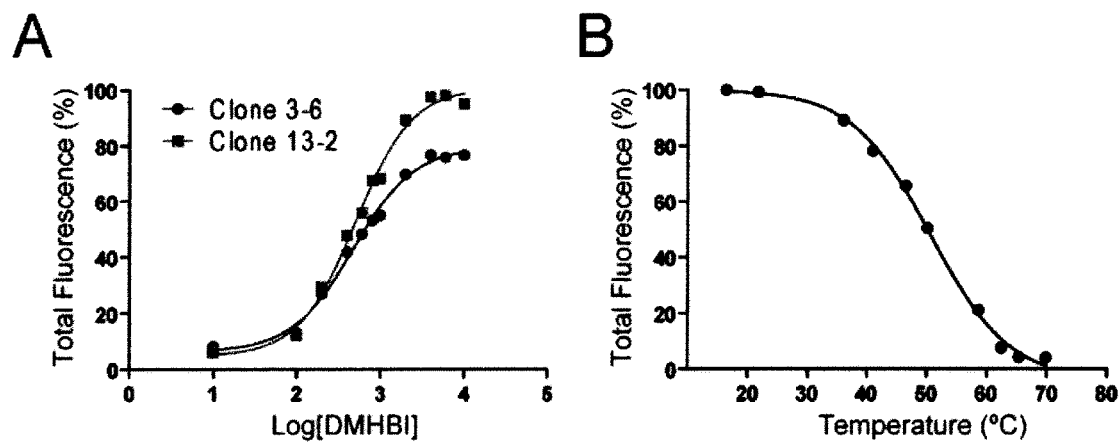
Figures 5A-B
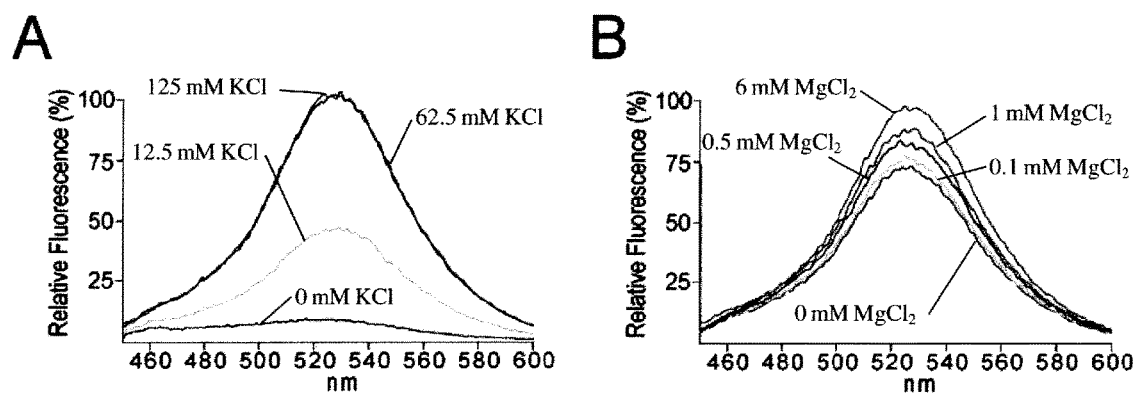
Figures 6A-B dG = -22.30 [initially -22.30] 13-2-min

Figures 9A-C dG = -24.90 [initially -24.90] 13-2-5-min

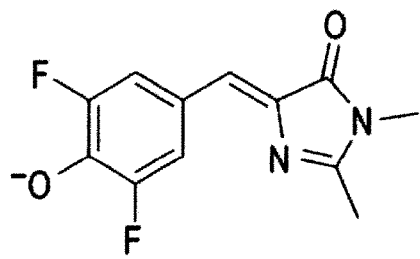 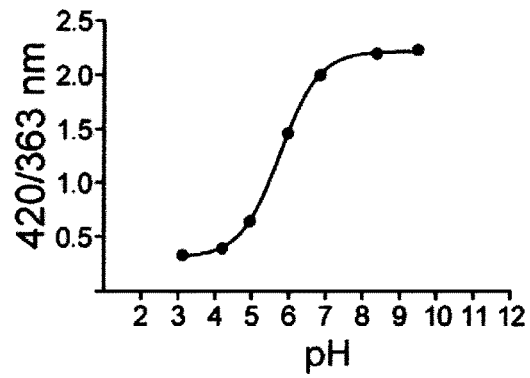
Figures 11A-B
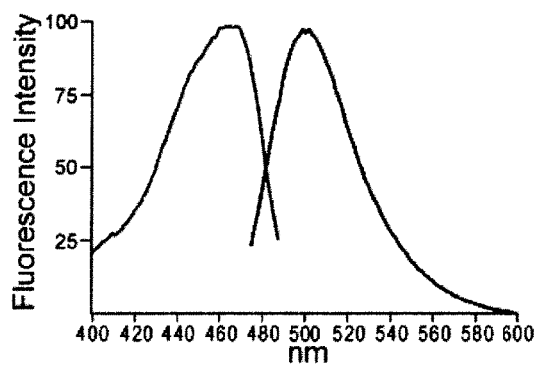 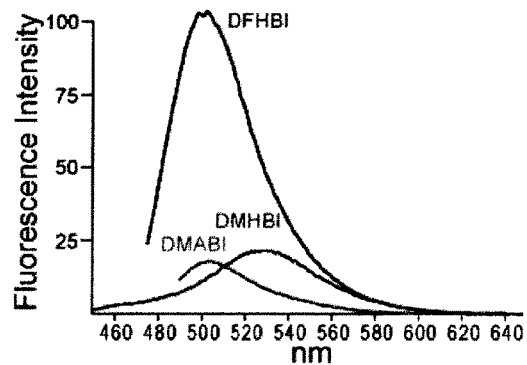
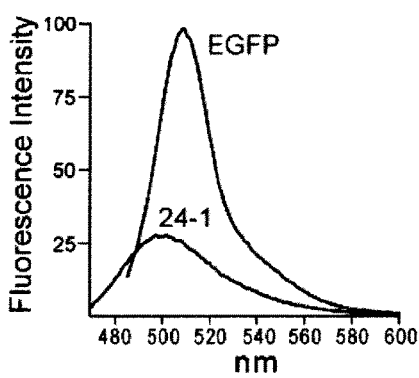 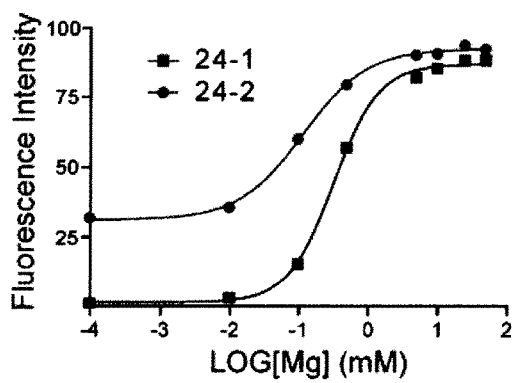
Figures 12A-D

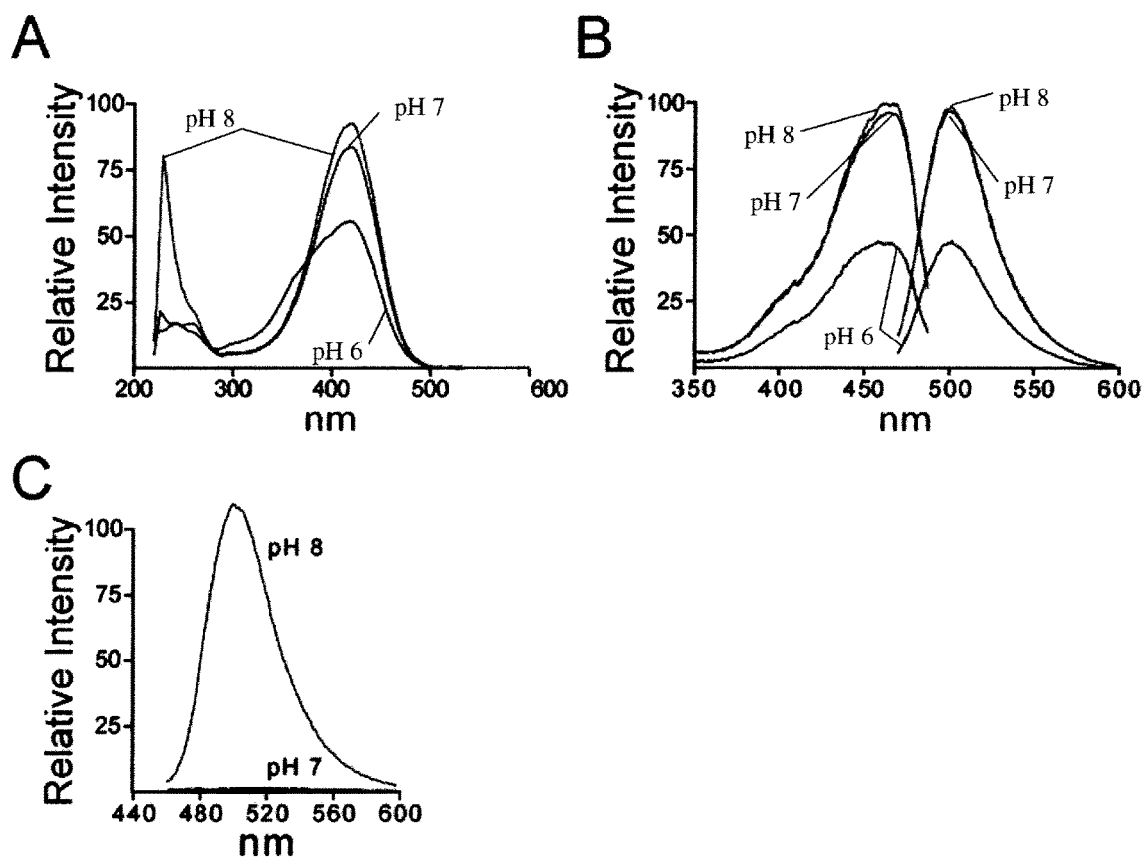
Figures 13A-C

A
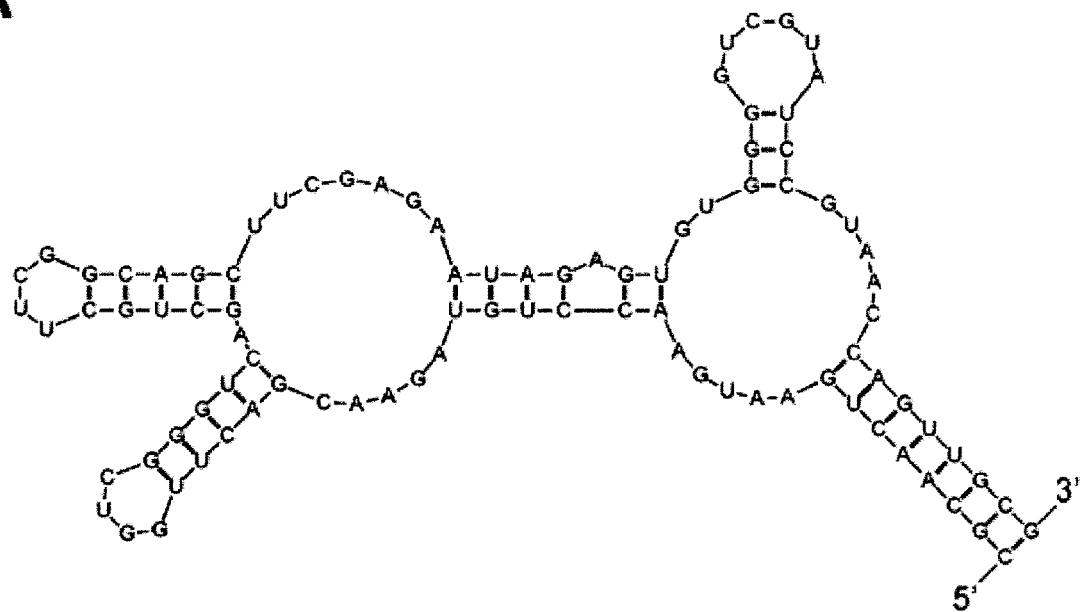
B
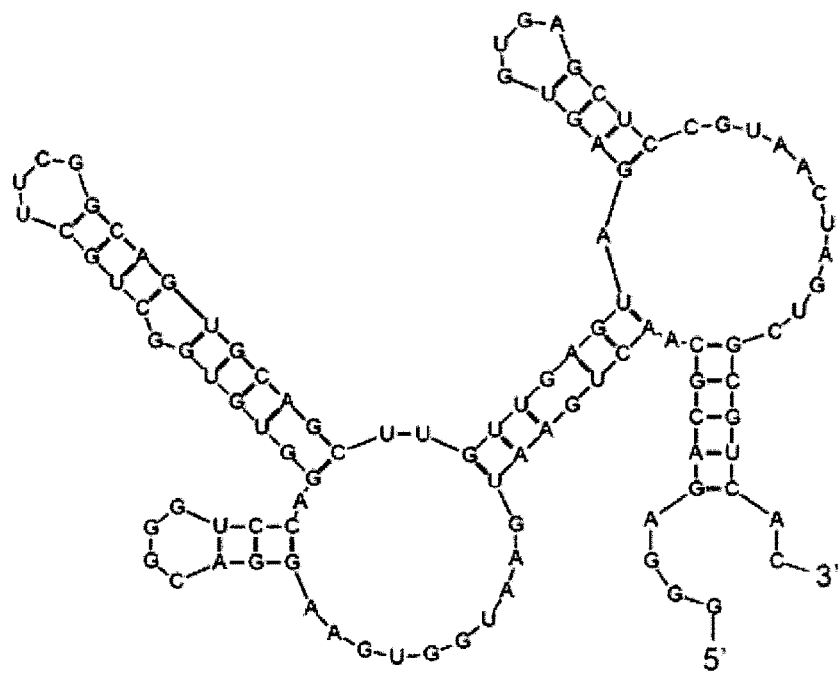
Figures 14A-B

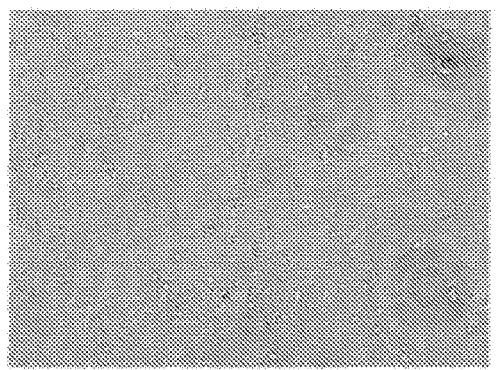 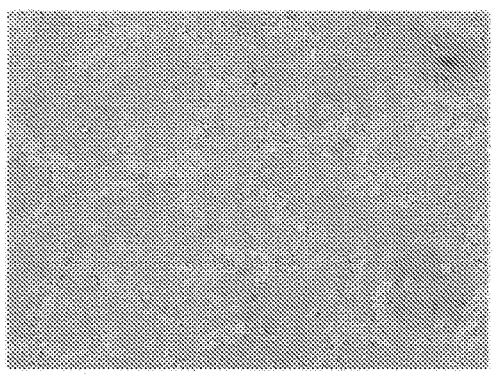
Figures 15A-B

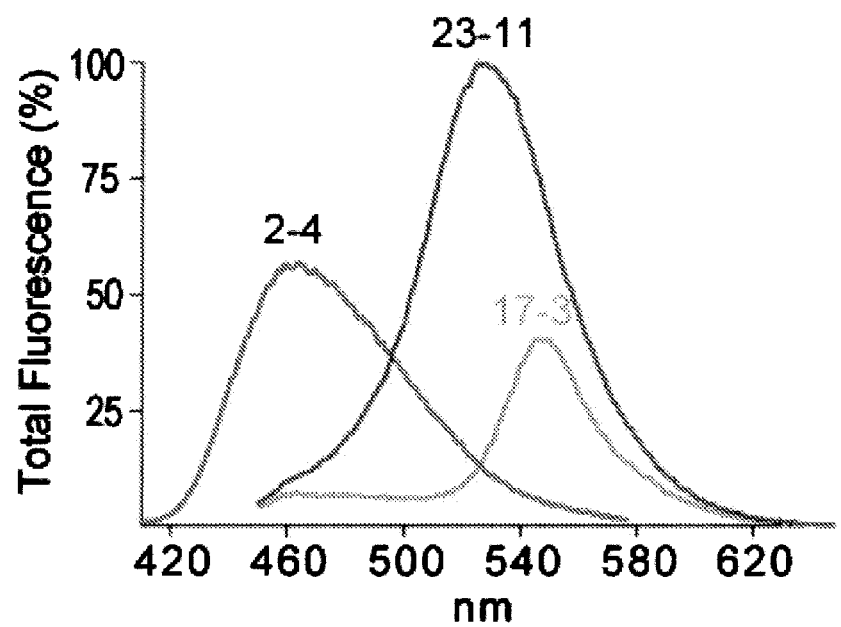
Figure 16
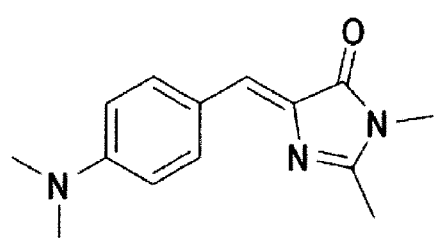 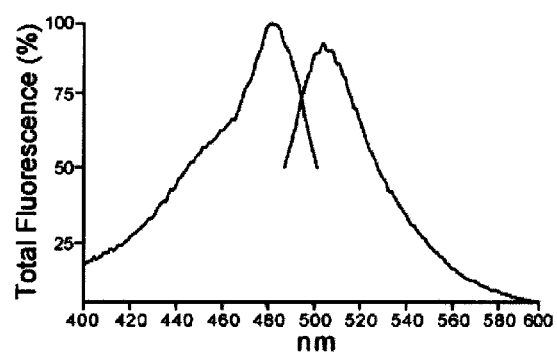
Figures 17A-B

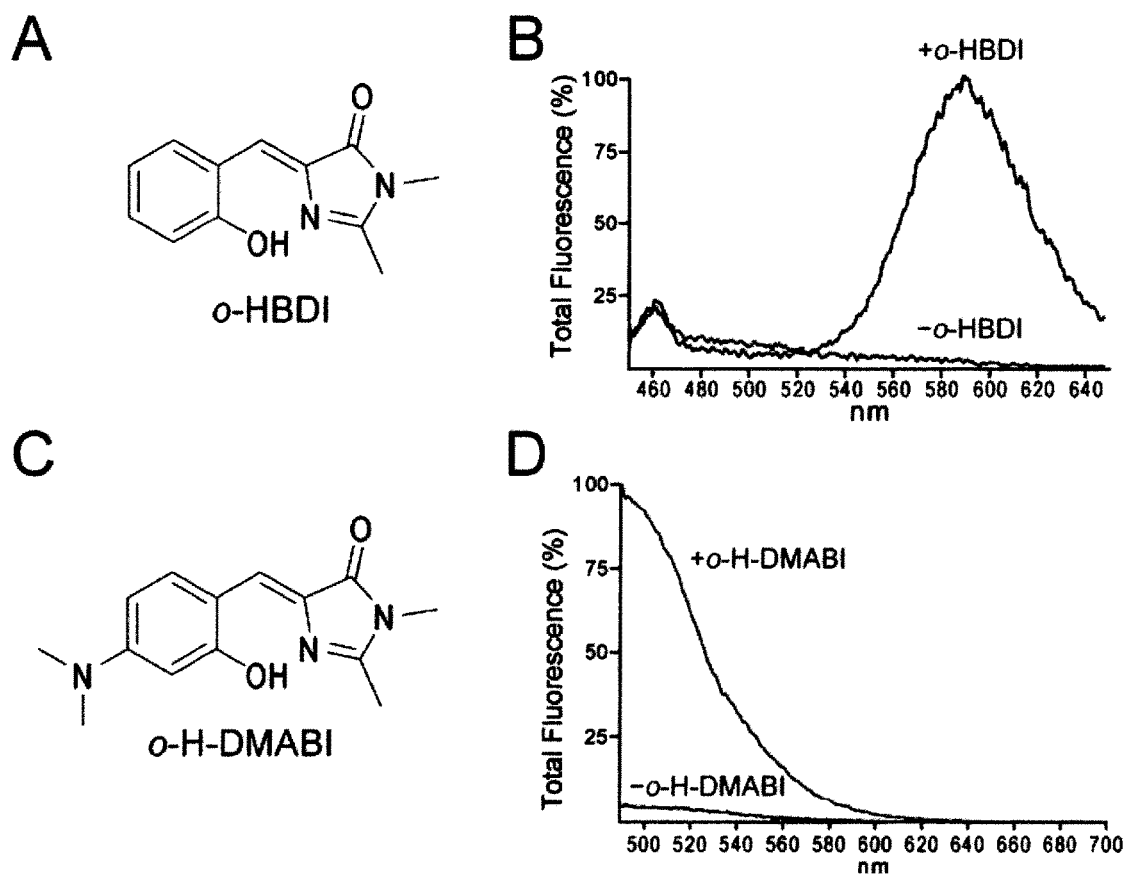
Figures 18A-D

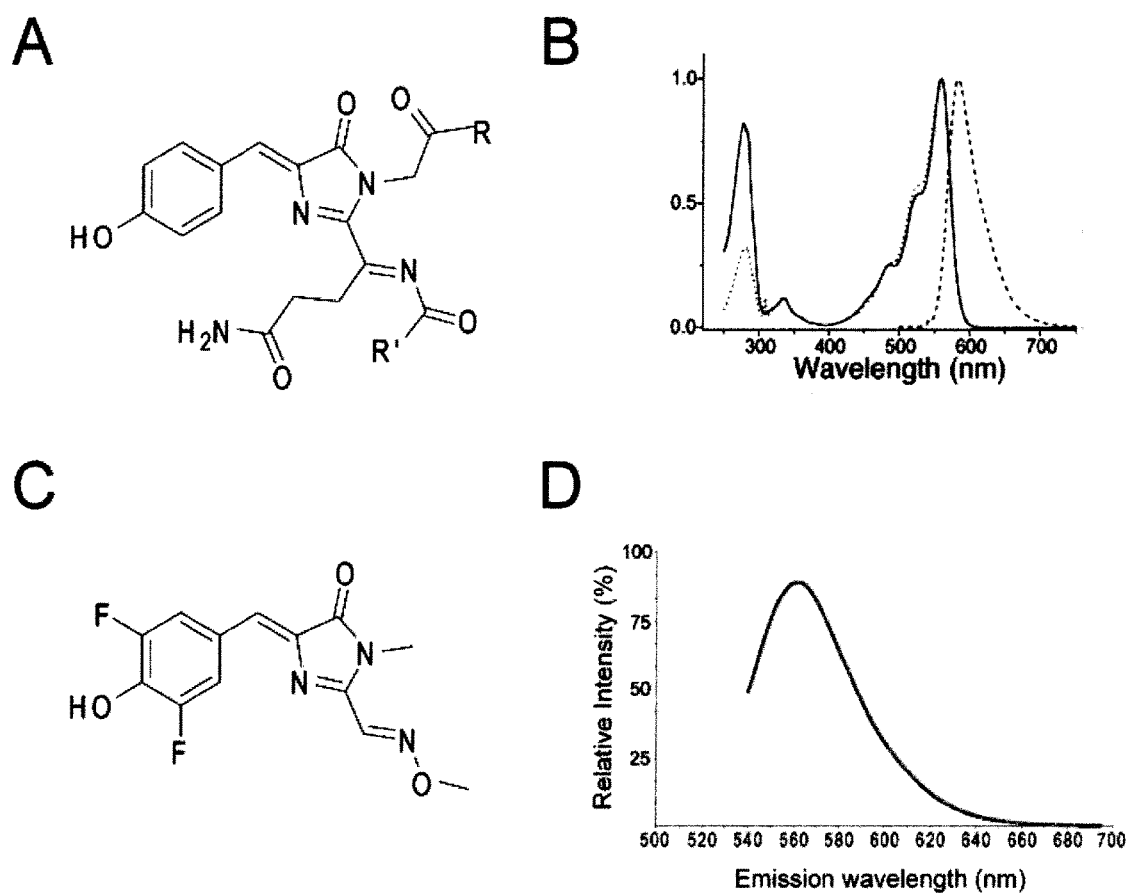
Figures 19A-D

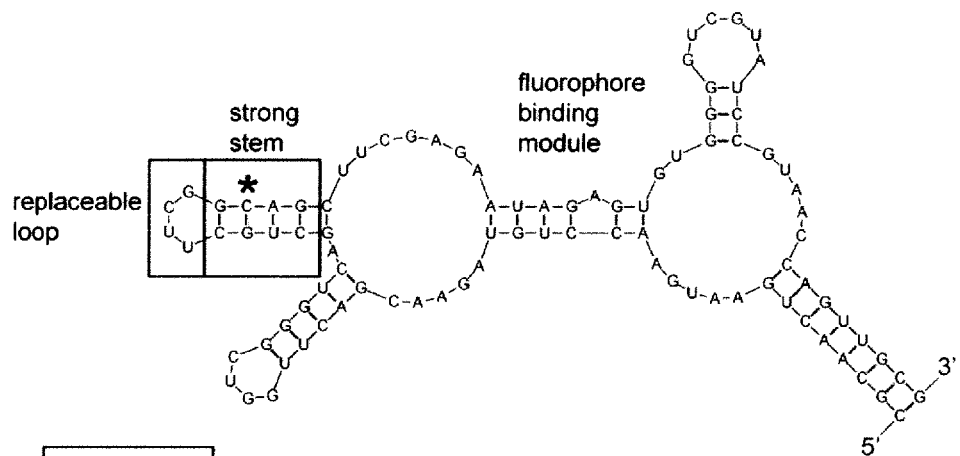
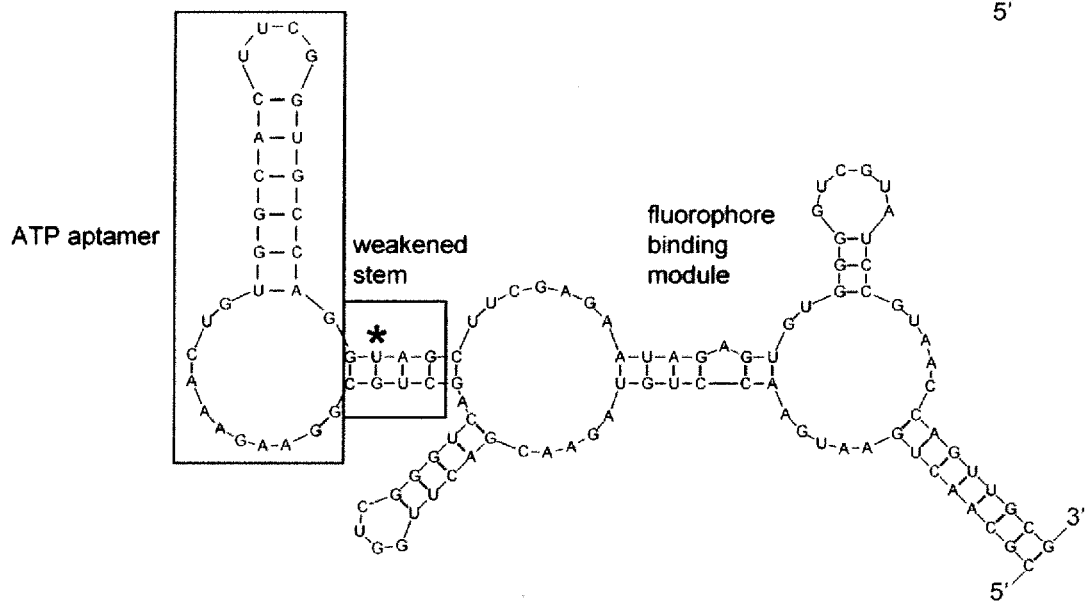
Figures 20A-B

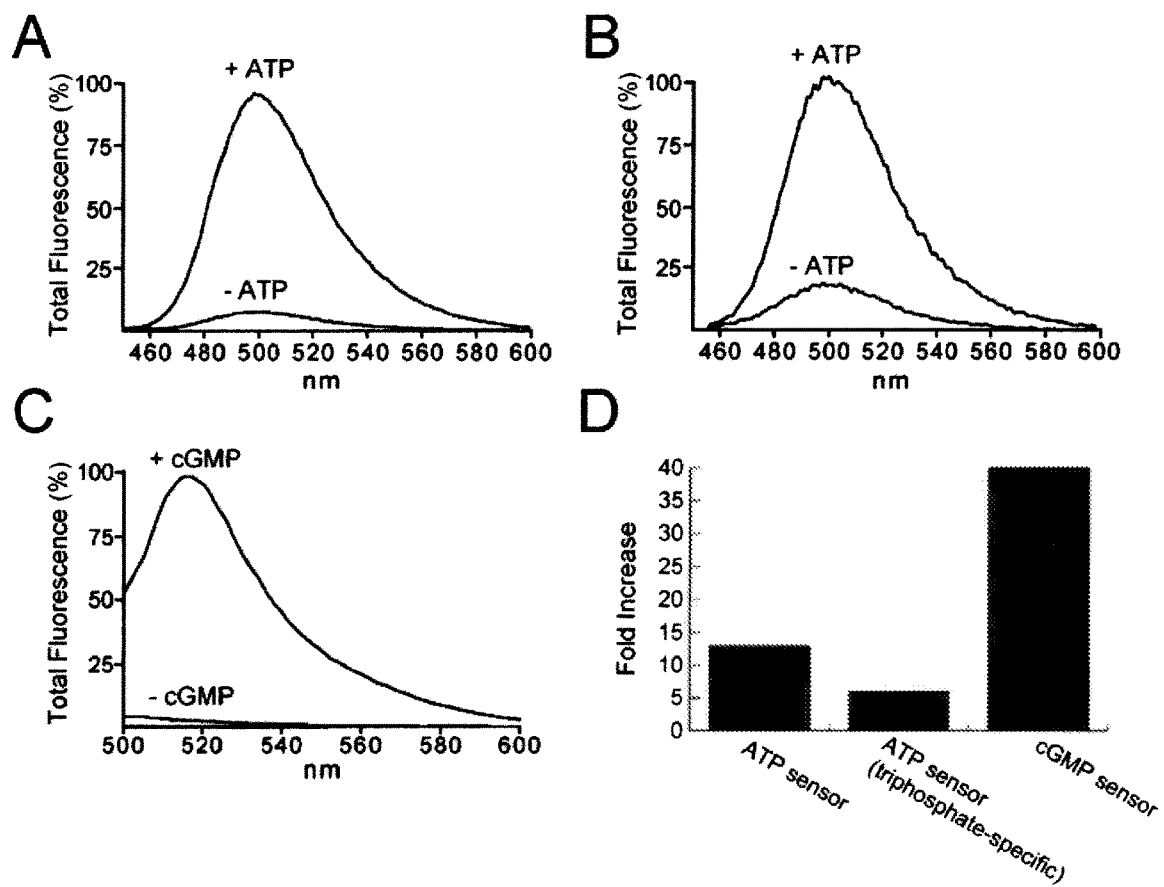
Figures 21A-D

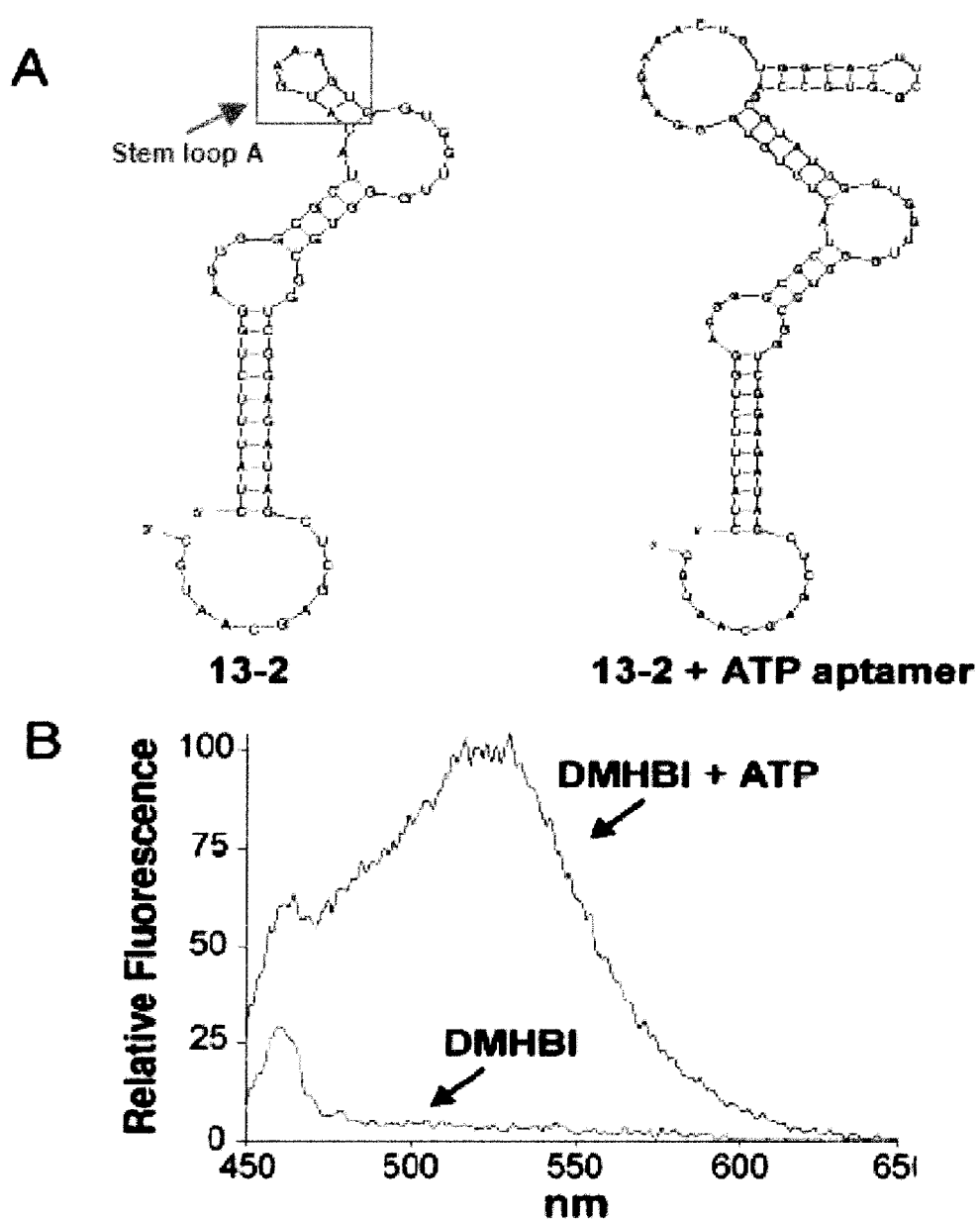
Figures 22A-B

A
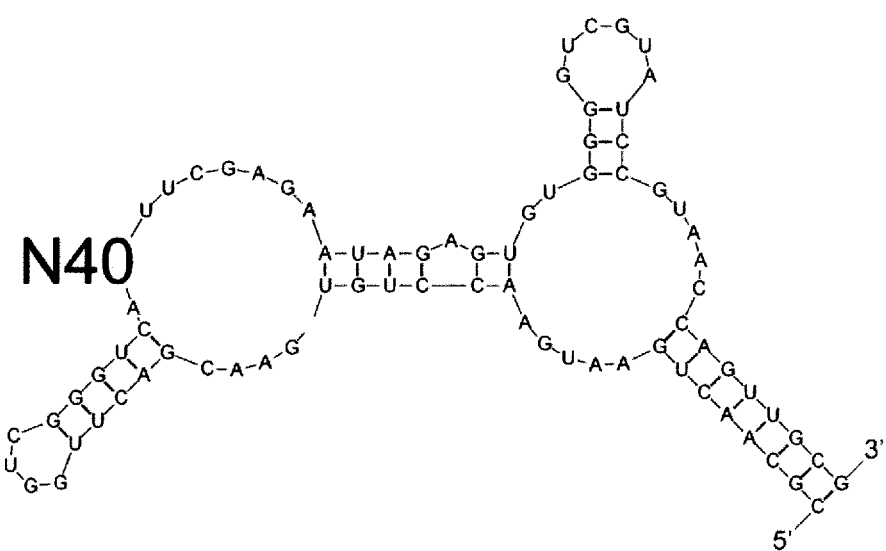
B
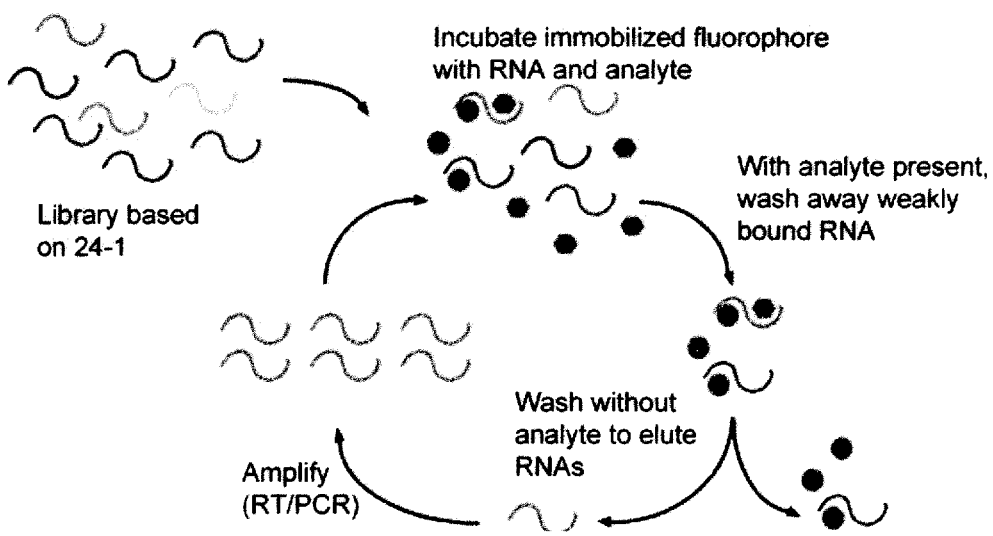
Figures 23A-B

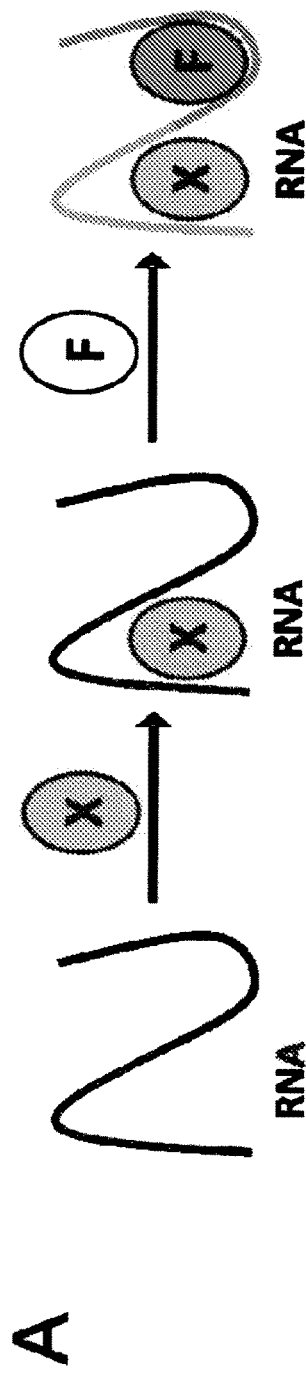
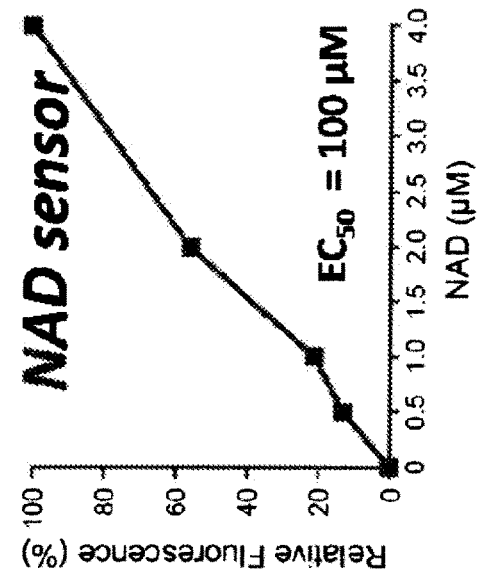
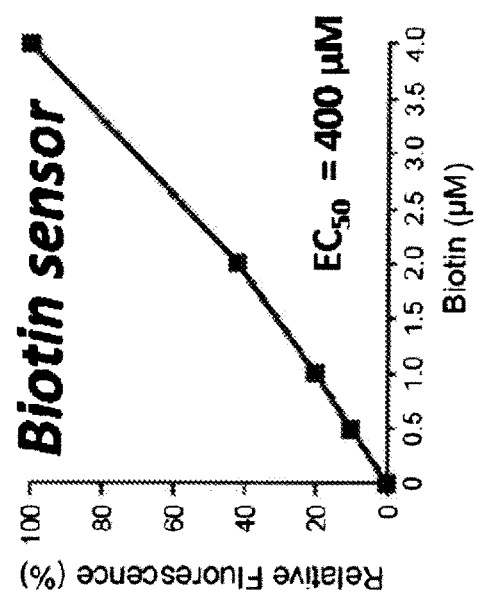
Figures 24A-C

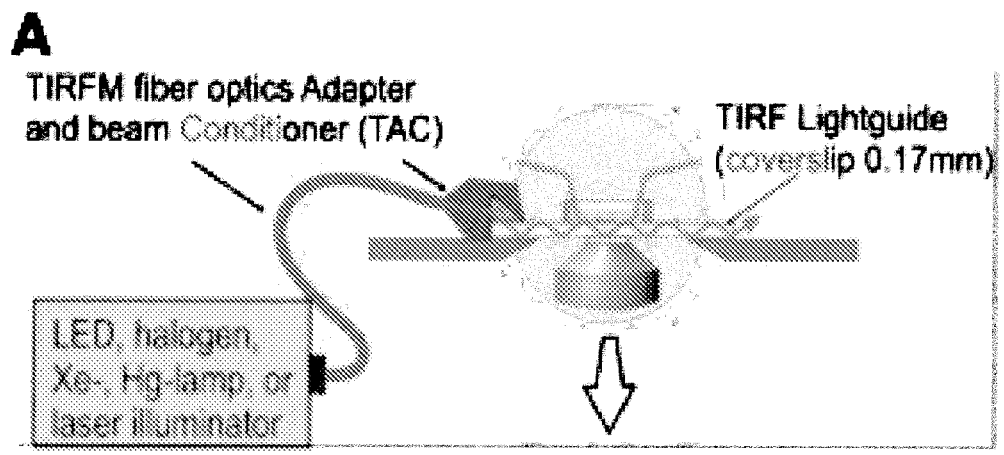
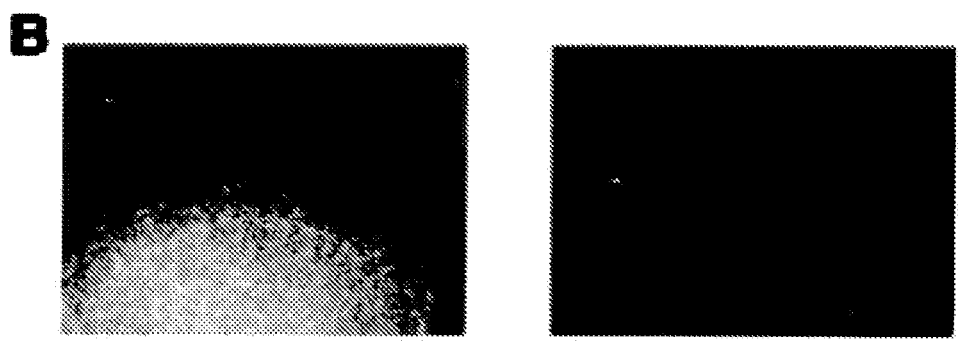
Figures 25A-B

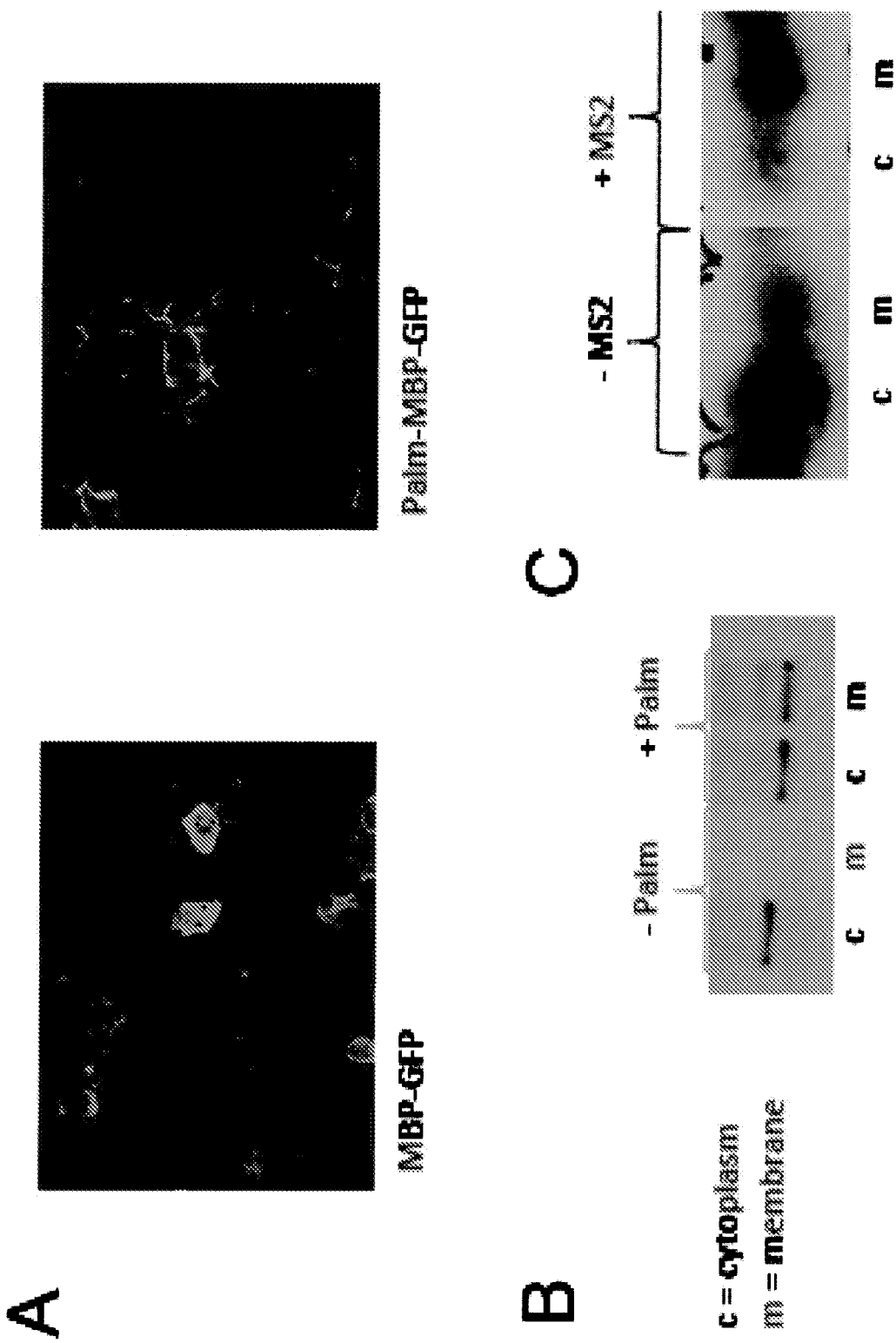
Figures 26A-C

COUPLED RECOGNITION/DETECTION SYSTEM FOR IN VIVO AND IN VITRO USE

This application is a national stage application under 35 U.S.C. § 371 of PCT Application No. PCT/US2010/024622, filed Feb. 18, 2010, which claims the priority benefit of U.S. Provisional Patent Application Ser. No. 61/207,897, filed Feb. 18, 2009, which is hereby incorporated by reference in its entirety.

This invention was made with government support under grant number T32 CA062948 awarded by the National Institutes of Health. The U.S. government has certain rights in the invention.

FIELD OF THE INVENTION

The present invention relates to individual fluorophores, nucleic acid molecules (aptamers) that bind specifically to the fluorophore, molecular complexes containing the aptamers and fluorophores, as well as aptamers that bind specifically to a target molecule, and their use for in vitro or in vivo monitoring of the activity, trafficking, or degradation of various molecules, or the quantification thereof. The present invention also relates to methods and uses for such complexes, as well as kits for practicing those methods.

BACKGROUND OF THE INVENTION

RNA used to be considered a simple and straightforward molecule in cells. The three major classes of RNA, i.e., transfer RNA, ribosomal RNA, and messenger RNA (mRNA), have generally not been thought to be subjected to regulation by signaling pathways, or to have major roles in disease processes. However, a rapidly emerging concept over the past few years is that transcription and other cell signaling pathways are regulated by a diverse array of noncoding RNAs, such as microRNAs, termini-associated RNAs (Han et al., "Promoter-associated RNA Is Required for RNA-directed Transcriptional Gene Silencing in Human Cells," *Proc Natl Acad Sci USA* 104:12422-12427 (2007)), and other noncoding RNAs. Additionally, mRNA is no longer viewed as a simple intermediate between DNA and protein, but instead is now known to be subjected to wide range of post-transcriptional processing events, including diverse types of splicing reactions, nonsense-mediated decay, RNA editing, exo- and endonucleolytic degradation, polyadenylation, and deadenylation. Another intriguing aspect of RNA biology is the finding that trinucleotide repeat-containing mRNAs exert specific gain-of-function toxicities associated with their accumulation at certain intracellular sites (Ranum et al., "Myotonic Dystrophy: RNA Pathogenesis Comes Into Focus," *Am. J. Hum. Genet.* 74:793 (2004)). In addition to these different regulatory pathways, recent studies indicate that RNAs traffic through different parts of the cell during RNA maturation. For example, nascent RNA transcripts are likely trafficked to specific intracellular sites in the nucleus for processing events, such as splicing, nonsense-mediated decay, or for packaging into transport granules. After nuclear export, some RNAs have been localized to RNA-enriched intracellular structures including RNA granules, stress granules, and processing bodies (P-bodies) (Kiebler et al., "Neuronal RNA Granules: Movers and Makers," *Neuron* 51:685-690 (2006)). The diversity of these RNA regulatory mechanisms makes it clear that RNA is regulated by a complex and intricate network of regulatory mechanisms and intracellular structures that have a critical role in gene expression.

RNA regulatory pathways are particularly prominent in neurons. For example, RNA splicing is more highly regulated and is more complex in neurons than in any other cell type (Dredge et al., "The Splice of Life: Alternative Splicing and Neurological Disease," *Nat Rev Neurosci.* 2:43 (2001)). Similarly, RNA editing and trinucleotide repeat-containing mRNA diseases are especially prominent in neurons despite the widespread expression of these transcripts (Keegan et al., "Adenosine Deaminases Acting on RNA (ADARs): RNA-editing Enzymes," *Genome Biol.* 5:209 (2004)). A recent analysis of 1,328 noncoding RNAs (>200 nt) revealed that 64% were expressed in the brain, many of which had strikingly specific patterns of expression in discrete brain structures (Mercer et al., "Specific Expression of Long Noncoding RNAs in the Mouse Brain," *Proc Natl Acad Sci USA* 105:716-721 (2008)).

One form of RNA regulation that has received considerable attention is "local" RNA translation. A compelling argument for a fundamental role for RNA localization in cells was presented in a recent landmark study, in which high-throughput gene-specific in situ hybridization in *Drosophila* embryos showed that 71% of cellular RNAs exhibit specific and often striking intracellular localizations (Lecuyer et al., "Global Analysis of mRNA Localization Reveals a Prominent Role in Organizing Cellular Architecture and Function," *Cell* 131:174-187 (2007)). RNA localization is also a feature of neurons, where mRNAs are enriched in axons and dendrites. Local translation of these mRNAs may have evolved to accommodate the highly spatially polarized nature of neuronal morphology, which typically involves axons and dendrites that can extend distances of tens to thousands of micrometers from the cell body. In local translation, mRNAs are translated directly within dendrites and axons, often within particularly small domains such as a 1-2 µm long dendritic spine or small domain within an axonal growth cone (Steward et al., "Compartmentalized Synthesis and Degradation of Proteins in Neurons," *Neuron* 40:347-59 (2003)). RNAs are dynamically transported between RNA granule structures and P-bodies during synaptic stimulation, which likely regulates mRNA translation (Zeitelhofer et al., "Dynamic Interaction Between P-bodies and Transport Ribonucleoprotein Particles in Dendrites of Mature Hippocampal Neurons," *J Neurosci.* 28:7555-7562 (2008)). Only a small subset of the total mRNA population is trafficked to axons or dendrites, and it appears that discrete 3' UTR sequences are required for signal-dependent translation of distinct pools of RNAs (Sutton et al., "Local Translational Control in Dendrites and its Role in Long-term Synaptic Plasticity," *J Neurobiology* 64:116-131 (2005)). Local translation bypasses the time-consuming process of propagating a signal to the nucleus, followed by protein synthesis and subsequent transport of the newly synthesized protein to the specific site of receptor activation (Steward et al., "Compartmentalized Synthesis and Degradation of Proteins in Neurons," *Neuron* 40:347-359 (2003)). Thus, neurons display complex, time-dependent, and spatially specific regulation of local mRNA translation to accommodate their functional and morphologic demands.

Green fluorescent protein (GFP) has revolutionized biomedical research and biotechnology. As a result of GFP, studies that address the trafficking and processing of proteins in relation to specific intracellular organelles and sites within the cell has become commonplace. Additionally, the roles of organelles and even subdomains within organelles have been elucidated. However, besides the spatiotemporal localization of proteins within cells, GFP has been used to provide information regarding protein-protein interactions, cellular viscosity, and protein degradation (Zhang et al., "Creating New Fluorescent Probes for Cell Biology," *Nature Rev Mol Cell Biol* 3:906-918 (2002); Neher et al., "Latent ClpX-Recognition Signals Ensure LexA Destruction After DNA Damage," *Genes & Development* 17:1084-1089 (2003)). GFP has also been used in studies of protein folding and has found innumerable uses in biotechnology as a critical component of various cell-based and in vivo assays. GFP and related proteins have been harnessed to generate new classes of FRET probes that report the intracellular localization and concentration of intracellular molecules (Zhang et al., "Creating New Fluorescent Probes for Cell Biology," *Nature Rev Mol Cell Biol* 3:906-918 (2002)). Although bioconjugate chemistry methods to make proteins fluorescent have been available for a long time, these approaches require that proteins be modified with agents such as fluorescein isothiocyanate, and then microinjected into cells. Because GFP and GFP-tagged proteins are genetically encodable, they can be expressed from transfected DNA, making the preparation of cells that express fluorescently labeled protein accessible to virtually any biomedical research laboratory. In addition to the ease with which GFP-tagged proteins can be prepared, GFP has been used extensively in live-cell imaging because GFP photobleaches less rapidly than proteins tagged with traditional small molecule fluorescent dyes.

Although GFP has proven to be a valuable tool for studying the cell biology of proteins, similar simple and straightforward technologies for RNA and small molecule visualization are not available. If there were an RNA visualization technology analogous to GFP, it would by a major enabling technology that would permit a wide variety of important questions to be studied. Questions regarding the specific real-time localization of mRNAs, for example, during its processing in the nucleus and nucleolus, and following export to the cytosol and trafficking to neuronal growth cones, spines, axons, nuclei, organelles, etc., could be addressed, especially in terms of specific spliced forms of mRNAs, differentially edited mRNAs, and trinucleotide repeat-containing mRNAs. Furthermore, the timing of mRNA trafficking in response to extracellular signals could be addressed, such as the role of mRNA trafficking to dendritic spines during synaptic plasticity or in growth cones during axon turning. The role of regulated mRNA degradation in dendrites and axons could also be assessed. RNA visualization technologies are not, however, limited to mRNA. In addition to microRNAs, recent studies demonstrate the existence of large numbers of Piwi-interacting RNAs, promoter-associated small RNAs (PASRs), termini-associated small RNAs (TASRs) (Han et al., Promoter-associated RNA is Required for RNA-directed Transcriptional Gene Silencing in Human Cells," *Proc Natl Acad Sci USA* 104:12422-12427 (2007)), as well as a plethora of other small noncoding RNAs (Hannon et al., "The Expanding Universe of Noncoding RNAs," *Cold Spring Harb Symp Quant Biol* 71:551-564 (2006)) whose function is mysterious, but which appear poised to have the same impact on molecular biology as the discovery of microRNAs. Clearly, a wide variety of fundamental questions are waiting to be addressed.

The most commonly used technique to study mRNA localization is in situ hybridization (Levsky et al., "Fluorescence in situ Hybridization: Past, Present and Future," *J Cell Sci.* 116:2833-2838 (2003)). This is a well-established technique, but is not a homogeneous assay and does not allow RNA to be monitored in the same cell at different time points. To achieve real-time, single cell in vivo RNA visualization, one technique has been to synthesize RNA in vitro using fluorescent nucleotides and then microinject them into cells (Zhang et al., "Creating New Fluorescent Probes for Cell Biology," *Nat Rev Mol Cell Biol* 3:906-918 (2002)). This approach is technically difficult and has low throughput. Another approach is to use molecular beacons, which are oligonucleotides that are dual labeled with a fluorophore and a quencher (Tyagi et al., "Imaging Native Beta-actin mRNA in Motile Fibroblasts," *Biophys J.* 87:4153-4162 (2004)). The beacon adopts a stem-loop structure that is nonfluorescent due to the proximity of the fluorophore and quencher at the base of the stem. When a target mRNA that exhibits complementarity to the loop hybridizes to the beacon, the stem is disrupted, resulting in separation of the fluorophore and quencher and subsequent fluorescence. However, transfected beacons exhibit nonspecific nuclear sequestration (Tyagi et al., "Imaging Native Beta-actin mRNA in Motile Fibroblasts," *Biophys J.* 87:4153-4162 (2004)), and each mRNA requires a custom-designed beacon for visualization. Because of the inherent difficulties of these synthetic approaches, numerous groups have attempted to develop genetically encoded reporters of RNA localization in cells. However, because none have shown the requisite simplicity and specificity that are required for general use, RNA imaging still remains a largely inaccessible technology.

The most widely used technique is the GFP-MS2 system (Bertrand et al., "Localization of ASH1 mRNA Particles in Living Yeast," *Molecular Cell* 2:437-445 (1998)). This approach uses two components: MS2, a viral protein, fused to GFP; and MS2-binding elements, which are RNA sequences, inserted into the 3' UTR of RNAs of interest. GFP-MS2 and MS2-element-containing RNAs, or "fusion RNAs," are expressed in cells from transfected DNA. GFP-MS2 binds to the MS2 element-tagged RNA in cells, and fluorescence signals in these cells should represent RNA-GFP complexes. Because unbound GFP-MS2 molecules diffuse throughout the cytosol there would be, in principle, a high fluorescence background. To alleviate this problem, a nuclear localization signal (NLS) is incorporated in the GFP-MS2 fusion protein so that most of the GFP-MS2 moves into the nucleus (Bertrand et al., "Localization of ASH1 mRNA Particles in Living Yeast," *Molecular Cell* 2:437-445 (1998)). Unfortunately, the consequence of this is that GFP-MS2-RNA complexes are subjected to two trafficking signals: one encoded within the RNA and another being the NLS within GFP-MS2. The presence of two trafficking signals confounds interpretation of the intracellular movements of the tagged mRNA. An additional drawback is that the NLS causes the GFP-MS2 to accumulate in the nucleus, resulting in intense nuclear fluorescence signals and thereby preventing the analysis of nuclear-localized RNAs. Since much RNA biology occurs in the nucleus, such as nonsense mediated decay, RNA editing, nuclear export of RNA, splicing, pioneer RNA translation, and microRNA processing, nuclear accumulation of GFP-MS2 impedes the analysis of these events. Thus, even though GFP-MS2 has utility, it is not adequate for the needs of the research community.

Other related approaches have been described which have important limitations. One recent strategy involves the expression of GFP as two separate halves, each fused to half of the protein eIF4A, an RNA-binding protein (Tyagi, S. "Splitting or Stacking Fluorescent Proteins to Visualize mRNA in Living Cells," *Nat Methods* 4:391-392 (2007)). RNAs containing the eIF4A binding site nucleate the binding of the eIF4A halves, which results in the juxtaposition of each GFP half and the subsequent formation of a stable GFP complex. Since the GFP complex requires ~30 min to mature into a fluorescent species (Merzlyak et al., "Bright Monomeric Red Fluorescent Protein with an Extended Fluorescence Lifetime," *Nat Methods* 4:555-557 (2007)), this method does not allow for visualization of nascent RNAs. Additionally, once formed, the fluorescent complex can dissociate spontaneously or after RNA degradation, resulting in high levels of background cytoplasmic fluorescence.

A highly desirable strategy would be to have an RNA sequence that would be fluorescent without the aid of an additional binding protein. However, a potential alternative is to tag RNAs with fluorescent dye-binding RNA sequences. Short RNA sequences that bind other molecules have been termed "aptamers." Using SELEX, RNA aptamers that bind fluorescent dyes such as fluorescein have been described (Holeman, et al., "Isolation and Characterization of Fluorophore-binding RNA Aptamers," *Folding & Design.* 3:423-431 (1998); Sando et al., "Transcription Monitoring using Fused RNA with a Dye-binding Light-up Aptamer as a Tag: a Blue Fluorescent RNA," *Chem Commun (Camb)* 33:3858-3860 (2008)). However, these RNAs have not found use in live-cell experiments because both bound and unbound dye are fluorescent and have nearly identical emission spectrum properties. Thus, if one had cells that expressed the fluorescein-binding aptamers, and then applied fluorescein to the media, the signal from unbound fluorescein would overwhelm the signal from the fluorescein bound to RNA. Similarly, malachite green, although fluorescent when bound to cognate aptamers (Babendure et al., "Aptamers Switch on Fluorescence of Triphenylmethane Dyes," *J Am. Chem. Soc.* 125:14716-14717 (2003)), cannot be used in living cells since malachite green is intensely fluorescent when it interacts with cell membranes (Guidry, G. "A Method for Counterstaining Tissues in Conjunction with the Glyoxylic Acid Condensation Reaction for Detection of Biogenic Amines," *J Histochem Cytochem.* 47:261-264 (1999)). Additionally, malachite green generates radicals that are cytotoxic (Beermann et al., "Chromophore-assisted Laser Inactivation of Cellular Proteins," *Methods in Cell Biology* 44:715-732 (1994)) and rapidly destroy the RNA aptamer itself (Grate et al., "Laser-mediated, Site-specific Inactivation of RNA Transcripts," *Proc. Natl. Acad. Sci. USA* 96:6131-6136 (1999); Stojanovic et al., "Modular Aptameric Sensors," *J Am Chem Soc.* 126:9266-9270 (2004)). These unfortunate features of malachite green have prevented the implementation of these otherwise potentially useful malachite green aptamers in cell imaging.

Other dyes are also problematic. There are numerous molecules that exhibit fluorescence upon binding nucleotides. Ethidium bromide and Hoechst dyes are probably the best known, but these molecules bind oligonucleotides relatively nonspecifically. Consequently, when used in a cellular environment or in vitro medium containing both target and non-target nucleic acid molecules, ethidium bromide and Hoechst dyes will generate a fluorescent signal even in the absence of the target nucleic acid molecule. Cyanine dyes are robustly fluorescent, and they exhibit their fluorescence even when they bind to indiscriminately to membrane components. Cyanine dyes, therefore, suffer from the same problems as malachite green.

It would be desirable, therefore, to generate a fluorophore that generates a sufficiently low background fluorescence in the absence of aptamer binding, whereby the aptamer-bound fluorophore complex generates an enhanced or modified fluorescence signal that is readily distinguishable from the fluorescence signal, if any, of the unbound fluorophore.

The present invention is directed to overcoming these and other deficiencies in the art.

SUMMARY OF THE INVENTION

A first aspect of the present invention relates to a compound comprising a methyne bridge between a substituted aromatic ring system and a substituted imidazol(thi)one, oxazol(thi)one, pyrrolin(thi)one, or furan(thi)one ring, wherein binding of a nucleic acid molecule to the compound substantially enhances fluorescence of the compound upon exposure to radiation of suitable wavelength.

According to one embodiment, the compounds of the first aspect of the invention have the structure of formula I below:

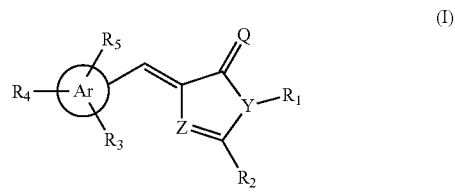

wherein,
Q is S or O,
Y is O or N,
Z is N or C(H),
Ar is an aromatic or hetero-aromatic ring system comprising one or two rings;
$R_1$ is present when Y is N, and is a $C_{1-8}$ hydrocarbon or —$(CH_2)_n$—$R_6$ where n is an integer greater than or equal to 1;
$R_2$ is methyl, a mono-, di-, or tri-halo methyl, oxime, O-methyl-oxime, imine, unsubstituted or substituted phenyl with up to three substituents ($R_7$-$R_9$), $C_{2-8}$ unsaturated hydrocarbon optionally terminated with an amine, amide, carboxylic acid, (meth)acrylate, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, or a second aromatic or hetero-aromatic ring;
$R_3$-$R_5$ are independently selected from H, hydroxy, alkyl, alkoxy, fluoro, chloro, bromo, amino, alkylamino, dialkylamino, alkylthio, cyano, mercapto, nitro, and mono-, di-, or tri-halo methyl, ketone, and carboxylic acid (where at least one of $R_3$-$R_5$ is other than H);
$R_6$ is H, a surface-reactive group, a solid surface, or a functional group that can be linked to a surface-reactive group or solid surface;
$R_7$-$R_9$ are independently selected from H, hydroxy, alkyl, alkoxy, fluoro, chloro, bromo, amino, alkylamino, dialkylamino, alkylthio, cyano, mercapto, nitro, and mono-, di-, or tri-halo methyl, ketone, and carboxylic acid;
and salts thereof.

A second aspect of the invention relates to a nucleic acid molecule that includes a first domain that binds specifically to a fluorophore according to the first aspect of the invention, wherein binding of the nucleic acid molecule to the fluorophore substantially enhances fluorescence of the fluorophore upon exposure to radiation of suitable wavelength. This nucleic acid molecule includes RNA, DNA, and/or modified nucleic acids.

A third aspect of the invention relates to a fusion RNA molecule that includes an RNA molecule according to the second aspect of the invention.

A fourth aspect of the invention relates to a nucleic acid molecule according to the second aspect of the invention, which also includes a second domain that binds specifically to a target molecule that is distinct of the fluorophore. According to one embodiment, the first domain binds to the fluorophore only after the second domain binds to the target molecule.

A fifth aspect of the invention relates to a nucleic acid molecule that includes a first domain that binds specifically to a fluorophore according to the first aspect of the invention and a second domain that includes a random nucleotide sequence, wherein specific binding of the second domain to a target molecule allows the first domain to adopt a structure allowing the first domain specifically to bind to the fluorophore. This aspect of the invention also includes a library that contains a plurality of the nucleic acid molecules.

A sixth aspect of the invention relates to a kit that includes a fluorophore according to the first aspect of the invention and a plurality of nucleic acid molecules according to the second aspect of the invention, wherein each of the plurality of nucleic acid molecules, upon binding, causes a different emission profile by the fluorophore.

A seventh aspect of the invention relates to a kit that includes a plurality of fluorophores according to the first aspect of the invention and a plurality of nucleic acid molecules according to the second aspect of the invention, wherein the plurality of nucleic acid molecules each bind to at least one of the plurality of fluorophores.

An eighth aspect of the invention relates to a molecular complex that includes a fluorophore according to the first aspect of the invention and a nucleic acid molecule according to the second aspect of the invention, which is specifically bound to the fluorophore, wherein the fluorophore has substantially enhanced fluorescence (in comparison to the fluorophore prior to specific binding) upon exposure to radiation of suitable wavelength. This aspect of the invention also includes molecular complexes that include a nucleic acid molecule containing a plurality of first domains.

A ninth aspect of the invention relates to a molecular complex that includes a fluorophore according to the first aspect of the invention; a nucleic acid molecule according to the fourth aspect of the invention, having its first domain specifically bound to the fluorophore and its second domain bound to a target molecule, wherein the fluorophore has substantially enhanced fluorescence (in comparison to the fluorophore prior to specific binding) upon exposure to radiation of suitable wavelength.

A tenth aspect of the invention relates to a host cell that contains a molecular complex according to the eighth or ninth aspects of the invention.

An eleventh aspect of the invention relates to a DNA construct that includes a first region that encodes an RNA molecule according to the second or fourth aspects of the invention. The constructed DNA molecule can be in the form of an isolated transgene or an expression vector (i.e., that include appropriate regulatory sequences to allow for expression of the encoded RNA molecules).

A twelfth aspect of the invention relates to a DNA construct of the eleventh aspect of the invention, which includes an intron positioned within the first region, whereby the excision of the intron from a transcript of the constructed DNA molecule affords the RNA molecule. The constructed DNA molecule can be in the form of an isolated transgene or an expression vector (i.e., that include appropriate regulatory sequences to allow for expression of the encoded RNA molecules).

A thirteenth aspect of the invention relates to a DNA construct that includes a first region that encodes an RNA molecule according to the second or fourth aspects of the invention and a second region that is linked to the first region, the second region encoding an RNA transcript of interest, whereby transcription of the constructed DNA molecule forms an RNA molecule that includes the RNA transcript of interest joined to the RNA molecule that binds specifically to a fluorophore. The constructed DNA molecule can be in the form of an isolated transgene or an expression vector (i.e., that include appropriate regulatory sequences to allow for expression of the encoded RNA molecules).

A fourteenth aspect of the invention relates to a transgenic host cell that includes a DNA construct according to the eleventh, twelfth, or thirteenth aspects of the invention.

A fifteenth aspect of the invention relates to an empty genetic construct that can be used to prepare a DNA construct according to the thirteenth aspect of the invention. The genetic construct includes a promoter sequence operably linked to a first DNA sequence that encodes an RNA molecule according to the second aspect of the invention and a second DNA sequence that contains one or more enzymatic cleavage sites. This aspect of the invention also includes kits that contain the empty genetic construction, and which can be used to prepare the DNA construct according to the thirteenth aspect of the invention.

A sixteenth aspect of the invention relates to a method of detecting a target molecule that includes: first exposing a nucleic acid molecule according to the fourth aspect of the invention (where the first domain binds to the fluorophore only after the second domain binds to the target molecule) to a medium suspected to contain the target molecule under conditions effective to allow the second domain to bind specifically to the target molecule, if present; and second exposing the nucleic acid molecule and medium to a fluorophore comprising a methyne bridge between a substituted aromatic ring system and a substituted imidazol(thi)one, oxazol(thi)one, pyrrolin(thi)one, or furan(thi)one ring under conditions effective to allow the first domain to bind specifically to the fluorophore after binding of the target molecule by the second domain, thereby inducing the fluorophore to adopt a conformation that exhibits enhanced fluorescent emissions; and exciting the fluorophore with radiation of appropriate wavelength and detecting fluorescence by the fluorophore, whereby the detection of fluorescence emissions by the fluorophore indicates binding of the nucleic acid molecule to the target molecule.

A seventeenth aspect of the invention relates to a method of determining location of a target molecule that includes: forming a molecular complex according to the ninth aspect of the invention; exciting the fluorophore with radiation of appropriate wavelength; and detecting fluorescence by the fluorophore, whereby fluorescence by the fluorophore identifies presence of the target molecule.

An eighteenth aspect of the invention relates to a method of measuring transcription by a promoter of interest in a cell, where the method includes: introducing into a cell a DNA construct according to the eleventh aspect of the invention; introducing into the cell a fluorophore in a substantially non-fluorescent form; introducing an agent that modulates transcription of the DNA construct into the cell; and detecting fluorescence by the fluorophore within the cell, whereby the level of fluorescence correlates with the level of transcription for the DNA construct and the effect of the agent in modulating the level of transcription.

A nineteenth aspect of the invention relates to a method of measuring transcription by a promoter of interest, where the method includes: introducing into a cell a DNA construct according to the eleventh aspect of the invention and an agent that modulates transcription of the DNA construct; recovering RNA transcripts from the cell; introducing a fluorophore in a substantially non-fluorescent form to the recovered RNA transcripts; and detecting fluorescence by the fluorophore, whereby the level of fluorescence correlates with the level of transcription by the DNA construct and the effect of the agent in modulating the level of transcription.

A twentieth aspect of the invention relates to a method of monitoring RNA that includes: introducing into a cell a first DNA construct according to the thirteenth aspect of the invention; and introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the RNA molecule encoded by the DNA construct to enhance fluorescence emissions by the first fluorophore; exposing the cell to radiation of a wavelength suitable to induce fluorescence emissions by the first fluorophore that is bound by the first domain or a FRET partner; and measuring the fluorescent emissions of the first fluorophore or the FRET partner to monitor the RNA transcript. This aspect is particularly useful for monitoring the location, degradation (over time), and for quantitating the RNA transcript (i.e., based on the level of fluorescence). Moreover, simultaneous monitoring of two or more RNA transcripts is possible.

A twenty-first aspect of the invention relates to a method of monitoring a target molecule in a cell that includes: introducing into a cell a nucleic acid molecule according to the fourth aspect of the invention (where the first domain binds to the fluorophore only after the second domain binds to the target molecule), wherein the second domain binds the target molecule; introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner to monitor the target molecule. This aspect is particularly useful for monitoring the location, degradation (over time), and for quantitating the target molecule (i.e., based on the level of fluorescence). Moreover, simultaneous monitoring of two or more target molecules is possible.

A twenty-second aspect of the invention relates to a method of monitoring a target molecule in a cell that includes: introducing into a cell a gene encoding the nucleic acid molecule according to the fourth aspect of the invention (where the first domain binds to the fluorophore only after the second domain binds to the target molecule), wherein the second domain binds the target molecule; introducing into the cell a first fluorophore having a methyne bridge between a substituted aromatic ring system and a substituted imidazol (thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner to monitor the target molecule. This aspect is particularly useful for monitoring the location, degradation (over time), and for quantitating the target molecule (i.e., based on the level of fluorescence). Moreover, simultaneous monitoring of two or more target molecules is possible.

A twenty-third aspect of the invention relates to a method of screening a drug that modifies gene expression, which includes: introducing a transgene into a cell under conditions suitable to cause transcription of the gene, the transcript comprising an RNA molecule the second aspect of the invention; exposing the cell to a drug; introducing into the cell a fluorophore having a methyne bridge between a substituted aromatic ring system and a substituted imidazol (thi)one, oxazol(thi)one, pyrrolin(thi)one, or furan(thi)one ring, wherein the fluorophore is bound specifically by the first domain of the RNA molecule to enhance fluorescence emissions by the fluorophore; exposing the cell to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical control cell that is not exposed to the drug, indicates that the drug inhibits expression of the transgene, and an increase of fluorescent emissions, relative to an otherwise identical control cell that is not exposed to the drug, indicates that the drug increases expression of the transgene.

A twenty-fourth aspect of the invention relates to a method of screening a drug that modifies RNA splicing, which includes: introducing into a cell a transgene comprising a DNA construct according to the twelfth aspect of the invention, wherein transcription of the transgene affords a transcript comprising an intron positioned between first and second portions of the RNA molecule; exposing the cell to a drug; introducing into the cell a fluorophore having a methyne bridge between a substituted aromatic ring system and a substituted imidazol(thi)one, oxazol(thi)one, pyrrolin (thi)one, or furan(thi)one ring, wherein the fluorophore is bound specifically by the first domain of the RNA molecule to enhance fluorescence emissions by the fluorophore; exposing the cell to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical control cell that is not exposed to the drug, indicates that the drug inhibits proper splicing of the transcript; and an increase of fluorescent emissions, relative to the otherwise identical control cell that is not exposed to the drug, indicates that the drug promotes proper splicing of the transcript.

A twenty-fifth aspect of the invention relates to method of screening a drug that modifies RNA splicing, which includes: providing a medium comprising an RNA transcript, a spliceosome comprising a splicing enzyme, a drug, and a fluorophore, wherein the RNA transcript comprises first and second exons having an intervening intron region, the first and second exons, upon excision of the intron, forming an RNA molecule according to the second aspect of the invention, wherein the fluorophore has a methyne bridge between a substituted aromatic ring system and a substituted imidazol(thi)one, oxazol(thi)one, pyrrolin(thi)one, or furan (thi)one ring, and wherein the fluorophore is bound specifically by the first domain of the RNA molecule to enhance fluorescence emissions by the fluorophore; exposing the medium to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical medium that lacks the drug, indicates that the drug inhibits proper splicing of the transcript; and an increase of fluorescent emissions, relative to the otherwise identical medium that lacks the drug indicates that the drug promotes proper splicing of the transcript.

A twenty-sixth aspect of the invention relates to a method of screening a drug for activity against a target molecule. The method includes the steps of introducing into a cell a nucleic acid molecule according to the fourth aspect of the invention (where the first domain binds to the fluorophore only after the second domain binds to the target molecule), wherein the second domain binds a target molecule; introducing into the cell a first fluorophore comprising a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner, wherein the a difference in the fluorescent emissions by the fluorophore or FRET partner, relative to an otherwise identical cell that lacks the drug, indicates that the drug modifies the activity of the target molecule.

A twenty-seventh aspect of the invention relates to a method of identifying nucleic acid molecules capable of binding to a target molecule, which method includes: providing a pool of nucleic acid molecules that each comprise a first domain that binds specifically to a fluorophore having a methyne bridge between a substituted aromatic ring system and a substituted imidazol(thi)one, oxazol(thi)one, pyrrolin(thi)one, or furan(thi)one ring, and a second domain that comprises a random sequence, and only after binding of the second domain to the target molecule is first domain capable of binding specifically to the fluorophore; exposing the pool of nucleic acid molecule to a target molecule and the fluorophore, whereby fluorescence emissions by the fluorophore are enhanced by the binding of the first domain to the fluorophore; illuminating the fluorophore with light of a wavelength suitable to induce fluorescence emissions by the fluorophore that is bound by the first domain molecule; and measuring the fluorescent emissions of the fluorophore, whereby detection of fluorescence by the fluorophore indicates that the second domain of the nucleic acid molecule binds to the target molecule.

The examples of the present invention demonstrate the development of an array of fluorophores that exhibit low fluorescence in the absence of specific binding by a nucleic acid aptamer molecule, resulting in an aptamer/fluorophore complex that contains a fluorophore whose fluorescence can be "switched on" only when bound specifically by the aptamer. This solves the problem of many prior art fluorophores, which contribute indiscriminately to background fluorescence. The aptamer/fluorophore complexes of the invention are useful for a wide variety of purposes, both in vitro and in vivo, including monitoring the location or degradation of RNA molecules in vivo, monitoring and quantifying the amount of a target molecule in an in vitro or in vivo system. Importantly, the fluorophores are non-toxic, unlike many prior art dyes. The detection procedures can be implemented using existing optical detection devices and is amenable to high-throughput microarrays or drug screening. Moreover, by virtue of developing a suite of fluorophore/aptamer complexes, each having a unique fluorescent emission spectrum, multiple targets can be addressed simultaneously (i.e., in a single cell) using distinct fluorophore/aptamer pairs for each discrete target. The generation of RNA-based small molecule sensors demonstrates that it is possible to vastly increase the number molecules that can be detected in cells beyond what is possible using current protein-based FRET sensors. The present invention has devised simple strategies to develop sensors for important signaling molecules that can be used in live cell imaging. This was not previously possible using protein-based FRET-based sensors. Thus, the present invention provides a rapid, simple, and general approach to obtain sensors for any small molecule. These sensors should immediately find use as simple fluorometric reagents to measure small molecules, thereby simplifying assays, and permitting high-throughput fluorescence-based screens.

BRIEF DESCRIPTION OF THE DRAWINGS

FIGS. 1A-C show the structure of the native GFP fluorophore and synthesis of 4-(3,5-dimethoxy-4-hydroxy-benzylidene)-1,2-dimethoxy-imidazol-5-one ("DMHBI") derivative. FIG. 1A shows the synthetic route to DMHBI. FIG. 1B shows the ligand immobilized DMHBI. FIG. 1C shows the residues in the crystal structure of the native GFP fluorophore interacting with surrounding residues.

FIGS. 2A-D show that DMHBI is non-fluorescent unless structurally rigidified. FIG. 2A shows that DMHBI is non-fluorescent when dissolved in ethanol at room temperature. Upon freezing to ethanol glass at 77° K the compound becomes brilliantly fluorescent. FIG. 2B shows a graph with glycerol concentration on X-axis and Total Fluorescence on Y-axis. DMHBI fluorescence increases as the concentration of glycerol increases. FIG. 2C shows a micrograph of 10 µM DMHBI incubated with HEK 293 cells. No non-specific fluorescence of DMHBI is observed. FIG. 2D shows a comparative micrograph of 10 µM malachite green incubated with the same cells. The cells turn fluorescent due to non-specific interactions of malachite green.

FIGS. 3A-C show the screening and identification of aptamers that bind to and switch on the fluorescence of DMHBI. FIG. 3A graphically shows the increase in fluorescence of the aptamer library after each round of SELEX. X-axis indicates the number of SELEX rounds and Y-axis indicates the Total Fluorescence of the pool. FIG. 3B shows the excitation and emission spectra of DMHBI bound by aptamers designated 3-6 (SEQ ID NO: 1) and 13-2 (SEQ ID NO: 2). FIG. 3C visually shows the fluorescence obtained when 10 µM DMHBI, 10 µM 13-2 RNA (SEQ ID NO: 2), and 10 µM DMHBI+13-2 RNA were irradiated with UV light. The tube with DMHBI+13-2 RNA shows fluorescence.

FIGS. 4A-B show the full length secondary structures for DMHBI aptamers 3-6 (FIG. 4A, SEQ ID NO: 1) and 13-2 (FIG. 4B, SEQ ID NO: 2) with their free energy predictions calculated at 37° C.

FIGS. 5A-B show the data for dissociation constants and melting temperatures for DMHBI-binding aptamers. In FIG. 5A fluorescence increases were measured against increasing DMHBI concentration to generate a binding curve. The dissociation constant ($K_d$) values for both 3-6 and 13-2 were 400 and 500 nM, respectively. FIG. 5B shows the thermal denaturation curve for 13-2 RNA.

FIGS. 6A-B show the effect of potassium (FIG. 6A) and magnesium (FIG. 6B) concentration on the fluorescence of RNA-DMHBI complexes.

FIG. 9A shows the fluorescence spectrum for aptamer 13-2 and affinity matured aptamer 13-2-5. FIG. 9B shows the thermal denaturation curve for aptamer 13-2-5. FIG. 9C is an alignment of the variable region of DNA clones encoding aptamer 13-2-min (nt 4-60 of SEQ ID NO: 36) and four affinity matured clones (designated "13-2-5", nt 25-81 of SEQ ID NO: 40; "13-2-1", nt 25-81 of SEQ ID NO: 37; 13-2-3", nt 25-81 of SEQ ID NO: 38; and "13-2-4", nt 25-81 of SEQ ID NO: 39) selected against DMHBI from the 13-2 doped library. A consensus sequence of the variable region is also shown (SEQ ID NO: 41).

FIGS. 11A-B show that the fluorophore 3,5-difluoro-4-hydroxy-benzylidene-1,2-dimethyl-imidizolan-5-one ("DFHBI") has a reduced phenolic $pK_a$. FIG. 11A shows the structure of DFHBI fluorophore in the form of its phenolate anion. FIG. 11B shows the $pK_a$ curve for DFHBI measured by taking the ratio of phenolate:phenol absorbance spectra peaks.

FIGS. 12A-D show the characterization of the RNA-DFHBI complex. FIG. 12A shows the excitation and emission spectra for DFHBI:24-1 aptamers. FIG. 12B shows equimolar comparison of brightness of aptamers:fluorophore to DFHBI, DMHBI, and the 4-dimethylaminobenzylidene-1,2-dimethyl-imidazolin-5-one ("DMABI"). FIG. 12C shows equimolar comparison of brightness of 24-1-DFHBI complexes and EGFP. FIG. 12D shows the magnesium dependence of 24-1 and 24-2 aptamers.

FIGS. 13A-C show that aptamers that bind to DFHBI recognize the phenolate form of DFHBI. FIG. 13A shows the absorbance spectra of DFHBI at pH 6, 7 and 8. FIG. 13B shows the excitation spectra for DFHBI-RNA complex at pH 6, 7 and 8. FIG. 13C shows the fluorescence of DMHBI incubated with DFHBI aptamer at pH 7 and 8.

FIG. 14A-B show the predicted secondary structure for aptamers 24-1 (FIG. 14A, SEQ ID NO: 17) and 24-2 (FIG. 14B, SEQ ID NO: 18).

FIGS. 15A-B show that DFHBI:aptamer complexes are fluorescent in live cells. FIG. 15A is an overlay of phase and GFP filter fluorescence image of *E. coli* cells expressing sephadex aptamer and incubated with DFHBI. FIG. 15B is an overlay of phase and GFP filter fluorescence image of *E. coli* cells expressing DFHBI aptamer and incubated with DFHBI.

FIG. 16 depicts emission spectra for DMHBI:aptamer complexes excited at 400 nm. The aptamers were 2-4 (SEQ ID NO: 4), 23-11 (SEQ ID NO: 10), and 17-3 (SEQ ID NO: 6). This figure illustrates that the emission spectra for a single fluorophore can be tailored depending on the aptamer used to bind the fluorophore.

FIGS. 17A-B show aptamers selected against DMABI. FIG. 17A shows the structure of DMABI. FIG. 17B shows the excitation and emission spectra of DMABI following complex formation with aptamer 15-1 (SEQ ID NO: 29).

FIGS. 18A-D show aptamers selected against 2-hydroxybenzylidene-1,2-dimethyl-imidazolin-5-one ("o-HBDI"). FIG. 18A shows the structure of o-HBDI. FIG. 18B shows the emission spectra of o-HBDI following complex formation with aptamer 8-20 (SEQ ID NO: 23). FIG. 18C shows the structure of 2-hydroxy-4-dimethylamino-benzylidene-1,2-dimethyl-imidazolin-5-one ("o-H-DMABI"). FIG. 18D shows the emission spectra of o-H-DMABI following complex formation with aptamer 15-1 (SEQ ID NO: 29).

FIGS. 19A-D show aptamers to biomimetic N-oxime fluorophore. FIG. 19A shows the structure of the prior art DsRed fluorophore. FIG. 19B shows the emission spectra of DsRed (obtained from Campbell et al., "A Monomeric Red Fluorescent Protein," *Proc. Nat'l Acad. Sci USA* 99(12): 7877-7882 (2002), which is hereby incorporated by reference in its entirety). FIG. 19C shows the structure of the fluorophore 4-(3,5-difluoro-4-hydroxy-benzylidene)-1-methyl-2-(O-methyl)oxime-imidazolin-5-one. FIG. 19D shows the emission spectra of this fluorophore in the presence of a pool of RNAs selected against this molecule.

FIGS. 20A-B show the design of a multivalent ATP sensor. FIG. 20A shows the predicted secondary structure of a derivative of aptamer 24-1 (SEQ ID NO: 56) identifying a replaceable loop and strong stem. FIG. 20B shows the modified 24-1:adenosine sensor structure (SEQ ID NO: 32) with the strong stem of 24-1 weakened by a G to U mutation (marked *) and fused with a functional ATP aptamer.

FIGS. 21A-D show the activity of fluorescent sensors based on 24-1 scaffold as modified to include ATP and cGMP aptamers. FIG. 21A shows the response of an adenosine sensor of SEQ ID NO: 32, which recognizes ATP, ADP, and AMP. FIG. 21B shows the response of an ATP sensor that specifically recognizes the triphosphate (SEQ ID NO: 31). FIG. 21C shows the response of a cGMP sensor of SEQ ID NO: 33. FIG. 21D shows the relative fluorescence increase of different sensors upon addition of analyte.

FIGS. 22A-B illustrate the design of a fluorescent ATP sensor using aptamer 13-2. FIG. 22A illustrates how aptamer 13-2 (nt 4-60 of SEQ ID NO: 3, structure from mFOLD, left) was modified by fusing it to a previously-described ATP-aptamer (see structure on right). An unstable stem was fused from the ATP aptamer to 13-2 at the stem A entry point, generating the sensor of SEQ ID NO: 62. FIG. 22B confirms that the fused aptamer construct can be used as an ATP-dependent fluorescent sensor. In the absence of ATP, there is minimal fluorescence, even in the presence of DMHBI (lower curve). However, after addition of 1 mM ATP, the fluorescence increases nearly 30-fold (upper curve). The molar fluorescence intensity of the ATP-bound ATP aptamer was ~20% of the 13-2 parent aptamer, demonstrating that ATP binding was able to significantly restore the DMHBI-binding property of the 13-2 portion of the sensor. These data indicate that 13-2 can be used for the design of other analyte-dependent sensors.

FIGS. 23A-B show the modified SELEX protocol for the development of novel sensors. FIG. 23A shows the library based on 24-1 scaffold. N40 represents a random or selected/amplified 40-nucleotide insert between nt 39 and 40 of SEQ ID NO: 56. FIG. 23B illustrates schematically the selection procedure, whereby novel aptamers that specifically bind a target of interest are selected based on their subsequent specific binding of the 24-1 aptamer to the surface immobilized DFHBI fluorophore.

FIGS. 24A-C illustrate the capability of generating novel sensors via SELEX. FIG. 24A schematically illustrates the principal mode of operation for the "turn-on" sensors. FIG. 24B confirms that the pool of biotin sensors isolated from SELEX exhibits target-dependent fluorescence in the presence of increasing amounts of biotin when provided with DFHBI. FIG. 24C confirms that the pool of NAD sensors isolated from SELEX exhibits target-dependent fluorescence in the presence of increasing amounts of NAD when provided with DFHBI.

FIGS. 25A-B illustrates a TIRF detection system containing a flow cell and fluorescent emissions detected with this detection system. In the TIRF detection system (FIG. 25A), a light source projects light through a slide. A flow cell is attached to the slide. Fluorescent molecules on the glass surface become excited and fluorescent emission is collected through the appropriate objectives, filters, and camera below (i.e., on the side opposite the flow cell). FIG. 25B illustrates the detection of DMHBI fluorescence after it was coupled to an NHS-activated TIRF slide using an aminohexyl linker and then the flow cell was perfused with 1 nM 13-2 (left image). Exposure to 13-2 aptamer resulted in a robust signal. After perfusion with PBS, the flow cell was perfused with 1 nM tRNA, resulting in no signal over the same DMHBI spot (right image). These data show the utility of TIRF in detecting minute quantities of aptamer/fluorophore complexes.

FIGS. 26A-C illustrate the development of a TIRF setup for living cells. FIG. 26A is an image of HEK 293 cells where the MS2 binding protein was tagged with green fluorescent protein (MBP-GFP) and expressed with or without an N-terminal palmitoylation sequence (palm). MBP-GFP becomes membrane localized with the addition of palm sequence. FIG. 26B is an image of a Western blot of lysates obtained from cells expressing constructs for MBP-GFP with or without palm. The cells were lysed and fractionated into membrane and cytosolic fractions. These fractions were then assessed by Western blotting using anti-GFP antibodies. Palm sequence (+Palm) localized MBP-GFP to membrane more. FIG. 26C is an image of a Northern blot using lysates obtained from cells cotransfected with Palm-MBP-GFP and aptamer 24-1 with or without MS2 RNA tag. Cells were lysed and fractionated into membrane and cytosolic fractions. These fractions were then assessed by Northern blot using a probe to the 24-1 sequence. Increased membrane-bound 24-1 RNA was found in cells containing 24-1 with an MS2 tag.

DETAILED DESCRIPTION OF THE INVENTION

Figure 7:
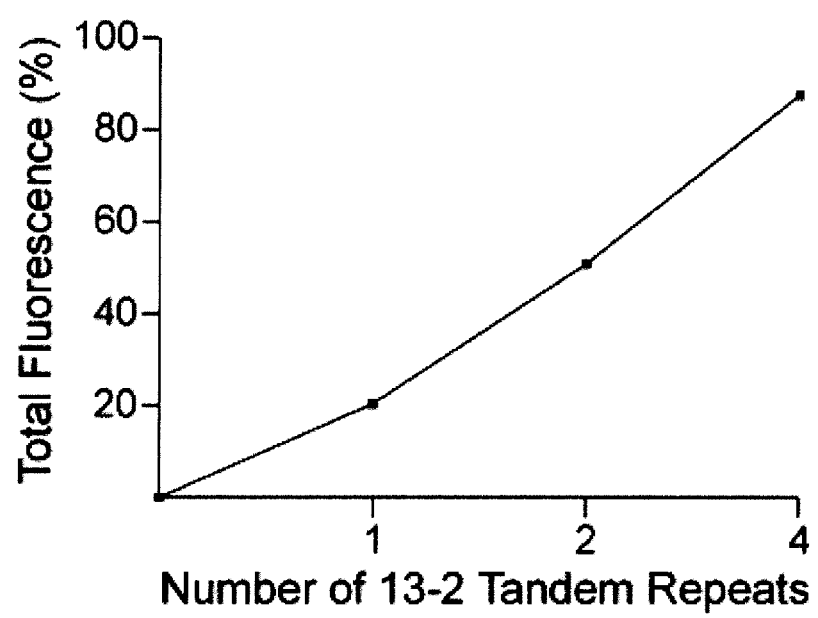
FIG. 7 shows that fluorescence intensity for concatenated DMHBI aptamers increases with increase in the number of tandem repeats of the RNA aptamer.

The present invention relates to novel fluorophores and their use in combination with novel nucleic acid molecules, called aptamers, which bind specifically to the fluorophore and thereby enhance the fluorescence signal of the fluorophore upon exposure to radiation of suitable wavelength. Molecular complexes formed between the novel fluorophores, novel nucleic acid molecules, and their target molecules are also discussed below, as are the uses of these novel materials.

Fluorophores and their Synthesis

According to one aspect of the present invention, the novel fluorophores possess a methyne (also known as methine) bridge between a substituted aromatic ring system and a substituted imidazol(thi)one, oxazol(thi)one, pyrrolin (thi)one, or furan(thi)one ring. Importantly, the methyne bridge contains a single carbon that is double-bonded to a ring carbon of the substituted imidazol(thi)one, oxazol(thi) one, pyrrolin(thi)one, or furan(thi)one ring. Thus, the inventive compounds are unlike cyanine dyes of the prior art which are characterized by a polymethyne bridge.

The fluorophores of the present invention are characterized by a low quantum yield in the absence of aptamer binding. Preferably, the quantum yield of the fluorophore, in the absence of specific aptamer binding, is less than about 0.01, more preferably less than about 0.001, most preferably less than about 0.0001.

The fluorophores are substantially unable to bind molecules other than the aptamer(s) that bind specifically to them. This includes other molecules in a cell or sample besides those aptamer molecules having a polynucleotide sequence that was selected for binding to the fluorophore.

The fluorophores are preferably water soluble, non-toxic, and cell permeable. Preferably, the fluorophore is soluble in an aqueous solution at a concentration of 0.1 µM, 1 µM, more preferably 10 µM, and most preferably 50 µM. Preferably, incubating a cell with these concentrations of the fluorophore does not affect the viability of the cell. The fluorophores are preferably capable of migrating through a cell membrane or cell wall into the cytoplasm or periplasm of a cell by either active or passive diffusion. Preferably, the fluorophore is able to migrate through both the outer and inner membranes of gram-negative bacteria or both the cell wall and plasma membrane of plant cells or plasma membrane of an animal cell.

As used herein, the terms "enhance the fluorescence signal" or "enhanced signal" (i.e., upon specific aptamer binding) refer to an increase in the quantum yield of the fluorophore when exposed to radiation of appropriate excitation wavelength, a shift in the emission maxima of the fluorescent signal (relative to the fluorophore emissions in ethanol glass), or both. The increase in quantum yield is preferably at least about 1.5-fold, more preferably at least about 5 to 10-fold, at least about 20 to 50-fold, more preferably at least about 100 to about 200-fold. Fold increases in quantum yield exceeding 500-fold and even 1000-fold have been achieved with the present invention.

The radiation used to excite the fluorophore may be derived from any suitable source, preferably any source that emits radiation within the visible spectrum or infrared spectrum. The radiation may be directly from a source of radiation (e.g., a light source) or indirectly from another fluorophore (e.g., a FRET donor fluorophore). The use of FRET pairs is discussed more fully hereinafter.

Preferred fluorophores of the present invention include those according to formula I below:

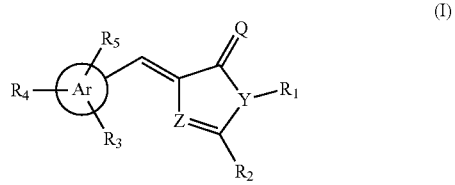

(I)

wherein,
Q is S or O,
Y is O or N,
Z is N or C(H),

Ar is an aromatic or hetero-aromatic ring system comprising one or two rings;

$R_1$ is present when Y is N, and is a $C_{1-8}$ hydrocarbon or $-(CH_2)_n-R_6$ where n is an integer greater than or equal to 1;

$R_2$ is methyl, a mono-, di-, or tri-halo methyl, oxime, O-methyl-oxime, imine, unsubstituted or substituted phenyl with up to three substituents ($R_7$-$R_9$), $C_{2-8}$ unsaturated hydrocarbon optionally terminated with an amine, amide, carboxylic acid, (meth)acrylate, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, or a second aromatic or hetero-aromatic ring;

$R_3$-$R_5$ are independently selected from H, hydroxy, alkyl, alkoxy, fluoro, chloro, bromo, amino, alkylamino, dialkylamino, alkylthio, cyano, mercapto, nitro, and mono-, di-, or tri-halo methyl, ketone, and carboxylic acid;

$R_6$ is H, a surface-reactive group, a solid surface, or a functional group that can be linked to a reactive group on the solid surface; and $R_7$-$R_9$ are independently selected from H, hydroxy, alkyl, alkoxy, fluoro, chloro, bromo, amino, alkylamino, dialkylamino, alkylthio, cyano, mercapto, nitro, and mono-, di-, or tri-halo methyl, ketone, and carboxylic acid As used in the definition of $R_6$, the solid surface can be any solid surface, including glass, plastics, metals, semiconductor materials, ceramics, and natural or synthetic polymers (e.g., agarose, nitrocellulose). The solid surface can be an optically transparent material.

By surface-reactive group, it is intended that the group is a carboxylic acid (which can be modified by a carbodiimide to react with amines), NHS ester, imidoester, PFP ester, p-nitrophenyl ester, hydroxymethyl phosphine, maleimide, haloacetyl group, haloacetamide group, vinyl sulfone, hydrazide, isocyanate, oxirane, epoxide, thiol, amine, alkyne, azide, anhydride, sulfonyl chloride, acyl chloride, ethylenimine, mixed disulfides, activated disulfides, or thiosulfinate. By functional group that can be linked to a reactive group on a solid surface, it is intended that the group is any reactive group, including without limitation, carboxyl, amine, sulfhydryl, aldehyde, hydroxyl, thiol, or any of the groups listed as suitable for the surface-reactive group.

The compounds of the invention also encompass salts, particularly phenolate salts.

Several compounds within the scope of formula I were known previously and are expressly excluded from the scope of the inventive compounds, but not from the scope of the inventive molecular complexes or their use. These include compounds where Ar is phenyl, Z and Y are both N. For those compounds, (i) $R_3$-$R_5$ cannot all be H; (ii) when $R_1$ and $R_2$ are methyl, and $R_4$ and $R_5$ are H, $R_3$ is not hydroxy, methoxy, or dimethylamino; and (iii) when $R_1$ is methyl, $R_4$ and $R_5$ are H, and $R_3$ is hydroxy, $R_2$ is not a conjugated hydrocarbon chain. In addition, the compounds of formula I exclude the compounds disclosed in He et al., "Synthesis and Spectroscopic Studies of Model Red Fluorescent Protein Chromophores," Org. Lett. 4(9):1523-26 (2002); You et al., "Fluorophores Related to the Green Fluorescent Protein and Their Use in Optoelectornic Devices," Adv. Mater. 12(22): 1678-81 (2000); and Bourotte et al., "Fluorophores Related to the Green Fluorescent Protein," Tetr. Lett. 45:6343-6348 (2004), each of which is hereby incorporated by reference in its entirety).

One subclass of the fluorophores, those possessing an oxazolone ring, includes those according to formula Ia:

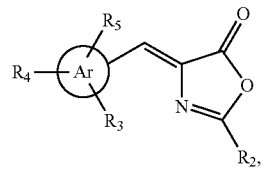

wherein Ar, and $R_2$ to $R_6$ are defined as set forth above.

These compounds of formula Ia can be prepared according to Scheme A or Scheme B below:

Scheme A

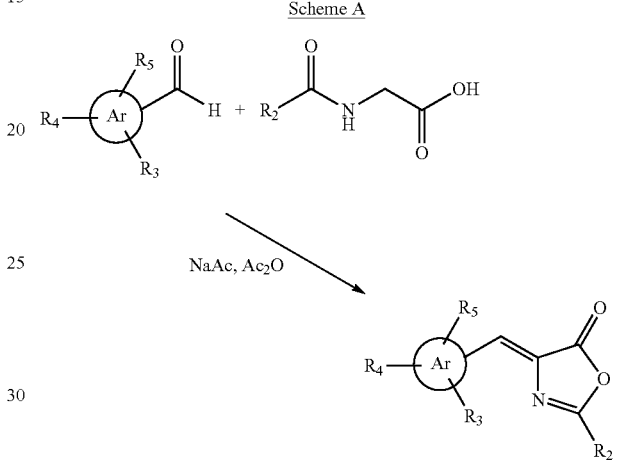

The process of Scheme A can be modified through the use of different starting materials, but fundamentally proceeds according to the process described by Kojima et al., "Fluorescent Properties of Model Chromophores of Tyrosine-66 Substituted Mutants of Aequorea Green Fluorescent Protein (GFP)," Tet. Lett. 39:5239-5242 (1998), which is hereby incorporated by reference in its entirety. Basically, this process involves an Erlenmeyer azalactone formation between the $R_2$-acyl N-derivative of glycine and the aryl aldehyde. A number of $R_2$-acyl N-derivatives of glycine are commercially available from Sigma Chemical and other sources, or readily synthesized from glycine amine with an acid chloride or carboxylic acid (see He et al., "Synthesis and Spectroscopic Studies of Model Red Fluorescent Protein Chromophores," Org. Lett. 4(9):1523-1526 (2002), which is hereby incorporated by reference in its entirety). Also, a number of substituted and unsubstituted aryl aldehydes are commercially available from Sigma Chemical and other sources or readily synthesized.

Scheme B

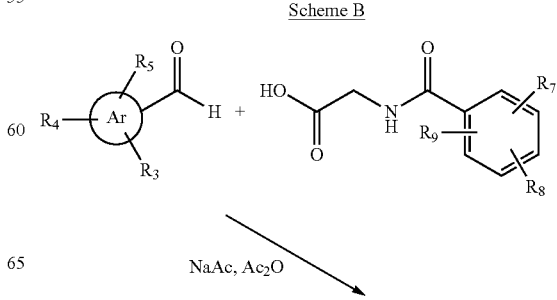

-continued

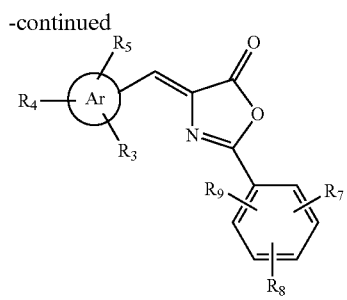

According to Scheme B the aryl aldehyde is reacted with hippuric acid (or a phenyl-ring derivative thereof) to afford those compounds of formula Ia where $R_2$ is a phenyl ring or substituted phenyl ring. The reaction conditions of Scheme B are substantially the same as those employed in Scheme A (see Follenius-Wund et al., "Fluorescent Derivatives of the GFP Chromophore Give a New Insight into the GFP Fluorescence Process," Biophysical Journal 85(3):1839-1850 (2003), which is hereby incorporated by reference in its entirety). Basically, instead of using the $R_2$-acyl N-derivative of glycine, the aryl aldehyde is instead reacted with substituted or unsubstituted hippuric acid. The hippuric acid derivatives can be synthesized from the corresponding acid chloride. Alternatively, benzylidene imidazolinones will be synthesized from the benzaldehyde and (substituted)benzoyl glycine, which can be prepared by reaction of glycine with the corresponding acid chloride.

Conjugated hydrocarbon sidechains can also be introduced at the $R_2$ position using the desired acyl glycine, which can be prepared from the corresponding acid chloride.

Another subclass of the fluorophores, those possessing an imidazolone ring, includes the compounds according to formula Ib:

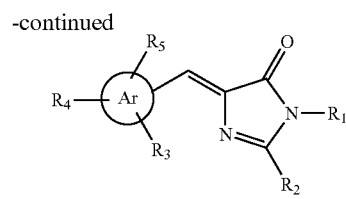
(Ib)

wherein Ar and $R_1$ to $R_6$ are defined as set forth above. These compounds of formula Ib can be synthesized using the compounds of formula Ia and a primary amine ($NH_2$—$R_1$) according to Scheme C below:

Scheme C

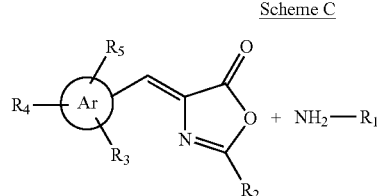

Basically, the azalactone of formula Ia is subjected to aminolysis and subsequent cyclization under alkaline conditions to form the final product of formula Ib.

The corresponding oxazolithiones can be synthesized using the same synthesis scheme illustrated above for the oxazolones except that the glycine derivative possess a thioc acid rather than a carboxylic acid, or a thiohippuric acid can be used (Ya et al., "Cyclization of Thiohippuric Acid in the Presence of a Vilsmeier reagent," Khimiya Geterotsiklicheskikh Soedinenii 1: 36-9 (1980), which is hereby incorporated by reference in its entirety). The oxazolithiones can also be converted into the corresponding imidazolithiones using the reactions illustrated in Scheme C. As an alternative, the keto group of the oxazolones and imidazolones can be converted into thione using $P_2S_5$ under appropriate conditions (see Badr et al., Indian J. Chem., Section B: Organic Chemistry Including Medicinal Chemistry, vol. 18B(3), 240-242 (1979), which is hereby incorporated by reference in its entirety).

Another subclass of the fluorophores, those possessing a furanone ring, includes the compounds according to formula (Ic):

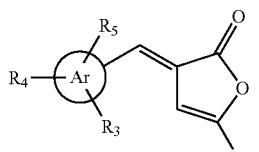
(Ic)

wherein Ar and $R_2$ to $R_6$ are defined as set forth above. These compounds can be prepared in a manner similar to that shown in Scheme A, except that instead of reacting the $R_2$-acyl N-derivative of glycine, the $R_2$-acyl proprionic acid is used instead under substantially the same conditions (see Bourotte et al., "Fluorophores Related to the Green Fluorescent Protein," Tetr. Lett. 45:6343-6348 (2004), which is hereby incorporated by reference in its entirety).

Another subclass of the fluorophores, those possessing a pyrrolinone ring, includes the compounds according to formula Id:

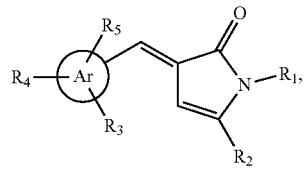
(Id)

wherein Ar and $R_1$ to $R_6$ are defined as set forth above. These compounds can be prepared by reacting the compounds of formula Ic with ammonium acetate in concentrated ammonia (see Bourotte et al., "Fluorophores Related to the Green Fluorescent Protein," *Tetr. Lett.* 45:6343-6348 (2004), which is hereby incorporated by reference in its entirety).

The corresponding furanthiones can be synthesized using the same synthesis scheme illustrated above for the furanones except that the proprionic acid derivative may possess a thioc acid rather than a carboxylic acid group. As an alternative, the keto group of the furanones and pyrrolinones can be converted into thione using $P_2S_5$ under appropriate conditions (see Badr et al., *Indian J. Chem.*, Section B: Organic Chemistry Including Medicinal Chemistry, vol. 18B(3), 240-242 (1979), which is hereby incorporated by reference in its entirety). The pyrrolinthiones can also be converted into the corresponding imidazolithiones using the reactions illustrated in Scheme C.

Further diversification of the compounds can be achieved by conversion of an $R_2$ methyl group in compounds of formula I into an aldehyde using selenium dioxide (with dioxane under reflux). The resulting aldehyde can be converted into a $C_{2-8}$ unsaturated hydrocarbon, preferably a conjugated hydrocarbon, using the Wittig reaction. Basically, the resulting aldehyde is reacted with a triphenyl phosphine (e.g., $Ph_3P=R_{10}$ where $R_{10}$ is the unsaturated hydrocarbon) in the presence of strong base. The unsaturated hydrocarbon that is present in the Wittig reactant is optionally terminated with any desired functional group, preferably an amine, amide, carboxylic acid, (meth)acrylate, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, or a second aromatic or hetero-aromatic ring. These reactants are commercially available or readily synthesized by persons of skill in the art. Alternatively, the resulting aldehyde can be reacted with hydroxylamine or methoxyamine derivative according to the procedure of Maly et al., "Combinatorial Target-guided Ligand Assembly: Identification of Potent Subtype-selective c-Src Inhibitors," *Proc Natl Acad Sci USA* 97(6): 2419-24 (2002), which is hereby incorporated by reference in its entirety) (see compounds of formulae IIIa, IIIb below). The aldehyde can also be reacted with nitromethane to form acrylonitro groups according to established protocols (see Muratore et al., "Enantioselective Bronsted Acid-catalyzed N-acyliminium Cyclization Cascades," *J Am Chem Soc* 131(31):10796-7 (2009); Crowell and Peck, *J. Am. Chem. Soc.* 75:1075 (1953), each of which is hereby incorporated by reference in its entirety). Additionally, aldehydes can be reacted with nucleophilic cyano-containing molecules such as 2-cyanoacetamide, malononitrile methylcyanoacetate, cyano acetic acid, etc., in a Knoevenagel condensation reaction to produce acrylonitrile groups with different functional groups (Cope et al., *J. Am. Chem. Soc.* 63:3452 (1941), which is hereby incorporated by reference in its entirety).

Alternatively, the $R_2$ methyl can be replaced with a mono-, di-, or tri-halomethyl group. Halo-substituted acetamides are readily available, and are sufficiently reactive with the arylaldehydes.

In the compounds of formula I (including the compounds of formulae Ia-Id), Ar can be any single or multiple (including fused) ring structure, except as noted above when Ar is phenyl. Preferred Ar groups include substituted phenyl, naphthalenyl pyridinyl, pyrimidinyl, pyrrolyl, furanyl, benzofuranyl, thiophene-yl, benzothiophene-yl, thiazolyl, benzothiazolyl, imidizolyl, benzoimidizolyl, oxazolyl, benzoxazolyl, purinyl, indolyl, quinolinyl, chromonyl, or coumarinyl groups. The substituents of these Ar groups can be one or more of hydroxy, alkyl, alkoxy, fluoro, chloro, bromo, amino, alkylamino, dialkylamino, alkylthio, cyano, mercapto, nitro, mono-, di-, or tri-halo methyl, ketone, and carboxylic acid. The aromatic or hetero-aromatic group terminating the $R_2$ group can also be any one or the Ar groups identified above.

One preferred subclass within formula Ib are the tri-substituted benzylidene imidazolones of formula II:

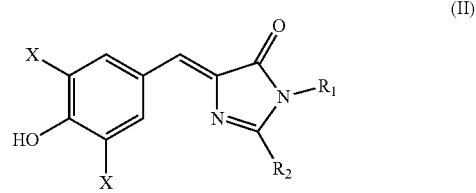

(II)

where X is fluoro, chloro, or bromo, and $R_1$ and $R_2$ are as defined above for formula I. In the compounds of formula II, $R_1$ is preferably methyl, ethyl, or $(CH_2)_6$—$NH_2$, and $R_2$ is methyl, oxime, or O-methyl-oxime.

Another preferred subclass within formula Ib are the $R_2$ oximes and O-methyl-oximes according to formula IIIa and IIIb:

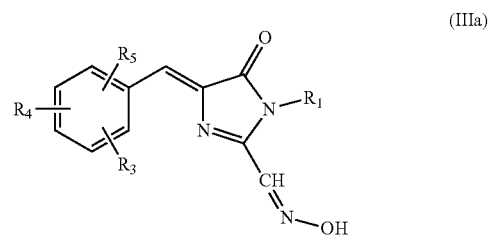

(IIIa)

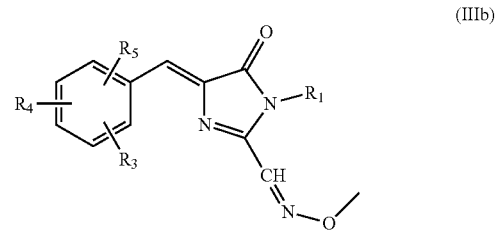

(IIIb)

where $R_1$ and $R_3$-$R_5$ are as defined above for formula I.

Exemplary fluorophores that have been prepared and have been shown to exhibit low quantum yield in the absence of aptamer binding are identified below:

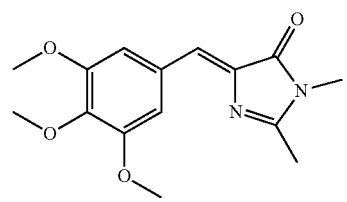

4-(3,4,5-trimethoxybenzylidene)-1,2-dimethyl-imidazol-5-one ("TMBI")

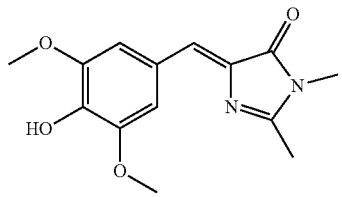

4-(4-hydroxy-3,5-dimethoxybenzylidene)-1,2-dimethyl-imidazol-5-one ("DMHBI")

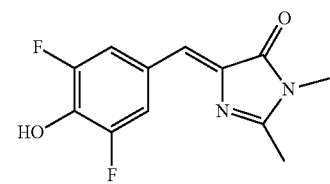 [SMILES: CC1=N/C(=C\c2cc(F)c(O)c(F)c2)C(=O)N1C]

4-(3,5-difluoro-4-hydroxybenzylidene)-1,2-dimethyl-imidazol-5-one ("DFHBI")

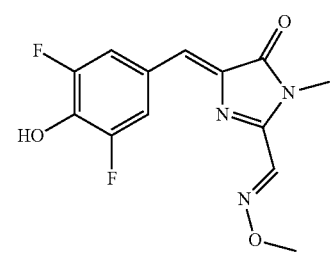 [SMILES: CO/N=C/C1=NC(=C\c2cc(F)c(O)c(F)c2)/C(=O)N1C]

4-(3,5-difluoro-4-hydroxy-benzylidene)-1-methyl-2-(O-methyl)oxime-imidazolin-5-one

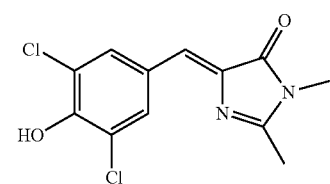 [SMILES: CC1=N/C(=C\c2cc(Cl)c(O)c(Cl)c2)C(=O)N1C]

4-(3,5-dichloro-4-hydroxybenzylidene)-1,2-dimethyl-imidazol-5-one

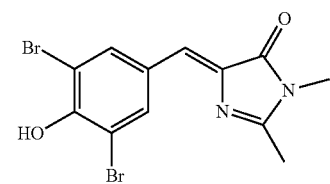 [SMILES: CC1=N/C(=C\c2cc(Br)c(O)c(Br)c2)C(=O)N1C]

4-(3,5-dibromo-4-hydroxybenzylidene)-1,2-dimethyl-imidazol-5-one

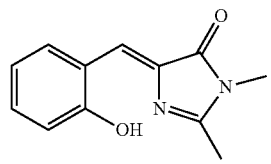 [SMILES: CC1=N/C(=C\c2ccccc2O)C(=O)N1C]

4-(2-hydroxybenzylidene)-1,2-dimethyl-imidazol-5-one ("o-HBI")

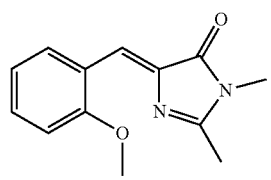 [SMILES: COc1ccccc1/C=C1\N=C(C)N(C)C1=O]

4-(2-methoxybenzylidene)-1,2-dimethyl-imidazol-5-one

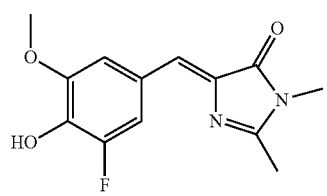 [SMILES: COc1cc(/C=C2\N=C(C)N(C)C2=O)cc(F)c1O]

4-(3-fluoro-4-hydroxy-5-methoxybenzylidene)-1,2-dimethyl-imidazol-5-one

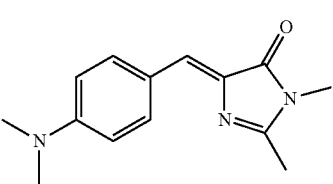

4-(4-(dimethylamino)benzylidene)-1,2-dimethyl-imidazol-5-one ("DMABI")

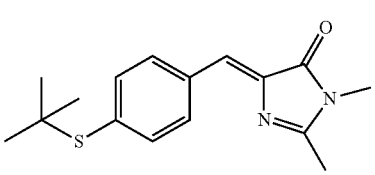 [SMILES: CC1=N/C(=C\c2ccc(SC(C)(C)C)cc2)C(=O)N1C]
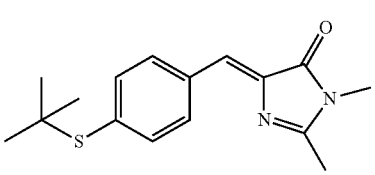 [SMILES: CC1=N/C(=C\c2ccc(SC(C)(C)C)cc2)C(=O)N1C]

25

4-(4-(t-butylthio)benzylidene)-1,2-dimethyl-imidazol-5-one

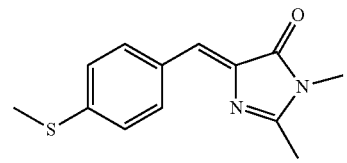

4-(4-(methylthio)benzylidene)-1,2-dimethyl-imidazol-5-one

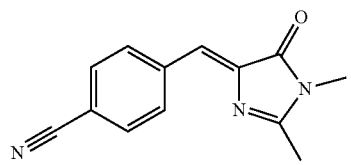 [SMILES: CC1=N/C(=C\c2ccc(C#N)cc2)C(=O)N1C]

4-(4-cyanobenzylidene)-1,2-dimethyl-imidazol-5-one

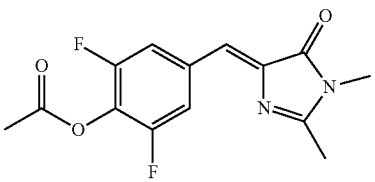 [SMILES: CC(=O)Oc1c(F)cc(/C=C2\N=C(C)N(C)C2=O)cc1F]

4-(3,5-difluoro-4-acetate)benzylidene-1,2-dimethyl-imidazol-5-one

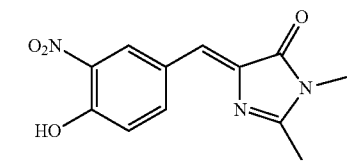 [SMILES: CC1=N/C(=C\c2ccc(O)c([N+](=O)[O-])c2)C(=O)N1C]

4-(4-hydroxy-3-nitrobenzylidene)-1,2-dimethyl-imidazol-5-one

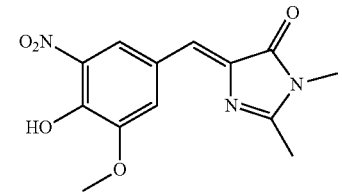 [SMILES: COc1cc(/C=C2\N=C(C)N(C)C2=O)cc([N+](=O)[O-])c1O]

26

4-(4-hydroxy-3-methoxy-5-nitrobenzylidene)-1,2-dimethyl-imidazol-5-one

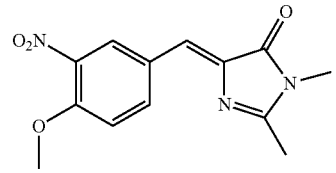 [SMILES: COc1ccc(/C=C2\N=C(C)N(C)C2=O)cc1[N+](=O)[O-]]

4-(4-methoxy-3-nitrobenzylidene)-1,2-dimethyl-imidazol-5-one

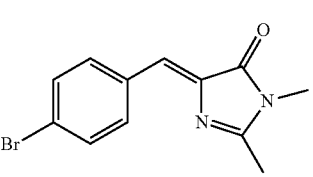 [SMILES: CC1=N/C(=C\c2ccc(Cl)cc2)C(=O)N1C]

4-(4-bromobenzylidene)-1,2-dimethyl-imidazol-5-one

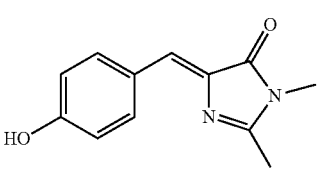 [SMILES: CC1=N/C(=C\c2ccc(O)cc2)C(=O)N1C]

4-(4-chlorobenzylidene)-1,2-dimethyl-imidazol-5-one

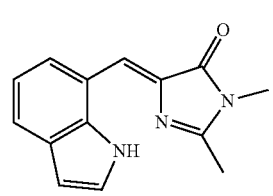 [SMILES: CC1=N/C(=C\c2cccc3cc[nH]c23)C(=O)N1C]

4-(4-hydroxybenzylidene)-1,2-dimethyl-imidazol-5-one ("p-HBI")

4-((indol-7-yl)methylene)-1,2-dimethyl-imidazole-5-one

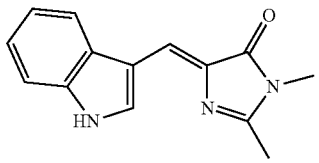 [SMILES: CC1=N/C(=C\c2c[nH]c3ccccc23)C(=O)N1C]

4-((indol-3-yl)methylene)-1,2-dimethyl-imidazole-5-one

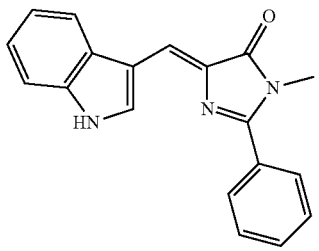 [SMILES: CN1C(=O)/C(=C/c2c[nH]c3ccccc23)N=C1c1ccccc1]

4-((indol-3-yl)methylene)-1-methyl-2-phenyl-imidazole-5-one

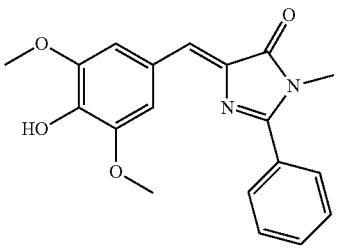

4-(4-hydroxy-3,5-dimethoxybenzylidene)-1-methyl-2-phenyl-imidazole-5-one

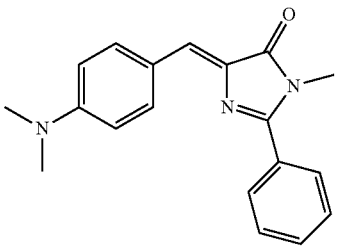

4-(4-(dimethylamino)benzylidene)-1-methyl-2-phenyl-imidazole-5-one

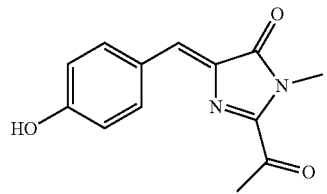 [SMILES: CC(=O)C1=N/C(=C\c2ccc(O)cc2)C(=O)N1C]

4-(4-hydroxybenzylidene)-2-acetyl-1-methyl-imidazole-5-one

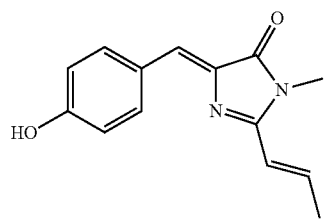 [SMILES: C/C=C/C1=NC(=C\c2ccc(O)cc2)/C(=O)N1C]

4-(4-hydroxybenzylidene)-1-methyl-2-prop-1-enyl-imidazole-5-one

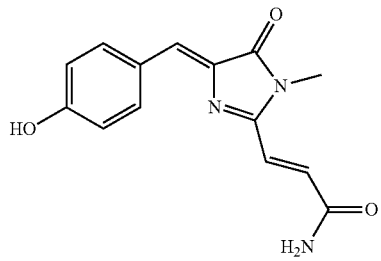 [SMILES: CN1C(=O)/C(=C/c2ccc(O)cc2)N=C1/C=C/C(N)=O]

3-(4-(4-hydroxybenzylidene)-4,5-dihydro-1-methyl-5-oxo-imidazol-2-yl)acrylamide

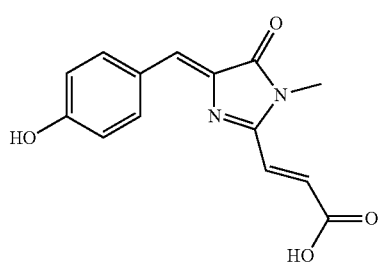 [SMILES: CN1C(=O)/C(=C/c2ccc(O)cc2)N=C1/C=C/C(=O)O]

3-(4-(4-hydroxybenzylidene)-4,5-dihydro-1-methyl-5-oxo-imidazol-2-yl)acrylic acid and

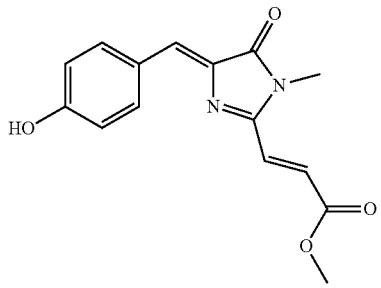 [SMILES: COC(=O)/C=C/C1=NC(=C\c2ccc(O)cc2)/C(=O)N1C]

methyl 3-(4-(4-hydroxybenzylidene)-4,5-dihydro-1-methyl-5-oxo-imidazol-2-yl)acrylate If cell permeability is a problem for some fluorophores, then acylation of phenolic moieties should improve the cell permeability without impacting fluorophore activity, as these acyl moieties are rapidly cleaved by intracellular esterases (Carrigan et al., "The Engineering of Membrane-permeable Peptides," Anal Biochem. 341:290-298 (2005), which is hereby incorporated by reference in its entirety). For fluorophores with low cell permeability, their O-acyl esters can be trivially made by reacting the fluorophores with the appropriate acid chloride, e.g., myristoyl, octanoyl, or butanoyl chloride. To the extent that these acyl moieties are not rapidly cleaved, these may in fact improve the fluorescence of the various RNA-fluorophore complexes.

Aptamers

The present invention also relates to nucleic acid molecules that are known in the art as aptamers. Aptamers are nucleic acid molecules characterized by a single-strand and having a secondary structure that may possess one or more stems (i.e., base-paired regions) as well as one or more non base-paired regions along the length of the stem. These non base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they noncovalently bind their target molecule through an interaction such as an ion-ion force, dipole-dipole force, hydrogen bond, van der Waals force, electrostatic interaction, stacking interaction or any combination of these interactions.

Identifying suitable nucleic acid aptamers basically involves selecting aptamers that bind a particular target molecule with sufficiently high affinity (e.g., $K_d$<500 nM) and specificity from a pool or library of nucleic acids containing a random region of varying or predetermined length. For example, identifying suitable nucleic acid aptamers of the present invention can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," Nature 346:818-822 (1990); and Tuerk and Gold, "Systematic Evolution of Ligands by Exponential Enrichment: RNA Ligands to Bacteriophage T4 DNA Polymerase," Science 249:505-510 (1990), each of which is hereby incorporated by reference in their entirety. An established template-primer system (Bartel et al., "HIV-1 Rev Regulation Involves Recognition of Non-Watson-Crick Base Pairs in Viral RNA," Cell 67:529-536 (1991), which is hereby incorporated by reference in its entirety) can be adapted to produce RNA molecules having a stretch of about 38-40 random bases sandwiched between 5' and 3' constant regions.

The synthetic oligonucleotide templates can be amplified by polymerase chain reaction ("PCR") and then transcribed to generate the original RNA pool. Assuming that ten percent of the RNA molecules are free of chemical lesions that prevent second-strand synthesis and transcription, this pool would contain more than $3 \times 10^{13}$ different sequences. Because filter binding is applicable for most protein targets, it can be used as the partitioning device, although other suitable schemes can be used. The selected primary RNA aptamers can be cloned into any conventional subcloning vector and sequenced using any variation of the dideoxy method. Next, the secondary structure of each primary RNA aptamer can be predicted by computer programs such as MulFold or mFOLD (Jaeger et al., "Improved Predictions of Secondary Structures for RNA," Proc. Natl. Acad. Sci. USA 86:7706-7710 (1989), and Zuker, "On Finding All Suboptimal Foldings of an RNA Molecule," Science 244:48-52 (1989), each of which is hereby incorporated by reference in its entirety). Mutational studies can be conducted by preparing substitutions or deletions to map both binding sites on the RNA aptamer and its target molecule, as well as to further enhance aptamer binding affinity, as described in the accompanying Examples.

Aptamers generated from SELEX experiments can be optimized to produce second generation aptamers with improved properties (Eaton et al., "Post-SELEX Combinatorial Optimization of Aptamers," Bioorg. Med. Chem. 5:1087-1096 (1997), which is hereby incorporated by reference in its entirety). As demonstrated in the accompanying Example, one round of affinity maturation of a primary SELEX clone resulted in five aptamers, each with a higher fluorescence and higher quantum yield than the original, with the best having twice the quantum yield and fluorescence. Therefore, prior to using aptamers in cell-based experiments, each aptamer can be optimized using the following considerations:

Find the minimal aptamer sequence within the SELEX clone to identify the domain to subject to affinity maturation. This will lead to more desirable, smaller aptamers, which should be better for tagging RNAs with aptamers;

It is important to know if the aptamers are selective for their intended fluorophore or if they bind other fluorophores that are intended to bind to other aptamers. In dual color imaging experiments involving two RNA-fluorophore complexes, cross-reactive fluorophores would be problematic.

The fluorescence of the aptamer-fluorophore complexes needs to be optimized by affinity maturation. This may avoid unwanted interference or FRET.

Additionally, tagging the RNA with multiple tandem aptamers rather than a single aptamer will increase the fluorescence of a tagged RNA. Tagging of the aptamers should be possible without impacting the aptamer ability to bind specifically to a particular fluorophore or target molecule of interest.

If any cross-reactivity is observed, then a doped library can be prepared and subjected to "negative selection," also called "counter-SELEX." There is considerable precedent that documents the ability of negative selection to generate aptamers with high degrees of selectivity, even among closely related molecules (Tuerk et al., "Using the SELEX Combinatorial Chemistry Process to Find High Affinity Nucleic Acid Ligands to Target Molecules," *Methods Mol Biol.* 67:219-230 (1997); Rink et al., "Creation of RNA Molecules that Recognize the Oxidative Lesion 7,8-dihydro-8-hydroxy-2'-deoxyguanosine (8-oxodG) in DNA," *Proc Natl Acad Sci USA* 95:11619-11624 (1998); Haller et al., "In vitro Selection of a 7-Methyl-guanosine Binding RNA that Inhibits Translation of Capped mRNA Molecules," *Proc Natl Acad Sci USA* 94:8521-8526 (1997); Edwards et al., "DNA-oligonucleotide Encapsulating Liposomes as a Secondary Signal Amplification Means," *Anal Chem.* 79:1806-1815 (1997), each of which is hereby incorporated by reference in its entirety). To perform negative selection, RNAs bound to dye-agarose are subjected to a washing step in which the buffer contains other fluorophores. This results in the elution of aptamers that have undesirable cross-reactivity. The RNAs that remain bound to the agarose beads are then eluted with the fluorophore of interest, and amplified as in the classic SELEX procedure. This process is repeated until clones are generated which do not bind and activate the fluorescence of inappropriate fluorophores.

Optimization of aptamers can also be achieved during re-selection by using rigorous washing conditions in all steps, including the use of high temperature (37° C. or 45° C.) washing buffers, mild denaturants, and low salt and high salt washes, etc. Since the quantum yield may reflect the efficiency of the RNA to conformationally restrict the photoexcited fluorophores, RNA aptamers that bind more tightly to the fluorophore may improve the quantum yield, and thereby the fluorescence of the RNA-fluorophore complexes. The proposed stringent washing conditions are intended to select for aptamers that bind more tightly to the fluorophore, and thereby improve the quantum yield. An additional benefit of generating RNA aptamers that bind with higher affinity to the fluorophore is that lower concentrations of fluorophore will be needed for live-cell experiments, which may reduce potential off-target or cytotoxic effects of the fluorophore. Since most aptamers that bind to small molecules bind with modest affinity, i.e., a $K_d$ of >100 nM (Famulok et al., "Nucleic Acid Aptamers—from Selection in vitro to Applications in vivo," *Accounts of Chemical Research* 33:591-599 (2000), which is hereby incorporated by reference in its entirety), it is expected that this high affinity will not affect the resistance to photobleaching.

Another method to use during optimization is the use of a smaller bias during doping. For example, the library can be doped with a 2:1:1:1 ratio instead of 5:1:1:1. This will result in more library members being substantially different from the parent aptamer.

The SELEX procedure can also be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Single stranded DNA aptamers have advantages for in vitro settings due to their ease of synthesis and greater stability. Recent studies have argued that proper buffer conditions and certain RNA sugar modifications can lead to highly stable RNAs (Osborne et al., "Aptamers as Therapeutic and Diagnostic Reagents: Problems and Prospects," *Curr Opin Chem Biol.* 1:5-9 (1997); Faria et al., "Sugar Boost: When Ribose Modifications Improve Oligonucleotide Performance," *Current Opinion in Molecular Therapeutics* 10:168-175 (2008), each of which is hereby incorporated by reference in its entirety). Additionally, microarrays of RNAs have been shown to be stable in the presence of tissue lysates when suitable RNAase inhibitors are added (Collett et al., "Functional RNA Microarrays for High-throughput Screening of Antiprotein Aptamers," *Anal Biochem.* 338:113-123 (2005), which is hereby incorporated by reference in its entirety). Moreover, as part of the optimization and stabilization process, stabilizing hairpins can be added which markedly enhance aptamer levels in cells (Blind et al., "Cytoplasmic RNA Modulators of an Inside-out Signal-transduction Cascade," *Proc Natl Acad Sci USA* 96:3606-3610 (1999), which is hereby incorporated by reference in its entirety). Regardless, DNA aptamer sequences that switch on fluorophores of the invention would be inexpensive to synthesize and provide additional assurance of sensor stability in solution phase or microarray-based assays.

SELEX can be performed as readily with DNA as with RNA (Breaker, "DNA Aptamers and DNA Enzymes," *Curr Opin Chem Biol.* 1:26-31 (1997), which is hereby incorporated by reference in its entirety). The absence of a 2'-OH does not substantially impair the ability of DNA to fold or adopt structures. Indeed, SELEX has been used to identify DNAs that bind both small molecules and proteins, with structures that are reminiscent of RNA aptamers. Thus, DNA aptamers can be developed and subjected to analogous mutagenesis and truncation studies to identify entry points and analyte sensors as described for 13-2 above.

As used herein, "nucleic acid" includes both DNA and RNA, in both D and L enantiomeric forms, as well as derivatives thereof (including, but not limited to, 2'-fluoro-, 2'-amino, 2'O-methyl, 5' iodo-, and 5'-bromo-modified polynucleotides). Nucleic acids containing modified nucleotides (Kubik et al., "Isolation and Characterization of 2' fluoro-, 2' amino-, and 2' fluoro-amino-modified RNA Ligands or Human IFN-gamma that Inhibit Receptor Binding," *J. Immunol.* 159:259-267 (1997); Pagratis et al., "Potent 2'-amino, and 2'-fluoro-2'-deoxy-ribonucleotide RNA Inhibitors of Keratinocyte Growth Factor," *Nat. Biotechnol.* 15:68-73 (1997), each which is hereby incorporated by reference in its entirety) and the L-nucleic acids (sometimes termed Spiegelmers®), enantiomeric to natural D-nucleic acids (Klussmann et al., "Mirror-image RNA that Binds D-adenosine," *Nat. Biotechnol.* 14:1112-1115 (1996) and Williams et al., "Bioactive and nuclease-resistant L-DNA Ligand of Vasopressin," *Proc. Natl. Acad. Sci. USA* 94:11285-11290 (1997), each which is hereby incorporated by reference in its entirety), are used to enhance biostability. In addition, the sugar-phosphate backbone can be replaced with a peptide backbone, forming a peptide nucleic acid (PNA). The use of PNA is also contemplated.

According to one embodiment, the nucleic acid molecule includes a first domain—an aptamer—that binds specifically to a fluorophore having a methyne bridge between a substituted aromatic ring system and a substituted imidazol(thi)one, oxazol(thi)one, pyrrolin(thi)one, or furan(thi)one ring. Preferably, the fluorophore is a compound according to any of formulae I (Ia-d), II, or III. The nucleic acid molecule, upon binding to the fluorophore, induces the fluorophore to adopt a conformation whereby the fluorescent emission spectra is substantially enhanced upon exposure to radiation of suitable wavelength.

The nucleic acid aptamers of the present invention include both monovalent aptamers that contain a single first domain for binding to the fluorophore, as well as multivalent aptamers that contain more than one aptamer domain.

According to one embodiment, the multivalent aptamers can include a plurality of first domains for binding to multiple identical fluorophore compounds per molecule. These can be in the form of concatamers of a single type of aptamer that binds to a single fluorophore. Examples of these concatamers that have proven to be useful for expanding the fluorescent emissions per molecule include 2-mers, 4-mers, 8-mers, 12-mers, 16-mers, and 32-mers. In forming these concatamers, the plurality of aptamer domains can be separated by linker regions of suitable length that prevent steric interference between the domains and their target fluorophores. Alternatively, the concatamers can contain multiple types of aptamer that bind to a several different fluorophores, and collectively achieve a blended emission profile.

Exemplary aptamer molecules that bind specifically to the fluorophore DMHBI are identified below:

```
Aptamer 3-6
                                            (SEQ ID NO: 1)
GGGAGAUACGCUCUAGAAUUCAAUUGCAUGGUGGUCUGGGACAGACGUGU

GGACGGCACACAGCGUGAGGCUUUGGUGGGUUAUGGCUGUCAUGCGAGAU

AGCUCGAGCAAUGC

Aptamer 13-2
                                            (SEQ ID NO: 2)
GGGCUAUUUCUGGAGGGGCGCUACAUGAAAGUGGUGGUUGGGUGCGGUCG

GAGAUAGCUCGAGCAAUGC

Aptamer 13-2-min
                                            (SEQ ID NO: 3)
GGGCUAUUUCUGGAGGGGCGCUACAUGAAAGUGGUGGUUGGGUGCGGUCG

GAGAUAGCUC

Aptamer 2-4
                                            (SEQ ID NO: 4)
UGAAACCUAGAGUUAUGCCAGGCUCUGAGCCUGCUUCGGCAGGUGCUAUG

AUCGCCAGCGGUAUGCAGUCCG

Aptamer 4-19
                                            (SEQ ID NO: 5)
UGAAAUGACAGUACAGUGGAGGGUGCNGUACUGCUUCGGCAGGGAAGGGG CGCUGUUCUUGUCUCAUAUCCG,
where N is C or U at each position.

Aptamer 17-3
                                            (SEQ ID NO: 6)
UGAAGAGCAGUAGCGAGUAGUUCACAANAGCUGCUUCGGCAGGAUCUUGU AGGAAGUAAAUGUGCAAAUCCG,
where N is C or U at each position.

Aptamer 17-17
                                            (SEQ ID NO: 7)
UGAAANNAAAUAUUCGGGAUANAUANNAUUACUGCUUCGGCAGANAGCGG UUAAUUNUUGNAANUCNAAUCCCG,
where N is C or U at each position.

Aptamer 18-16
                                            (SEQ ID NO: 8)
UGAANGGACUCGUCUGGCNGGAUGGGCGNGUGGUACUGCUUUCGGGCAGG AUNGGGUAUAACGGUANANGCNC,
where N is C or U at each position.

Aptamer 23-7
                                            (SEQ ID NO: 9)
UGAAAUGACAGUACAGUGGAGGGUGCGGUACUGCUUCGGCAGGGAAGGGG

CGCUGUUCUUGUCUCAUAUCCG

Aptamer 23-11
                                            (SEQ ID NO: 10)
GGGAGACGCAACUGAAUGAAAUGACAGUACAGUGGAGGGUGCGGUACUGC

UUCGGCAGGGAAGGGGCGCUGUUCUUGUCUCAUAUCCGUAACUAGUCGCG

UCAC

Aptamer 13-2-1
                                            (SEQ ID NO: 11)
GGGUAUCCGGAAUCUUAUACAUUGUUAUGUCUGGAGGGGCGCCGCAUGAA

CGCGGUGGUGAGGUGCGGUCGGAUAUAACUGGUGGAGUGCAAGAGUCUGA

GCACACUGG

Aptamer 13-2-3
                                            (SEQ ID NO: 12)
GGGUAUCCGGAAUCUUAUACAUUGCUAUUUCUGGAGGGGCGCCCCAUGAA

AGGGGUGGUUGAGAGCGGUCGGAGAUAGCGGAAACAGUGCAAGAGUCUGA

GCACACUGG

Aptamer 13-2-4
                                            (SEQ ID NO: 13)
GGGUAUCCGGAAUCUUAUACAUUGCUAUUGUUGGAGGGGCGCUACGUGAA

AGUGGUGGUACGGUGCGGUCGGCAAUAGCUCGUAUAGUGCAAGAGUCUGA

GCACACUGG

Aptamer 13-2-5
                                            (SEQ ID NO: 14)
GGGUAUCCGGAAUCUUAUACAUUGCUCUGUUUGGAGGGGCGCUACUUUCA

AGUAGUGGUUGAGUGCGGUCGAACAGAGCUUGGGCGUUGCAAGAGUCUGA

GCACACUGG

Aptamer 13-2-5-min
                                            (SEQ ID NO: 15)
GGGUAUCCGGAAUCUUAUACAUUGCUCUGUUUGGAGGGGCGCUACUUUCA

AGUAGUGGUUGAGUGCGGUCGAACAGAGCUUGGGCGUUGCAAGAGUC
```

Exemplary aptamer molecules that bind specifically to the fluorophore DFHBI are identified below:

```
Aptamer 24-4
                                            (SEQ ID NO: 16)
GGGAGACGCAACUGAAUGAACGGGGUAAAUAGGCGUGGGUCGGGUCCUGC

UUCGGCAGUUGAGUGUGAGAGCGAACUCUGUAGUUCCGCGUAACUAGUCG

CGUCAC

Aptamer 24-1
                                            (SEQ ID NO: 17)
GGGAGACGCAACUGAAUGAACCUGUAGAACGACUUGGUCGGGUCAGCUGC

UUCGGCAGCUUCGAGAAUAGAGUGUGGGGUCGUAUCCGCGUAACUAGUCG

CGUCAC

Aptamer 24-2
                                            (SEQ ID NO: 18)
GGGAGACGCAACUGAAUGAAAUGGUGAAGGACGGGUCCAGGUGUGGCUGC

UUCGGCAGUGCAGCUUGUUGAGUAGAGUGUGAGCUCCGCGUAACUAGUCG

CGUCAC

Aptamer 10-6
                                            (SEQ ID NO: 19)
UGAAUGAACGGGGUAAAUAGGCGUGGGUCGGGUCCUGCUUCGGCAGUUGA

GUGUGAGAGCGAACUCUGUAGUUCCG
```

Exemplary aptamer molecules that bind specifically to the fluorophore o-HBI are identified below:

```
Aptamer J2-6
                                     (SEQ ID NO: 20)
UGAAAAUGGCAAAAUAUUCGAGAANCUGGUCUGCUUCGGCAGGAUUCUCC AAGGGGUAGAUCGUGUAUUCCG,
where N is C or U at each position.

Aptamer J2-18
                                     (SEQ ID NO: 21)
UGAAAAUGUNNNAUNCGAGNCNGNAUUNAGCUGCUUCGGCAGAANGNUCU CCCANAGCUNNUGNCAAAUCCG,
where N is C or U at each position.

Aptamer S8-9
                                     (SEQ ID NO: 22)
UGAAAAUGUAUAGUCGGAUGUGCNGANUNNACUGCUUCGGCAGCUUAGAU GUAUGCAGCUGCUCGGGAGUCCG,
where N is C or U at each position.

Aptamer S8-20
                                     (SEQ ID NO: 23)
UGAAUCUCCGUGUCAGGGCAGAGCAGGGCGCUGCUUCGGCAGAUAAUGUA

UAGUCGGGAUCGCUGAACUCCG
```

Exemplary aptamer molecules that bind specifically to the fluorophore DMABI are identified below:

```
Aptamer N19-4
                                     (SEQ ID NO: 24)
UGAACGAAUAGGUGGAGGUUGCNCUGUUUUCUGCUUCGGCAGGUUAAAGA UUGGUACUCAUCACGGUGUCCG,
where N is C or U at each position.

Aptamer N19-10
                                     (SEQ ID NO: 25)
UGAACAGUUUCGUGCAGUUUGAAAUGUAGGCUGCUUCGGCAGGAUAGGUG

UGGAGGUGGAUGUCCGGGUCCG

Aptamer N9-1
                                     (SEQ ID NO: 26)
UGAACCCUGAAAAGAGGGAAGGCCUGGNUUGCUGCUUCGGCAGGGGAUUG

AUCAGGGUGCACGUUGCUGUCCG

Aptamer N9-6
                                     (SEQ ID NO: 27)
UGAAGCCUUGAAAUAGUAGUGAUCGAGUGGCUGCUUCGGCAGACUCUGAG

UGUGGCUAUACGUGAUCGUCCG

Aptamer N11-3
                                     (SEQ ID NO: 28)
UGAAAAGUGGUAUUUNAAAUUCNANUUANCUGCUUCGGCAGACGACGGG GGGGCNNGUNUUGGANGAUCCG,
where N is C or U at each position.

Aptamer N15-1
                                     (SEQ ID NO: 29)
UGAAUGUNGCAUAAUUGANGGANGAUNCAUGCUGCUUCGGCAGUUGGGUG UAAAAAUGGAANGAGGUCNUAUCCG,
where N is C or U at each position.

Aptamer N8-4
                                     (SEQ ID NO: 30)
UGAAUCCAGGGGUGGUCGGUGGNNGGAGCGCUGCUUCGGCAGUGAGCUGG GGAGUUCAGUCAAUGUGGUCCG,
where N is C or U at each position.
```

According to another embodiment, multivalent nucleic acid aptamer molecules can include one or more first domains that bind specifically to multiple identical fluorophore compounds per molecule, and one or more second domains that bind specifically to a target molecule of interest (i.e., one that is distinct of the fluorophore). Also contemplated herein are concatemers of these dual domain aptamer molecules, having the structure (first domain-second domain)$_m$, where m is an integer greater than 1. The first domain of each functional two-domain sensor can be the same or different. Likewise, the second domain of each functional two-domain sensor can be the same or different.

The target molecule of interest can be any biomaterial or small molecule including, without limitation, proteins, nucleic acids, lipids, carbohydrates, hormones, cytokines, chemokines, metabolites, organic molecules, and metal ions. The target molecule of interest can be one that is associated with a disease state or pathogen infection.

Proteins or polypeptides targets can be any length, and can include, without limitation, phosphoproteins, lipid-modified proteins, nitrosylated proteins, sulfenated proteins, acylated proteins, methylated proteins, demethylated proteins, C-terminal amidated proteins, biotinylated proteins, formylated proteins, gamma-carboxylated proteins, glutamylated proteins, glycylated proteins, iodinated proteins, hydroxylated proteins, isoprenylated proteins, lipoylated proteins (including prenylation, myristoylation, farnesylation, palmitoylation, or geranylation), proteins covalently linked to nucleotides such as ADP ribose (ADP-ribosylated) or flavin, oxidated proteins, proteins modified with phosphatidylinositol groups, proteins modified with pyroglutamate, sulfated proteins, selenoylated proteins, proteins covalently linked to another protein (including sumoylation, neddylation, ubiquitination, or ISGylation), citrullinated proteins, deamidated proteins, eliminylated proteins, disulfide bridged proteins, proteolytically cleaved proteins, proteins in which proline residues have been racemized, any peptides sequences that undergo the above mentioned modifications, and proteins which undergo one or more conformational changes. In addition, proteins or peptides that possess a mutation can be distinguished from wildtype forms. Complexes of two or more molecules include, without limitation, complexes have the following interactions: protein-protein, protein-cofactor, protein-inhibiting small molecules, protein-activating small molecules, protein-small molecules, protein-ion, protein-RNA, protein-DNA, DNA-DNA, RNA-DNA, RNA-RNA, modified nucleic acids-DNA or RNA, aptamer-aptamer. In addition, nucleic acids that possess a mutation can be distinguished from wildtype forms.

Nucleic acid targets can be any type of nucleic acid including, without limitation, DNA, RNA, LNA, PNA, genomic DNA, viral DNA, synthetic DNA, DNA with modified bases or backbone, mRNA, noncoding RNA, PIWI RNA, termini-associated RNA, promoter-associated RNA, tRNA, rRNA, microRNA, siRNA, post-transcriptionally modified RNA, synthetic RNA, RNA with modified bases or backbone, viral RNA, bacteria RNA, RNA aptamers, DNA aptamers, ribozymes, and DNAzymes.

Lipid targets include, without limitation, phospholipids, glycolipids, mono-, di-, tri-glycerides, sterols, fatty acyl lipids, glycerolipids, glycerophospholipids, sphingolipids, sterol lipids, prenol lipids, saccharolipids, polyketides, eicosanoids, prostaglandins, leukotrienes, thromboxanes, N-acyl ethanolamine lipids, cannabinoids, anandamides, terpenes, and lipopolysaccharides.

Small molecule targets include, without limitation, carbohydrates, monosaccharides, polysaccharides, galactose, fructose, glucose, amino acids, peptides, nucleic acids, nucleotides, nucleosides, cyclic nucleotides, polynucleotides, vitamins, drugs, inhibitors, single atom ions (such as magnesium, potassium, sodium, zinc, cobalt, lead, cadmium, etc.), multiple atom ions (such as phosphate), radicals (such as oxygen or hydrogen peroxide), and carbon-based gases (carbon dioxide, carbon monoxide, etc.).

Targets can also be whole cells or molecules expressed on the surface of whole cells. Exemplary cells include, without limitation, cancer cells, bacterial cells, or normal cells. Targets can also be viral particles.

A number of aptamers for these classes of target biomolecules have been identified previously, and can be incorporated into the multivalent nucleic acid aptamer constructs of the present invention. For example, other known RNA aptamers include, without limitation, RNA ligands of T4 DNA polymerase, RNA ligands of HIV reverse transcriptase, RNA ligands of bacteriophage R17 coat protein, RNA ligands for nerve growth factor, RNA ligands of HSV-1 DNA polymerase, RNA ligands of *Escherichia coli* ribosomal protein S1, and RNA ligands of HIV-1 Rev protein (U.S. Pat. No. 5,270,163 to Gold et al., which is hereby incorporated by reference in its entirety); RNA ligands of *Bacillus subtilis* ribonuclease P (U.S. Pat. No. 5,792,613 to Schmidt et al., which is hereby incorporated by reference); RNA ligands of ATP and RNA ligands of biotin (U.S. Pat. No. 5,688,670 to Szostak et al., which is hereby incorporated by reference in its entirety); RNA ligands of prion protein (Weiss et al., "RNA Aptamers Specifically Interact with the Prion Protein PrP," *J. Virol.* 71(11):8790-8797 (1997), which is hereby incorporated by reference in its entirety); RNA ligands of hepatitis C virus protein NS3 (Kumar et al., "Isolation of RNA Aptamers Specific to the NS3 Protein of Hepatitis C Virus from a Pool of Completely Random RNA," *Virol.* 237(2):270-282 (1997); Urvil et al., "Selection of RNA Aptamers that Bind Specifically to the NS3 Protein of Hepatitis C Virus," *Eur. J. Biochem.* 248(1): 130-138 (1997); Fukuda et al., "Specific RNA Aptamers to NS3 Protease Domain of Hepatitis C Virus," *Nucleic Acids Symp. Ser.* 37:237-238 (1997), each of which is hereby incorporated by reference in its entirety); RNA ligands of chloramphenicol (Burke et al., "RNA Aptamers to the Peptidyl Transferase Inhibitor Chloramphenicol," *Chem. Biol.* 4(11):833-843 (1997), which is hereby incorporated by reference in its entirety); RNA ligands of the adenosine moiety of S-adenosyl methionine (Burke and Gold, "RNA Aptamers to the Adenosine Moiety of S-Adenosyl Methionine: Structural Inferences from Variations on a Theme and the Reproducibility of SELEX," *Nucleic Acids Res.* 25(10): 2020-2024 (1997), which is hereby incorporated by reference in its entirety); RNA ligands of protein kinase C (Conrad et al., "Isozyme-Specific Inhibition of Protein Kinase C by RNA Aptamers," *J. Biol. Chem.* 269(51): 32051-32054 (1994); Conrad and Ellington, "Detecting Immobilized Protein Kinase C Isozymes with RNA Aptamers," *Anal. Biochem.* 242(2):261-265 (1996), each which is hereby incorporated by reference in its entirety); RNA ligands of subtilisin (Takeno et al., "RNA Aptamers of a Protease Subtilisin," *Nucleic Acids Symp. Ser.* 37:249-250 (1997), which is hereby incorporated by reference in its entirety); RNA ligands of yeast RNA polymerase II (Thomas et al., "Selective Targeting and Inhibition of Yeast RNA Polymerase II by RNA Aptamers," *J. Biol. Chem.* 272(44): 27980-27986 (1997), which is hereby incorporated by reference in its entirety); RNA ligands of human activated protein C (Gal et al., "Selection of a RNA Aptamer that Binds to Human Activated Protein C and Inhibits its Protein Function," *Eur. J. Biochem.* 252(3):553-562 (1998), which is hereby incorporated by reference in its entirety); and RNA ligands of cyanocobalamin (Lorsch and Szostak, "In vitro Selection of RNA Aptamers Specific for Cyanocobalamin," *Biochem.* 33(4):973-982 (1994), which is hereby incorporated by reference in its entirety). Additional RNA aptamers are continually being identified and isolated by those of ordinary skill in the art, and these, too, can be incorporated into the multivalent aptamer constructs of the present invention.

According to one embodiment, the multivalent nucleic acid aptamer molecules of the invention include a first domain that binds to the fluorophore substantially only after the second domain binds to the target molecule. As demonstrated in the examples, in multivalent nucleic acid aptamer molecules of this type, the second domain possesses a stable structure and is capable of binding to the target molecule, whereas the first domain or regions of the nucleic acid molecule adjacent to the first domain possess a structure that is substantially incapable of binding the fluorophore (or does so with reduced affinity). Upon binding of the target molecule by the second domain, however, the secondary structure of the first domain is altered and adopts a structure that is capable of binding the fluorophore with sufficiently high affinity. As a consequence of target molecule binding, the fluorophore becomes bound by the first domain and upon exposure to radiation of appropriate wavelength emits a fluorescent emission signal. Multivalent aptamers of this type can be used as "turn-on" sensors.

As demonstrated in the accompanying examples, multivalent aptamer sensors of this embodiment have been developed that are specific for the biomolecules ATP, adenosine, cGMP, biotin, and nicotinamide adenine dinucleotide ("NAD"). The NAD and biotin sensors were developed using de novo sensor screening via SELEX, and the resulting SELEX products including a pool of biotin-specific sensors and a pool of NAD-specific sensors. Individual clone members from the SELEX pools represent alternative sensor constructs that are biotin-specific or NAD-specific "turn on" sensors. A number of aptamers that are specific for other biomolecules (including those identified above) can be introduced into the multivalent aptamer sensors of the present invention.

An exemplary ATP "turn-on" sensor has the nucleotide sequence according to SEQ ID NO: 31 as follows:

GGGAGACGCAACUGAAUGAACCUGUAGAACGACUUGGUCGGGUCAGUGUG

UGGGGAGAUCUACGGAUCUCAGGGCUGUUACGGGAGCUACAUGGAAGGAG

UCCAUGUGUCGUAUGCUUCGAGAAUAGAGUGUGGGGUCGUAUCCGCGUAA

CUAGUCGCGUCAC

Another exemplary adenosine "turn-on" sensor has the nucleotide sequence according to SEQ ID NO: 32 as follows:

CGCAACUGAAUGAACCUGUAGAACGACUUGGUCGGGUCAGCUGCGGAAGA

AACUGUGGCACUUCGGUGCCAGGGUAGCUUCGAGAAUAGAGUGUGGGGUCG

UAUCCGUAACCAGUUGCG

The bold sequences of the sensor represent the J2 stem that links the adenosine aptamer to the DFHBI aptamer 24-1. The J2 stem, as demonstrated in the Example 22, can be replaced with other stems.

An exemplary cGMP "turn-on" sensor has the nucleotide sequence according to SEQ ID NO: 33 as follows:

GGGAGACGCAACUGAAUGAACCUGUAGAACGACUUGGUCGGGUCAGCCCU

GCGAUGCAGAAAGGUGCUGACGACACAUCUUCGAGAAUAGAGUGUGGGGU

CGUAUCCGCGUAACUAGUCGCGUCAC

According to another embodiment, the multivalent nucleic acid aptamer molecule of the invention includes a first domain that binds to the fluorophore substantially only in the absence of the second domain binding to the target molecule. In multivalent nucleic acid aptamer molecules of this type, the second domain possesses a stable structure and is capable of binding to the target molecule, and the first domain or regions of the nucleic acid molecule adjacent to the first domain possess a structure that is capable of binding the fluorophore with sufficiently high affinity. Upon binding of the target molecule by the second domain, however, the secondary structure of the first domain is altered and adopts a structure that is substantially incapable of binding the fluorophore with high affinity. As a consequence of target molecule binding, the fluorophore dissociates from the first domain and despite exposure to radiation of appropriate wavelength the fluorophore will no longer emit a fluorescent emission signal (or emits only a substantially diminished level of fluorescent emissions). Multivalent aptamers of this type can be used as "turn-off" sensors.

As discussed below, the monovalent and multivalent aptamers of the invention can be used as sensors for tracking the presence, location, or quantity of a fused nucleic acid molecule of interest in a cell or an in vitro sample; for determining the presence, location, or quantity of a target molecule of interest in a cell or an in vitro sample; for high throughput drug screening to assess the ability of a drug to modulate certain cellular functions, such as transcription levels or splicing, or for modulating the activity or availability of a target molecule; for microarray detection of analytes or genes of interest; and de novo screening of sensor molecules for particular targets of interest using a modified SELEX.

Figure 27:
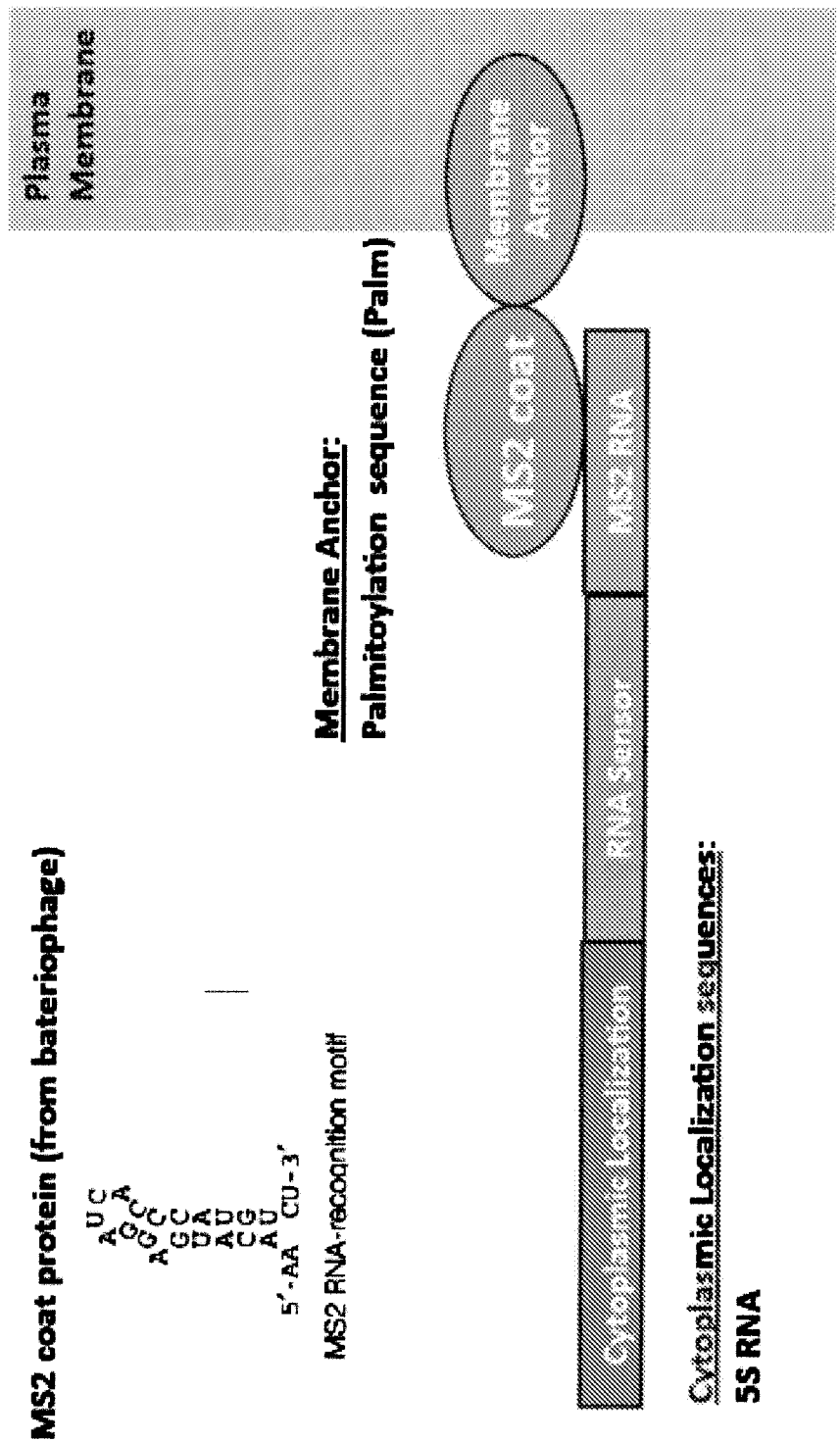
FIG. 27 illustrates a scheme for immobilizing fluorescent RNAs on membranes to perform live cell TIRF microscopy.

The nucleic acid aptamer molecules of the present invention can also be directed to specific cellular locations by fusing created a nucleic acid fusion with a particular signaling molecule or signal-interacting molecule. This is exemplified in FIG. 27 and the accompanying examples.

According to another embodiment, a multivalent nucleic acid aptamer construct of the invention includes one or more first domains that bind specifically to multiple identical fluorophore compounds per molecule, and a second domain that includes a random nucleotide sequence. By "random," it is contemplated that the entirety of the second domain, or merely a portion thereof, contains a nucleotide sequence that is not known a priori, but rather is generated randomly. Thus, a portion of the second domain may contain a known sequence, but the entirety of the second domain sequence is not known. Multivalent aptamer constructs of this type are prepared as "turn-on" sensors, as described above, and are useful for de novo screening and identification of aptamers having affinity for a target molecule of interest. These multivalent nucleic acid aptamer constructs can be generated during a modified SELEX process as described hereinafter. Thus, the present invention also encompasses a library of these multivalent nucleic acid aptamer constructs. In the library, each member of the initial library preferably contains a unique or substantially unique random sequence (i.e., shared by few, if any, other initial library members).

Molecular Complexes

A further aspect of the invention relates to molecular complexes that are formed using the fluorescent compounds and nucleic acid aptamers of the present invention, which are specifically bound to the fluorescent compounds such that the fluorophore has substantially enhanced fluorescence (i.e., in comparison to the fluorophore prior to specific binding) upon exposure to radiation of suitable wavelength.

According to one embodiment, the nucleic acid molecule includes one or more first domains, as described above, and the molecular complex is therefore formed by the nucleic acid molecule and one or more fluorescent compounds that are bound to at least one, and optionally all, of the first domains present in the nucleic acid molecule. These molecular complexes can exist in vitro, in isolated form, or in vivo following introduction of the nucleic acid molecule (or a genetic construction or expression system encoding the same) into a host cell.

According to another embodiment, the nucleic acid molecule is multivalent and includes one or more first domains and a second domain that binds specifically to a target molecule of interest. The molecular complex, therefore, can include the nucleic acid molecule, the target molecule (bound specifically by the second domain), and one or more fluorescent compounds that are bound to the first domain(s). These molecular complexes can exist in vitro, in isolated form, or in vivo following introduction of the nucleic acid molecule (or a genetic construction or expression system encoding the same) into a host cell.

According to another embodiment, the nucleic acid molecule is multivalent and includes a plurality of aptamer sensor concatemers, each monomer including a first domain and a second domain. The molecular complex, therefore, can include the nucleic acid molecule, a plurality of target molecules (bound specifically by the plurality of second domains), and a plurality of fluorescent compounds that are bound to the plurality of first domain(s). These molecular complexes can exist in vitro, in isolated form, or in vivo following introduction of the nucleic acid molecule (or a genetic construction or expression system encoding the same) into a host cell.

Specific examples of both of these types of molecular complexes, formed in vitro and in vivo, are disclosed in the accompanying Examples. Although in vivo host cells are described in the accompanying Examples, it should be appreciated to skilled artisans that the host cells can be present in a whole organism, preferably a non-human organism.

For formation of the molecular complex inside a cell, the fluorophore is introduced into the cell where it can interact with (and be bound by) the aptamer that specifically binds to it. According to one approach, the cell or the sample is contacted with the fluorophore by incubating the cell or the sample with the fluorophore. The fluorophore will be taken up by the cell, where it may freely diffuse throughout the cell. According to another approach, the fluorophore is injected into the cell or administered to a plant, embryo, mammal, or transgenic animal including the cell.

Genetic Constructs

The RNA aptamer molecules of the present invention can be prepared either in vitro or in vivo using recombinant constructs, including transgenes, that encode the RNA aptamer molecules of the present invention. Whether using in vitro transcription or transgenes suitable for expression in vivo, these genetic constructs can be prepared using well known recombinant techniques.

A further aspect of the present invention relates to a constructed DNA molecule that includes a first region encoding an RNA aptamer molecule of the invention.

According to one embodiment, the constructed DNA molecule encodes an RNA fusion product. Such a product is formed by joining together one piece of DNA encoding an RNA molecule of interest and a second piece of DNA encoding an RNA aptamer molecule that binds specifically to a fluorophore of the invention. As described above, the RNA aptamer molecule can include a concatemer of fluorophore-binding domains.

According to another embodiment, the constructed DNA molecule encodes a molecular sensor of the invention, which is formed by joining together one piece of DNA encoding an RNA aptamer molecule that is specific for a target molecule and a second piece of DNA encoding an RNA aptamer molecule that binds specifically to a fluorophore of the invention. The conjoined RNA sequences can cooperate in the manner described above, so as to achieve a "turn-on" sensor or "turn-off" sensor.

According to yet another embodiment, an empty construct can be prepared for preparation of an RNA fusion product. Such an empty construct includes piece of DNA encoding an RNA aptamer molecule that binds specifically to a fluorophore of the invention, along with appropriate regulatory sequences (discussed below), and a restriction enzyme insertion site that can be used for subsequent insertion of a desired DNA molecule (encoding an RNA molecule of interest). As described above, the RNA aptamer molecule can include a concatemer of fluorophore-binding domains. The restriction enzyme insertion site can include one or more enzymatic cleavage sites to facilitate insertion of virtually any DNA coding sequence as desired. The restriction enzyme insertion site is preferably located between the promoter sequence and the aptamer-encoding DNA sequence.

According to further embodiment, the constructed DNA molecule encodes an RNA aptamer of the invention, however, within the region encoding the RNA aptamer, an intron is positioned therein. This spatially segregates the RNA aptamer-encoding regions, whereby transcription in the absence of a proper spliceosome will not afford a functional aptamer molecule. In the presence of a proper spliceosome, excision of the intron from a transcript of the constructed DNA molecule affords the RNA aptamer molecule of the invention.

Preparation of the DNA molecule can be carried out by well-known methods of DNA ligation. DNA ligation utilizes DNA ligase enzymes to covalently link or ligate fragments of DNA together by catalyzing formation of a phosphodiester bond between the 5' phosphate of one strand of DNA and the 3' hydroxyl of another. Typically, ligation reactions require a strong reducing environment and ATP. The commonly used T4 DNA ligase is an exemplary DNA ligase in preparing the DNA molecule of the present invention. Once the DNA molecule of the present invention has been constructed, it can be incorporated into host cells as described infra.

Transcription of the DNA molecule of the present invention is dependent upon the presence of a promoter, which is a DNA sequence that directs the binding of RNA polymerase and thereby promotes RNA synthesis. Accordingly, the DNA molecule of the present invention may include a promoter operably coupled to the first region to control expression of the RNA aptamer.

The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). It is desirable to use strong promoters in order to obtain a high level of transcription. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the coding sequence of the DNA molecule. Depending upon the desired activity, it is possible to select the promoter for not only in vitro production of the RNA aptamer, but also in vivo production in cultured cells or whole organisms, as described below. Because in vivo production can be regulated genetically, a preferable type of promoter is an inducible promoter which induces transcription of the DNA molecule in response to specific conditions, thereby enabling expression of the RNA aptamer as desired (i.e., expression within specific tissues, or at specific temporal and/or developmental stages).

Preferred promoters for use with the constructed DNA molecule of the present invention include a T7 promoter, a SUP4 tRNA promoter, an RPR1 promoter, a GPD promoter, a GAL1 promoter, an hsp70 promoter, an Mtn promoter, a UAShs promoter, and functional fragments thereof. The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the molecular complex of the present invention (Milligan et al., "Oligoribonucleotide Synthesis Using T7 RNA Polymerase and Synthetic DNA Templates," *Nucleic Acids Res.* 15(21):8783-8798 (1987), which is hereby incorporated by reference in its entirety). The SUP4 tRNA promoter and RPR1 promoter are driven by RNA polymerase III of the yeast *Saccharomyces cerevisiae*, and suitable for high level expression of RNA less than 400 nucleotides in length (Kurjan et al., Mutation at the Yeast SUP4 tRNA$^{tyr}$ Locus: DNA Sequence Changes in Mutants Lacking Suppressor Activity," *Cell* 20:701-709 (1980); Lee et al., "Expression of RNase P RNA in *Saccharomyces cerevisiae* is Controlled by an Unusual RNA Polymerase III Promoter," *Proc. Natl. Acad. Sci. USA* 88:6986-6990 (1991), each of which is hereby incorporated by reference in its entirety). The glyceraldehyde-3-phosphate dehydrogenase (GPD) promoter in yeast is a strong constitutive promoter driven by RNA polymerase II (Bitter et al., "Expression of Heterologous Genes in *Saccharomyces cerevisiae* from Vectors Utilizing the Glyceraldehyde-3-phosphate Dehydrogenase Gene Promoter," *Gene* 32:263-274 (1984), which is hereby incorporated by reference in its entirety). The galactokinase (GAL1) promoter in yeast is a highly inducible promoter driven by RNA polymerase II (Johnston and Davis, "Sequences that Regulate the Divergent GAL1-GAL10 Promoter in *Saccharomyces cerevisiae*," *Mol. Cell. Biol.* 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," *Proc. Natl. Acad. Sci. USA* 81:7318-7322 (1984), which is hereby incorporated by reference in its entirety).

Initiation of transcription in mammalian cells requires a suitable promoter, which may include, without limitation, β-globin, GAPDH, β-actin, actin, Cstf2t, SV40, MMTV, metallothionine-1, adenovirus E1a, CMV immediate early, immunoglobulin heavy chain promoter and enhancer, and RSV-LTR. Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Spatial control of an RNA molecule can be achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the molecular complex of the present invention, providing a means to restrict the expression of the molecular complex in particular tissues. Any of a variety of tissue-specific promoters can be selected as desired.

For gene expression in plant cells, suitable promoters may include, without limitation, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (See Vallejos, et al., "Localization in the Tomato Genome of DNA Restriction Fragments Containing Sequences Homologous to the rRNA (45S), the major chlorophyll$_{A/B}$ Binding Polypeptide and the Ribulose Bisphosphate Carboxylase Genes," *Genetics* 112: 93-105 (1986) (disclosing the small subunit materials), which is hereby incorporated by reference in its entirety). The nos promoter and the 35S promoter of cauliflower mosaic virus are well known in the art.

In addition, the constructed DNA molecule may also include an operable 3' regulatory region, selected from among those which are capable of providing correct transcription termination and polyadenylation of mRNA for expression in plant cells. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l. Acad. Sci. USA*, 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature,* 313(6005):810-812 (1985), which is hereby incorporated by reference in its entirety). Virtually any 3' regulatory region known to be operable in plants would suffice for proper expression of the coding sequence of the constructed DNA molecule of the present invention.

Once the DNA molecule of the present invention has been constructed, it can be incorporated into cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for their persistent existence inside cells and for the transcription of an RNA molecule that can be translated into the molecular complex of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/- or KS +/- (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology*, vol. 185 (1990), which is hereby incorporated by reference in its entirety), pIIIEx426 RPR, pIIIEx426 tRNA (see Good and Engelke, "Yeast Expression Vectors Using RNA Polymerase III Promoters," *Gene* 151:209-214 (1994), which is hereby incorporated by reference in its entirety), p426GPD (see Mumberg et al., "Yeast Vectors for the Controlled Expression of Heterologous Proteins in Different Genetic Background," *Gene* 156:119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," *Nucl. Acids Res.* 22:5767-5768 (1994), which is hereby incorporated by reference in its entirety), pUAST (see Brand and Perrimon, "Targeted Gene Expression as a Means of Altering Cell Fates and Generating Dominant Phenotypes," *Development* 118:401-415 (1993), which is hereby incorporated by reference in its entirety), and any derivatives thereof. Suitable vectors are continually being developed and identified.

A variety of host-vector systems may be utilized to express the DNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retrovial vectors, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Once the constructed DNA molecule has been cloned into an expression system, it is ready to be incorporated into a host cell. Such incorporation can be carried out by the various forms of transformation, depending upon the vector/host cell system such as transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety. Suitable host cells include, but are not limited to, bacteria, yeast, mammalian cells, insect cells, plant cells, and the like. The host cell is preferably present either in a cell culture (ex vivo) or in a whole living organism (in vivo).

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1 cells, and primary cells recovered directly from a mammalian organism. With regard to primary cells recovered from a mammalian organism, these cells can optionally be reintroduced into the mammal from which they were harvested.

The expression of high levels of functional RNA aptamers within cells can be complicated by several factors including RNA stability, short half-life, and difficulties in cellular targeting. Nonetheless, substantial progress has been achieved over the last several years. The first demonstration of aptamer function in live cells involved nuclear targets (Klug et al., "In Vitro and In Vivo Characterization of Novel mRNA Motifs that Bind Special Elongation Factor SelB," *Proc. Natl. Acad. Sci. USA* 94:6676-6681 (1997); Shi et al., "RNA Aptamers as Effective Protein Antagonists In a Multicellular Organism," *Proc. Natl. Acad. Sci. USA* 96:10033-10038 (1999); Thomas et al., "Selective Targeting and Inhibition of Yeast RNA Polymerase II by RNA Aptamers," *J. Biol. Chem.* 272: 27980-27986 (1997), which are hereby incorporated by reference in their entirety). Aptamer function within the nucleus of mammalian cells has also been demonstrated (Symensma et al., "Polyvalent Rev Decoys Act as Artificial Rev-Responsive Elements," *J. Virol.* 73:4341-4349 (1999), which is hereby incorporated by reference in its entirety). More recently, effective strategies for cytoplasmic targeting of aptamer have also been developed. For example, the human tRNA initiator sequence, which mediates highly efficient nuclear export to deliver functional chimeric RNA aptamers to the cytosol has been used (Chaloin et al., "Endogenous Expression of a High-Affinity Pseudoknot RNA Aptamer Suppresses Replication of HIV-1," *Nucl. Acids Res.* 30:4001-4008 (2002), which is hereby incorporated by reference in its entirety). Functional RNA aptamers have also been directly delivered to the cytoplasm by lipofection (Theis et al., "Discriminatory Aptamer Reveals Serum Response Element Transcription Regulated by Cytohesin-2," *Proc. Natl. Acad. Sci. USA* 101:11221-11226 (2004), which is hereby incorporated by reference in its entirety). Finally, most recently, very high levels of aptamer expression ($1 \times 10^7$ molecules per cell) have been achieved by fusion with a highly stable transcript (Choi et al., "Intracellular Expression of the T-cell Factor-1 RNA Aptamer as an Intramer," *Mol. Cancer Ther.* 5:2428-2434 (2006), which is hereby incorporated by reference in its entirety).

Plant tissues suitable for transformation include leaf tissue, root tissue, meristems, zygotic and somatic embryos, and anthers. It is particularly preferred to utilize embryos obtained from anther cultures. The expression system of the present invention can be used to transform virtually any plant tissue under suitable conditions, and the transformed cells can be regenerated into whole plants.

One approach to transforming plant cells and/or plant cell cultures, tissues, suspensions, etc. with a DNA molecule of the present invention is particle bombardment (also known as biolistic transformation) of the host cell. This technique is disclosed in U.S. Pat. Nos. 4,945,050, 5,036,006, and 5,100,792, all to Sanford, et al., which are hereby incorporated by reference in their entirety. Another method of introducing DNA molecules into a host cell is fusion of protoplasts with other entities, either minicells, cells, lysosomes, or other fusible lipid-surfaced bodies that contain the DNA molecule (Fraley et al., "Expression of Bacterial Genes in Plant Cells," *Proc. Natl. Acad. Sci. USA* 80:4803-4807 (1983), which is hereby incorporated by reference in its entirety). The DNA molecule of the present invention may also be introduced into the plant cells and/or plant cell cultures, tissues, suspensions, etc. by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety).

In producing transgenic plants, the DNA construct in a vector described above can be microinjected directly into plant cells by use of micropipettes to transfer mechanically the recombinant DNA (Crossway, "Integration of Foreign DNA Following Microinjection of Tobacco Mesophyll Protoplasts," *Mol. Gen. Genetics* 202:179-85 (1985), which is hereby incorporated by reference in its entirety). The genetic material may also be transferred into the plant cell using polyethylene glycol (Krens et al., "In Vitro Transformation of Plant Protoplasts with Ti-Plasmid DNA," *Nature* 296:72-74 (1982), which is hereby incorporated by reference in its entirety). Alternatively, genetic sequences can be introduced into appropriate plant cells by means of the Ti plasmid of *A. tumefaciens* or the Ri plasmid of *A. rhizogenes*, which is transmitted to plant cells on infection by *Agrobacterium* and is stably integrated into the plant genome (Schell, "Transgenic Plants as Tools to Study the Molecular Organization of Plant Genes," *Science* 237:1176-83 (1987), which is hereby incorporated by reference in its entirety). After transformation, the transformed plant cells must be regenerated, and this can be accomplished using well known techniques as described in Evans et al., *Handbook of Plant Cell Cultures, Vol.* 1, MacMillan Publishing Co., New York (1983); and Vasil (ed.), *Cell Culture and Somatic Cell Genetics of Plants*, Acad. Press, Orlando, Vol. I (1984) and Vol. III (1986), each of which is hereby incorporated by reference in its entirety.

Methods of Use

In the various methods of use, the formation of molecular complexes of the invention (e.g., fluorophore:aptamer complexes or fluorophore:aptamer:target complexes) can be identified, quantified, and monitored for various purposes, as discussed more fully below. Detection of molecular complex formation, through the fluorescent output of the fluorophore or a FRET partner (e.g., donor or acceptor), can be used to detect complex formation in a cell-free sample (e.g., cell extracts or lysates), tissues or tissue extracts, bodily fluids, serum, blood and blood products, environmental samples, or in whole cells.

Regardless of the intended use, a suitable radiation source is used to illuminate the fluorophore after exposing the fluorophore and aptamer to one another. The radiation source can be used alone or with optical fibers and any optical waveguide to illuminate the sample. Suitable radiation sources include, without limitation, filtered, wide-spectrum light sources (e.g., tungsten, or xenon arc), laser light sources, such as gas lasers, solid state crystal lasers, semiconductor diode lasers (including multiple quantum well, distributed feedback, and vertical cavity surface emitting lasers), dye lasers, metallic vapor lasers, free electron lasers, and lasers using any other substance as a gain medium. Common gas lasers include Argon-ion, Krypton-ion, and mixed gas (e.g., Ar Kr) ion lasers, emitting at 455, 458, 466, 476, 488, 496, 502, 514, and 528 nm (Ar ion); and 406, 413, 415, 468, 476, 482, 520, 531, 568, 647, and 676 nm (Kr ion). Also included in gas lasers are Helium Neon lasers emitting at 543, 594, 612, and 633 nm. Typical output lines from solid state crystal lasers include 532 nm (doubled Nd:YAG) and 408/816 nm (doubled/primary from Ti:Sapphire). Typical output lines from semiconductor diode lasers are 635, 650, 670, and 780 rnm. Infrared radiation sources can also be employed.

Excitation wavelengths and emission detection wavelengths will vary depending on both the fluorophore and the nucleic acid aptamer molecule that are being employed. As demonstrated in the accompanying Examples, several different aptamer molecules can differently affect the emission spectrum of a single fluorophore, affording very distinct emission patterns.

Detection of the emission spectra can be achieved using any suitable detection system. Exemplary detection systems include, without limitation, a cooled CCD camera, a cooled intensified CCD camera, a single-photon-counting detector (e.g., PMT or APD), dual-photon counting detector, spectrometer, fluorescence activated cell sorting (FACS) systems, fluorescence plate readers, fluorescence resonance energy transfer, and other methods that detect photons released upon fluorescence or other resonance energy transfer excitation of molecules.

In one embodiment, the detector is optically coupled to receive the output emissions of the fluorophore:aptamer complex through a lens system, such as in an optical microscope. In another embodiment, a fiber optic coupler is used, where the input to the optical fiber is placed in close proximity to the substrate surface of a biosensor, either above or below the substrate. In yet another embodiment, the optical fiber provides the substrate for the attachment of nucleic acid sensor molecules and the biosensor is an integral part of the optical fiber.

In one embodiment, the interior surface of a glass or plastic capillary tube provides the substrate for the attachment of the fluorophore or the nucleic acid sensor molecules. The capillary can be either circular or rectangular in cross-section, and of any dimension. The capillary section containing the biosensors can be integrated into a microfluidic liquid-handling system which can inject different wash, buffer, and analyte-containing solutions through the sensor tube. Spatial encoding of the fluorophore or nucleic acid sensor molecules can be accomplished by patterning them longitudinally along the axis of the tube, as well as radially, around the circumference of the tube interior. Excitation can be accomplished by coupling a laser source (e.g., using a shaped output beam, such as from a VCSEL) into the glass or plastic layer forming the capillary tube. The coupled excitation light will undergo TIR at the interior surface/ solution interface of the tube, thus selectively exciting fluorescently labeled biosensors attached to the tube walls, but not the bulk solution. In one embodiment, detection can be accomplished using a lens-coupled, or proximity-coupled large area segmented (pixelated) detector, such as a CCD. In a particular embodiment, a scanning (i.e., longitudinal/axial and azimuthal) microscope objective lens/emission filter combination is used to image the biosensor substrate onto a CCD detector. In a different embodiment, a high resolution CCD detector with an emission filter in front of it is placed in extremely close proximity to the capillary to allow direct imaging of the fluorophore:nucleic acid aptamer complexes. In a different embodiment, highly efficient detection is accomplished using a mirrored tubular cavity that is elliptical in cross-section. The sensor tube is placed along one focal axis of the cavity, while a side-window PMT is placed along the other focal axis with an emission filter in front of it. Any light emitted from the biosensor tube in any direction will be collected by the cavity and focused onto the window of the PMT.

In still another embodiment, the optical properties of a molecular complex are analyzed using a spectrometer (e.g., such as a luminescence spectrometer). The spectrometer can perform wavelength discrimination for excitation and detection using either monochromators (i.e., diffraction gratings), or wavelength bandpass filters. In this embodiment, the fluorophores of the molecular complexes are excited at absorption maxima appropriate to the fluorophore being used and fluorescence intensity is measured at emission wavelengths appropriate for the complexes being detected. Given that the intensity of the excitation light is much greater than that of the emitted fluorescence, even a small fraction of the excitation light being detected or amplified by the detection system will obscure a weak biosensor fluorescence emission signal. In one embodiment, the biosensor molecules are in solution and are pipetted (either manually or robotically) into a cuvette or a well in a microtiter plate within the spectrometer. In a further embodiment, the spectrometer is a multifunction plate reader capable of detecting optical changes in fluorescence or luminescence intensity (at one or more wavelengths), time-resolved fluorescence, fluorescence polarization (FP), absorbance (epi and transmitted), etc., such as the Fusion multifunction plate reader system (Packard Biosciences, Meriden, Conn.). Such a system can be used to detect optical changes in biosensors either in solution, bound to the surface of microwells in plates, or immobilized on the surface of solid substrate (e.g., a microarray on a glass substrate). This type of multiplate/ multisubstrate detection system, coupled with robotic liquid handling and sample manipulation, is particularly amenable to high-throughput, low-volume assay formats.

In embodiments where nucleic acid sensor molecules or fluorophores are attached to substrates, such as a glass slide or in microarray format, it is desirable to reject any stray or background light in order to permit the detection of low intensity fluorescence signals. In one embodiment, a small sample volume (about 10 nl) is probed to obtain spatial discrimination by using an appropriate optical configuration, such as evanescent excitation or confocal imaging. Furthermore, background light can be minimized by the use of narrow-bandpass wavelength filters between the sample and the detector and by using opaque shielding to remove any ambient light from the measurement system.

In one embodiment, spatial discrimination of a molecular complex of the invention (fluorophore:nucleic acid aptamer complexes or fluorophore:nucleic acid aptamer:target molecule complexes) attached to a substrate in a direction normal to the interface of the substrate is obtained by evanescent wave excitation. This is illustrated in FIG. 25A. Evanescent wave excitation utilizes electromagnetic energy that propagates into the lower-index of refraction medium when an electromagnetic wave is totally internally reflected at the interface between higher and lower-refractive index materials. In this embodiment a collimated laser beam is incident on the substrate/solution interface (at which the fluorophore:nucleic acid aptamer complexes or fluorophore:nucleic acid aptamer:target molecule complexes are immobilized) at an angle greater than the critical angle for total internal reflection (TIR). This can be accomplished by directing light into a suitably shaped prism or an optical fiber. In the case of a prism, as shown in FIG. 25A, the substrate is optically coupled (via index-matching fluid) to the upper surface of the prism, such that TIR occurs at the substrate/solution interface on which the molecular complexes are immobilized. Using this method, excitation can be localized to within a few hundred nanometers of the substrate/solution interface, thus eliminating autofluorescence background from the bulk analyte solution, optics, or substrate. Target recognition is detected by a change in the fluorescent emission of the molecular complex, whether a change in intensity or polarization. Spatial discrimination in the plane of the interface (i.e., laterally) is achieved by the optical system.

In the embodiment shown in FIG. 25A, a TIRF evanescent wave excitation optical configuration is implemented using a detection system that includes a universal fluorescence microscope. Any fluorescent microscope compatible with TIRF can be employed The TIRF excitation light or laser can be set at either an angle above the sample shining down on the sample (as in FIG. 25), or at an angle through the objective shining up at the sample. Effective results have been obtained with immobilization of either the aptamer or the fluorophore using NHS-activated glass slides. The fluorophore containing a free amine (at the $R_1$ position) can be used to react with the NHS-slide. RNA can be modified with a 5' amine for NHS reactions by carrying out T7 synthesis in the presence of an amine modified GTP analog (commercially available).

In the several embodiments described above, the output of the detection system is preferably coupled to a processor for processing optical signals detected by the detector. The processor can be in the form of personal computer, which contains an input/output (I/O) card coupled through a data bus into the processor. CPU/processor receives and processes the digital output signal, and can be coupled to a memory for storage of detected output signals. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a software package (for image processing) for carrying out one or more aspects of the present invention as described herein.

In addition to their specificity in binding to fluorophores, a number of the aptamers have demonstrated that their affinity for the target fluorophore can be modulated by environmental conditions.

According to one embodiment, the affinity of the aptamer for the fluorophore is partially or entirely ion dependent, i.e., any mono or divalent ion. The examples demonstrate aptamers that are responsive to $Mg^{2+}$ or $K^+$. Others have identified aptamers that bind specifically to other ions, and can be incorporated into the sensors of the present invention. These include, without limitation, aptamers specific to zinc (Rajendran et al., "Selection of Fluorescent Aptamer Beacons that Light Up in the Presence of Zinc," *Anal. Bioanal. Chem.* 390(4):1067-1075 (2008), which is hereby incorporated by reference in its entirety), cobalt (Breaker et al., "Engineered Allosteric Ribozymes as Biosensor Components," *Curr. Op. in Biotech* 13(1):31-39 (2002), which is hereby incorporated by reference in its entirety), and lead (Brown et al., "A Lead-dependent DNAzyme with a Two-step Mechanism," *Biochem.* 42(23):7152-7161 (2003), which is hereby incorporated by reference in its entirety).

According to another embodiment, the affinity of the aptamer for the fluorophore is temperature dependent. Thus, a titration exists where at very high temperatures, no binding will occur, but at lower temperatures the highest degree of binding will occur. Based on the profile of a particular aptamer-fluorophore pair, the temperature within a system can be determined based on the measured fluorescence output. Aptamers that possess this property can be used as a sensor (discussed below) to determine the temperature of the environment.

According to another embodiment, the affinity of the aptamer for the fluorophore is partially pH dependent. The aptamers are fairly stable near neutral pH, but at higher or lower pH, the folding of the aptamer or the interaction between fluorophore/aptamer is disrupted such that changes in fluorescence can be measured as the pH varied away from neutral. Aptamers that possess this property can be used as a sensor (discussed below) to determine the pH of the environment.

The multivalent aptamers having first and second domains can be used for detection of a target molecule in a medium or sample. This is carried out by exposing the nucleic acid aptamer molecule of the invention to a medium suspected to contain the target molecule under conditions effective to allow the second domain to bind specifically to the target molecule, if present, and also exposing the nucleic acid molecule and medium to a fluorophore of the invention under conditions effective to allow the first domain to bind specifically to the fluorophore after binding of the target molecule by the second domain, thereby inducing the fluorophore to adopt a conformation that exhibits enhanced fluorescent emissions. Detection of molecular complex formation is then achieved by exciting the fluorophore (or FRET partner) with radiation of appropriate wavelength and detecting fluorescence by the fluorophore (or FRET partner), whereby the detection of fluorescence emissions by the fluorophore indicates binding of the nucleic acid molecule to the target molecule and, hence, its presence.

This embodiment can be carried out in whole cells either by introducing the nucleic acid aptamer molecule into the whole cell, or by transforming the whole cell with a transgene encoding the nucleic acid aptamer molecule. The fluorophore can be introduced into the environment of the whole cell, where it is readily taken up. This embodiment can also be carried in a cell free environment. An image of the detection process can also be acquired or generated using the detection systems described above.

This aspect of the invention is particularly adaptable to a microarray format, where the nucleic acid aptamer molecules are tethered at discrete locations on a substrate surface, i.e., solid support. The solid support used to form the microarray surface can include, without limitation, glass, metal, and ceramic supports. Tethering of the nucleic acid aptamer molecules can be carried out using a 5' biotin to streptavidin-coated glass (ArrayIt, Inc). In these systems, fluorophore is in solution and is recruited to the glass surface after the target molecule binds the second domain of the surface-bound aptamer, thereby creating a fluorophore: aptamer:target complex that can be detected, e.g., using TIRF. The sensors can be spotted in an array format, i.e., an array of microspots, or configured in other shapes or designs on surfaces, so that the sensors are positioned in a spatially defined manner. This will allow one or a series of sensors that are specific to distinct target molecules to be assayed following contact with a mixture that contains one or more of the target molecules at known or unknown concentrations. The fluorescence intensity can be used to determine the concentrations if suitable solutions containing known amounts of target analytes are used to calibrate the fluorescence signals.

While microarrays for monitoring the transcriptome are commonplace and have revolutionized biology, similar approaches are not available to study the proteome. The system and method of the invention allow the production of a protein-sensing microarray. This novel platform for protein detection has the potential to dramatically speed up the analysis of proteins for innumerable applications. For example, these arrays can be used to assay a set of specific proteins, such as clinically relevant biomarkers, or large sections of the proteome, such as proteins of specific functional classes. Current microarray technologies that utilize a panel of antibodies requires labeling of the proteins in biological samples with fluorescent dyes, such as Cy5-NHS, in order for the protein to be detected after binding to the antibodies. This is problematic, because this labeling procedure may affect the epitope recognized by the antibody. In contrast, the sensor arrays of the present invention do not require target labeling because the sensor will only bind to the fluorophore (at its first domain) after that target molecule has been bound by its second domain. The microarray format of the present invention also overcomes a number of challenges that plagued antibody arrays due to: (1) the low cost of the aptamer sensor molecule; (2) the ease with which oligonucleotides can be coupled to microarray surfaces; (3) the ability to reliably synthesize homogeneous preparations of oligonucleotides, which is a challenge with antibodies; (4) the increased stability of oligonucleotides compared to antibodies; (5) the highly specific nature of aptamer-protein interactions, which typically involve large surfaces (Stoltenburg et al., "SELEX—A Revolutionary Method to Generate High-affinity Nucleic Acid Ligands," *Biomolecular Engineering* 24:381-403 (2007); Hermann and Patel, "Adaptive Recognition by Nucleic Acid Aptamers," *Science* 287:820-825 (2000), each of which is hereby incorporated by reference in its entirety) rather than short epitopes as with antibodies; and (6) the ease of sample preparation, as the fluorescent signaling obtained using these protein sensors does not require the sample processing step of fluorescent dye tagging. Instead, binding of the target protein to the sensor is sufficient to elicit a fluorescent signal (in the presence of the solution phase fluorophore), thereby dramatically simplifying the analysis of protein mixtures.

Thus, upon exposure to the target and fluorophore, the molecular complex will form and the fluorophore, upon illumination, will exhibit emissions patterns from the discrete location on the array surface. Using appropriate mapping software, the presence of the fluorescent emission signal will positively identify the target molecule as being present in the sample being queried. As noted above, quantification can be carried out if reliable calibration is performed.

A further aspect of the invention involves using a multivalent aptamer having first and second domains for determining the location of a target molecule, particularly within a whole cell. This aspect of the invention involves forming a molecular complex (fluorophore:aptamer:target molecule), exciting the fluorophore with light of an appropriate wavelength, and then detecting fluorescence by the fluorophore, whereby fluorescence by the fluorophore identifies presence of the target molecule. In whole cells, this embodiment can be carried out by introducing the nucleic acid aptamer molecule into the whole cell, or by transforming the whole cell with a transgene encoding the nucleic acid aptamer molecule. Once inside the cell, the nucleic acid aptamer molecule will bind specifically to the target molecule via its second domain. The fluorophore can be introduced into the environment of the whole cell, where it is readily taken up. An image of the detection process can also be acquired or generated using the detection systems described above.

A DNA construct encoding an RNA aptamer molecule can be used to measure the transcription by a promoter of interest in a cell. This can be carried out by introducing a DNA construct or transgene encoding the RNA aptamer molecule into a cell, introducing the fluorophore into the cell, and then determining whether the aptamer:fluorophore complex forms, as measured by the amount of fluorescence detected within the cell.

This aspect of the invention can be used to screen agents for their ability to modulate transcription of the DNA construct and, thus, native genes that contain the same promoter as the DNA construct. When screening an agent, the agent is introduced to the cell, preferably prior to introducing the fluorophore. After a suitable time delay (to allow for transcription of the nucleic acid aptamer to occur, the fluorophore can be introduced to the cell. The detection of an increase or decrease in fluorescence by the fluorophore:aptamer complex within the cell, relative to an otherwise identical but untreated control cell, indicates that the agent altered the level of transcription by the promoter.

In an alternative embodiment, the same DNA construct can be used in an in vitro detection procedure, whereby the a DNA construct and agent are both introduced into a cell but the fluorophore is not. Instead, RNA transcripts are first recovered from the cell (using known cell lysis and RNA collection procedures), and then the fluorophore is introduced to the recovered RNA transcripts. The fluorophore can be bound to a solid surface of a suitable detection device, such as TIRF system or other detectors of the type described above. The detection of an increase or decrease in fluorescence by the fluorophore:aptamer complex within the recovered RNA transcripts, relative to the RNA transcripts recovered from an otherwise identical but untreated control cell, indicates that the agent altered the level of transcription by the promoter.

A further aspect of the invention relates to the monitoring an RNA molecule within a cell. This aspect of the invention involves the use of a DNA construct of the invention that expresses an RNA fusion that includes an RNA aptamer of the invention joined to an RNA molecule of interest. After introducing the DNA construct into a cell and allowing for transcription to occur, the fluorophore of the invention can be introduced to the cell. This will allow the RNA aptamer portion of the RNA fusion molecule to bind specifically to the fluorophore (forming an aptamer:fluorophore complex) and enhance its fluorescence emissions. Detection of the RNA fusion molecule (including its location, its quantitation, or its degradation) can be carried out by exposing the cell to radiation of a wavelength suitable to induce fluorescence emissions by the fluorophore within the molecular complex; and then measuring the fluorescent emissions of the fluorophore or a FRET partner. The (sub)cellular location of the fluorescence emissions indicates the location of the transcript. Also, any decrease in the fluorescence emissions over time indicate degradation of the transcript. The latter can be confirmed by recovering RNA transcripts and measuring for the RNA fusion using, e.g., RT-PCR. Finally, the level of fluorescence correlates to the quantity of the RNA fusion molecule that is present.

In this embodiment, the RNA product to be monitoring can be any of a variety of RNA molecules having diverse functions. These include, without limitation, pre-mRNA, mRNA, pre-rRNA, rRNA, tRNA, hnRNA, snRNA, miRNA, or long noncoding RNA, PIWI RNA, termini-associated RNA, noncoding RNAs, promoter-associated RNAs, and viral RNAs.

To enhance the fluorescent signal, it is possible to tailor the number of fluorophores that can be bound to a single RNA transcript by using a concatemer of RNA aptamers.

In addition, this aspect of the invention is particularly adaptable to assessing the trafficking or degradation of multiple RNA molecules simultaneously. This is possible due to the tailored emission spectra of different aptamer:fluorophore complexes. Thus, this aspect can include introducing a second DNA construct into a cell, wherein the second DNA construct encoding a distinct RNA fusion molecule that includes an distinct RNA aptamer of the invention (or a concatemer thereof) joined to a distinct RNA transcript of interest. After introducing the DNA construct into the cell and allowing for transcription to occur, a second fluorophore of the invention can be introduced to the cell, i.e., one that is bound specifically by the aptamer present in the second RNA fusion molecule but not the first, and vice versa. This will allow the RNA aptamer portion of the transcript to bind specifically to the fluorophore (forming an aptamer:fluorophore complex) and enhance its fluorescence emissions. Detection of fluorescence can be carried out as described above. Simultaneous detection of separate emission peaks will allow for detecting localization or co-localization of both complexes.

A further aspect of the invention relates to monitoring a target molecule in a cell. This aspect of the invention can be carried out using a nucleic acid aptamer molecule that includes first and second domains, as described above, where the first domain binds specifically to the fluorophore only after the second domain binds specifically to the target molecule. Both the nucleic acid aptamer molecule and a fluorophore of the invention are introduced into a cell, allowing the fluorophore:aptamer:target complex to form in the presence of the target molecule and enhancing the fluorescence emissions by the fluorophore. Upon exposure of the cell to radiation of suitable wavelength to induce fluorescence emissions by the fluorophore that is bound in the complex or a FRET partner; and then measuring the fluorescent emissions of the fluorophore or FRET partner to monitor the target molecule. In this manner, the cellular location of the fluorescence emissions indicates the location of the target molecule, a decrease in the fluorescence emissions over time indicates degradation of the target molecule, and an increase in the fluorescence emissions over time indicates accumulation of the target molecule. Quantitation of the target molecule can be correlated to the level of fluorescence measured.

The target molecule in this aspect of the invention can be any protein, lipid, carbohydrate, hormone, cytokine, chemokine, metabolite, organic molecule, or metal ion, as described above.

This aspect of the invention can be carried by introducing the nucleic acid aptamer molecule directly into the cell or, alternatively, by introducing into the cell a gene that encodes the nucleic acid aptamer molecule.

Another aspect of the present invention relates to a method of screening a drug that modifies gene expression. This aspect can be carried out using a transgene that encodes an RNA aptamer molecule of the present invention. The transgene can be provided with a promoter of interest whose activity is being monitored with respect to the drug being screened. After introducing the transgene into a cell, the cell is exposed to the drug and a fluorophore of the invention, effectively introducing these compounds into the cell. Thereafter, the level of RNA aptamer transcription is measured by exposing the cell to radiation of a wavelength suitable to induce fluorescence emissions by the fluorophore that is bound by the RNA aptamer molecule or a FRET partner, and the fluorescent emissions of the fluorophore or FRET partner are measured, as described above. A reduction or absence of fluorescent emissions, relative to an otherwise identical control cell that is not exposed to the drug, indicates that the drug inhibits expression of the transgene. An increase of fluorescent emissions, relative to an otherwise identical control cell that is not exposed to the drug, indicates that the drug promotes expression of the transgene.

Another aspect of the present invention relates to a method of screening a drug that modifies RNA splicing. This aspect can be carried out using a transgene that encodes an RNA aptamer molecule of the present invention, wherein the RNA transcript of the transgene includes an intron that, with proper splicing, will result in a mature RNA molecule that is a functional fluorophore-binding RNA aptamer of the invention. This method is carried out by introducing the transgene into a cell and exposing the cell to a drug, and allowing transcription to occur such that both the immature transcript and the drug will both be present in the cell when splicing is to occur. A fluorophore of the invention is also introduced into the cell, whereby the mature RNA aptamer, if properly spliced, will be able to bind specifically to the fluorophore to enhance its fluorescence emissions. Detection of whether proper splicing occurred (or not) can be carried out by exposing the cell to radiation of a wavelength suitable to induce fluorescence emissions by the fluorophore (that is bound by the mature RNA aptamer molecule), or its FRET partner, and then measuring the fluorescent emissions of the fluorophore or FRET partner. A reduction or absence of fluorescent emissions, relative to an otherwise identical control cell that is not exposed to the drug, indicates that the drug inhibits proper splicing of the transcript. An increase of fluorescent emissions, relative to the otherwise identical control cell that is not exposed to the drug, indicates that the drug promotes proper splicing of the transcript.

This aspect of the invention can also be carried out in vitro. Basically, a medium is provided that contains the immature RNA transcript (with intron), a spliceosome including an appropriate splicing enzyme, a drug to be screened, and the fluorophore. As noted above, the immature RNA transcript includes first and second exons having an intervening intron region, and the first and second exons, upon excision of the intron, form an RNA aptamer molecule of the present invention. Upon exposing the medium to radiation of a wavelength suitable to induce fluorescence emissions by the fluorophore that is bound by the RNA aptamer molecule (or a FRET partner), any fluorescent emissions of the fluorophore (or FRET partner) are measured. A reduction or absence of fluorescent emissions, relative to an otherwise identical medium that lacks the drug, indicates that the drug inhibits proper splicing of the transcript. An increase of fluorescent emissions, relative to an otherwise identical medium that lacks the drug, indicates that the drug promotes proper splicing of the transcript.

Yet another aspect of the invention relates to a method of screening a drug for activity on a target molecule (i.e., either enhancing or diminishing activity of the target molecule). This process is carried out by introducing or expressing within a cell a nucleic acid molecule aptamer molecule of the present invention that includes first and second domains, as described above, where the first domain binds specifically to the fluorophore only after the second domain binds specifically to the target molecule. A fluorophore of the type described above is also introduced into the cell, where the fluorophore is bound specifically to the first domain of the nucleic acid molecule when the target molecule is bound by the second domain, thereby enhancing fluorescent emissions by the first fluorophore. Upon exposure of the cell to radiation of suitable wavelength to induce fluorescence emissions by the fluorophore that is bound in the complex or a FRET partner, and then measuring the fluorescent emissions of the fluorophore or FRET partner, it is possible to determine whether the activity of the target molecule is modified by the drug. Where a difference exists in the fluorescent emissions by the fluorophore or FRET partner, relative to an otherwise identical cell that lacks the drug, then this will indicates that the drug modifies the activity of the target molecule.

A further aspect of the invention relates to the de novo creation of aptamer-based sensor molecules for a particular target, without any prior knowledge of the aptamer for the particular target. This process is achieved using a modified SELEX procedure, where the nucleic acid molecules of the pool each contain a partially destabilized aptamer molecule that contains a first domain that binds specifically to a fluorophore of the present invention, and a second domain that comprises a wholly or partly random sequence. By partially destabilizing the first domain, only after binding of the second domain to the target molecule is first domain capable of binding specifically to the fluorophore. This is illustrated in FIG. 23A for the 24-1 aptamer, modified for use in a SELEX-based method for sensor development.

SELEX is carried out by exposing the pool of nucleic acid molecules to a target molecule and the fluorophore (whereby fluorescence emissions by the fluorophore are enhanced by the binding of the first domain to the fluorophore). Illuminating the fluorophore with light of a wavelength suitable to induce fluorescence emissions by the fluorophore that is bound by the first domain molecule, and measuring the fluorescent emissions of the fluorophore provide an indication as to whether any members of the pool bound to the target molecule (via their second domain).

RNAs members of the pool can be "precleared" by passing the RNAs over fluorophore-bound to agarose. This will remove all library members that retain constitutive fluorophoe-binding activity (i.e., even in the absence of a functional second domain that binds to the target). In the next step, the pool is exposed to the fluorophore-bound agarose, except that this time the target will be added to the incubation buffer. All washes will also contain target. After washing, the elution will occur in the same buffer, except that no target will be present. Thus, any RNAs whose binding to the fluorophore is dependent on target will elute. These RNAs will be recovered and used for subsequent rounds of SELEX to enrich for target-regulated sensors. The fluorescence of each pool will be tested as above in the presence of the fluorophore with or without the target of interest, and individual clones that exhibit target-dependent fluorescence can be isolated.

A negative selection can also be used to ensure that the sensors do not respond to structurally related molecules. To do this, the structurally related molecules can also be introduced in the elution buffer, so that if they promote fluorophore binding they will be retained on the agarose (whereas sensor constructs that are unaltered by these structurally related molecules will elute).

Kits

A further aspect of the present invention relates to various kits that can be used for practicing the present invention. The kit components can vary depending upon the intended use, and any reagents identified in this application can be included in the one or more kits. The kits can be packaged with components in separate containers or as mixtures, as noted below. Instructions for use may also be provided.

For example, according to one embodiment, the kit can include a single fluorophore of the invention and a plurality of nucleic acid aptamers or genetic constructs encoding those aptamers. The genetic construct can be designed for RNA trafficking studies, or for expression of multivalent sensor molecules. Regardless of the aptamer construction, the aptamer component that is responsible for binding to the fluorophore can be selected such that each of the plurality of nucleic acid aptamers causes a different emission profile by the fluorophore. In this way, a single fluorophore can be used for multiple, simultaneous detections.

According to this embodiment, the plurality of nucleic acid aptamers can be supplied separately, e.g., in different containers, or they can be supplied as a mixture or as a range of mixtures, such that each mixture is characterized by a different blended fluorescent emission pattern with the same fluorophore.

One example of this type of kit, as described in the accompanying examples, includes the fluorophore DMHBI and the aptamer products include at least the minimal aptamer sequences of at least two of the aptamers 23-11, 2-4, 17-3, 13-2, and 3-6, as well as mixtures thereof.

According to another embodiment, the kit can include one or more fluorophores that are immobilized on a substrate to allow for SELEX. The substrate can be an FTIR suitable flow cell.

According to another embodiment, the kit can include one or more nucleic acid aptamers that are immobilized on a surface of a substrate. The substrate can be provided with a plurality of the nucleic acid aptamers that are positioned at discrete locations so as to form an array. The spots on the array where the nucleic acid aptamers are retained can have any desired shape.

According to another embodiment, the kit can include a plurality of distinct fluorophores of the invention, and a plurality of distinct nucleic acid molecules of the invention which bind specifically to at least one of the plurality of fluorophores. Preferably, only a single monovalent or multivalent nucleic acid aptamer molecule is provided for each fluorophore. To enable their use together, each fluorophore: aptamer pair should be characterized by a distinct emission spectrum such that each can be detected independently. As demonstrated by the accompanying examples, a plurality of distinct aptamer/fluorophore complexes can achieve distinguishable emission spectra. The multiple colors will allow imaging of multiple RNAs simultaneously and allow the development of protein-RNA and RNA-RNA FRET systems.

For example, using multiple sensor molecules with distinct fluorophores that are compatible with FRET, detection of interactions of RNA or DNA with fluorescent proteins, RNAs, or other molecules can be achieved. FRET occurs if an appropriate acceptor fluorophore is sufficiently close to the acceptor fluorophore. Therefore, the interaction of a fluorescent protein, RNA, DNA, or other molecule with an RNA-fluorophore complex can be detected by measuring the FRET emission upon photoexcitation of the acceptor. Measurements like this can be used to measure the rate of binding of a fluorescent molecule to an RNA that is tagged with an RNA-fluorophore complex in both in vitro and in vivo settings. In a similar application, the RNA-fluorophore complex can serve as a donor and a fluorescent protein, RNA, DNA, other molecule can serve as the acceptor. In these cases, the RNA-fluorophore complex can be excited, and FRET emission can be detected to confirm an interaction. As used herein, a FRET partner refers to either a FRET acceptor or a FRET donor, which is used in combination with the fluorophore/aptamer complex of the present invention.

According to another embodiment, the kit can include an empty genetic construct of the invention, as described above, along with one or more of the following: one or more restriction enzymes, one or more fluorophore compounds of the invention (which are operable with the aptamer sequence encoded by the construct), and instructions for inserting a DNA molecule encoding an RNA molecule of interest into the restriction sites for formation of a genetic construct that encodes a transcript comprising the RNA molecule of interest joined to the RNA aptamer molecule.

EXAMPLES

The following examples are intended to illustrate practice of the invention, and are not intended to limit the scope of the claimed invention.

Example 1—Synthesis GFP-Mimetic Fluorophore

The most widely used approach for the synthesis of 4-arylidene-5-imidazolinones like those found in green fluorescent protein was first developed by Kojima et al. ("Fluorescent Properties of Model Chromophores of Tyrosine-66 Substituted Mutants of *Aequorea* Green Fluorescent Protein (GFP)," *Tet. Lett.* 39:5239-5242 (1998), which is hereby incorporated by reference in its entirety) and involves an Erlenmeyer azlactone formation between N-acetyl glycine and a 4-hydroxybenzaldehyde. The resulting azalactone is then subjected to aminolysis and subsequent cyclization under alkaline conditions to form the final 4-hydroxybenzylidene-5-imidazolinone (HBI).

Fundamentally the same synthesis was used here, except that a different substituted benzaldehyde was used to generate the novel fluorophore 3,5-dimethoxy-4-hydroxybenzylidene-5-imidazolinone (DMHBI). It was expected that the addition of these substituents would provide additional points of interaction for RNA that would make it easier for the RNA aptamers to rigidify the fluorophore, and thereby induce fluorescence.

As shown in FIG. 1A, DMHBI was synthesized by starting with the commercially available 3,5-dimethoxy-4-hydroxybenzaldehyde and reacting with N-acetylglycine and sodium acetate in refluxing acetic anhydride. N-acetylglycine (0.65 g, 0.005 mol), sodium acetate (0.5 g, 0.005 mol), 3,5-dimethoxy-4-hydroxybenzaldehyde (1.00 g, 0.005 mol), and acetic anhydride (10 ml) were stirred at 90° C. (After 1 hour, a spot to spot conversion to product was observed by thin layer chromatography.) After 2 hours, the reaction was then removed from heat and cooled to room temperature. Ice cold ethanol was then slowly added to the stirring suspension and the reaction was left at 4° C. in the dark over night. The resulting crystalline solid (bright yellow crystals) was washed with 20 ml ethanol (1× at −20° C.), 20 ml hot water (3×), 20 ml hexane (1×) and dried in vacuo. A yield of g (70%) was obtained. $^1$H NMR (400 MHz, CHCl$_3$-d$_4$) δ 2.37 (s, 3H, CH$_3$), 2.41 (s, 3H, CH$_3$), 3.89 (s, 6H, methoxy carbon), 7.27 (s, 1H, on bridging carbon), 7.44 (d, 2H, aromatic)

The purified azalactone was then refluxed in ethanol with potassium carbonate and excess methylamine in a one pot aminolysis and recyclization reaction. The synthesis of 4-(4-hydroxy-3,5-dimethoxybenzylidene)-1,2-dimethyl-imidazol-5-one was carried out by refluxing the azalactone (1.24 g, 0.05 mol) with 15 ml of ethanol, 1 ml of 40% aqueous methylamine, and 700 mg of potassium carbonate for 4 h. The reaction mixture was cooled to room temperature, washed with 1M HCl, concentrated and purified by column chromatography A yield of 64% was obtained. $^1$H NMR (400 MHz, DMSO-d$_6$) δ 2.37 (s, 3H, CH$_3$), 3.11 (s, 3H, CH$_3$), 3.89 (s, 6H, methoxy carbon), 6.91 (s, 1H, on bridging carbon), 7.62 (d, 2H, aromatic).

Example 2—Synthesis of Resin-Immobilized Fluorophore

To perform SELEX and pull out RNAs that could bind to the designed fluorophores of the present invention, a strategy was needed to immobilize the designed fluorophores on resin. Thus, a general synthesis mechanism for generating fluorophores containing an aminoalkyl linker was developed. The aminoalkyl linker could be linked to a commercially available NHS-activated resin (FIG. 1B).

The azalactone intermediate (prepared in Example 1) was first reacted with N-t-butyloxycarbonyl (BOC)-1,6-hexanediamine for aminolysis and subsequent cyclization. After silica gel purification of the BOC-protected product, the BOC moiety was removed with trifluoroacetic acid (TFA) treatment in dichloromethane. Silica gel purification yielded a pure fluorophore with a hexyl linker and a free amine to couple to an amine-reactive resin.

Linker-modified DMHBI was then coupled to NHS-activated agarose resin. The fluorophore was first dissolved in DMSO at a concentration of 40 mM and then diluted into 100 mM HEPES buffer pH 7.5 with a final concentration of 5% DMSO and 2 mM DMHBI. This final fluorophore solution was then added to NHS-activated agarose which had been pre-equilibrated with 2 volumes of ice cold buffer. The resin was then left to react with fluorophore overnight at 4° C. in the dark. The next day, the resin was washed thoroughly with alternating acidic and basic washes and stored in 70% ethanol sodium acetate (NaAc), pH 5.4, at 4° C. Because DMHBI has a distinct absorption spectra that peaks at 400 nm at neutral pH, the yield of fluorophore coupling to agarose could be easily measured. Absorbance ($A_{400}$) measurements were taken of the fluorophore coupling solution before and after reaction with agarose. Using the extinction coefficient of DMHBI determined by standard solutions, ~95% coupling of modified fluorophore to the NHS-agarose was achieved. This reaction yield indicates that there were approximately 5 µmols of fluorophore for every 1 ml resin.

Example 3—Fluorescence Characterization of Novel GFP-Mimetic Fluorophores

In GFP, the chromophore is held inside the protein β-barrel structure and rigidified by direct interactions with over a dozen amino acid residues (FIG. 1C). This inflexible positioning of the chromophore by the protein is the reason for its large fluorescent quantum yield. Similarly, the synthetic GFP chromophores 4-hydroxybenzilidene-1,2-dimethyl-imidazol-5-one ("HBDI") is capable of bright fluorescence only when rigidified by solidified solvents (Niwa et al., "Chemical Nature of the Light Emitter of the *Aequorea* Green Fluorescent Protein," *Proc. Nat'l Acad. Sci. USA* 93:13617-13622 (1996), which is hereby incorporated by reference in its entirety). Therefore, immobilization of DMHBI was performed to confirm whether DMHBI also exhibits this immobilization-dependent fluorescence that is seen in the native fluorophore. As an initial experiment DMHBI was first dissolved in ethanol and frozen in liquid nitrogen to create an ethanol glass matrix. As has been reported with the naturally-occurring GFP fluorophore, the substituted fluorophore was nonfluorescent at room temperature and exhibited dramatic fluorescent enhancement upon freezing (FIG. 2A).

To more precisely determine the effect of immobilization on DMHBI fluorescence, 10 µM DMHBI in aqueous buffer was prepared and its fluorescence spectrum was measured in increasing concentrations of glycerol. Because glycerol is known to affect the viscosity of aqueous solutions in a predictable manner, the effect of increasing viscosity on DMHBI fluorescence can be readily measured. An increase in fluorescence intensity with increasing concentrations of glycerol was observed (FIG. 2B). Importantly, very limited fluorescence is seen at glycerol concentrations of 20%, which corresponds to the viscosity levels measured to exist in the cytosol (Endre and Kuchel, "Viscosity of Concentrated Solutions and of Human Erythrocyte Cytoplasm Determined from NMR Measurement of Molecular Correlation Times; The Dependence of Viscosity on Cell Volume," *Biophys. Chem.* 24:337-356 (1986), which is hereby incorporated by reference in its entirety)).

Further analysis of the fluorescence properties of DMHBI showed that in highly viscous solutions at physiological pH (7.4) the fluorophore exhibits an excitation peak at 400 nm and an emission peak at 460 nm. This is in agreement with previously reported data of the fluorescence spectrum of synthetic GFP chromophore, which is incapable of the excited-state proton transfer reaction that is responsible for green emission spectra found in the GFP protein. The original GFP protein was found to have a maximum excitation at 400 nm as well. The reason for this is that the phenolic moiety of the chromophore remains protonated at neutral pH and in the context of the original protein. Deprotonation to the phenolate results in an excitation maxima at ~475 nm.

Previous studies to utilize conditionally fluorescent RNA binding dyes had focused on triphenylmethane scaffold dyes such as malachite green. However, these studies were halted by the discovery that many of these conditionally fluorescent dyes could interact with cellular components causing the cells to nonspecifically fluoresce. To determine whether the fluorophores of the present invention would be nonspecifically fluorescent in cells, HEK 293 cells were incubated with 10 µM DMHBI and visualized using an epifluorescent microscope. The fluorophore-treated cells show no increase in background fluorescence compared to cells treated only with vehicle (FIG. 2C). In contrast, cells treated with 10 µM malachite green were intensely fluorescent compared to controls (FIG. 2D). This confirms that DMHBI, unlike malachite green, does not bind non-specifically and should be useful for live cell imaging.

Example 4—Identification of RNA Aptamers that Regulate the Fluorescence of the DMHBI Fluorophore To generate RNAs that bind to DMHBI, SELEX was used. SELEX was developed over 15 years ago (Famulok et al., "Nucleic Acid Aptamers—from Selection in vitro to Applications in vivo," *Accounts of Chemical Research* 33:591-599 (2000), which is hereby incorporated by reference in its entirety). SELEX was developed as a method for isolating novel nucleic acid sequences with desired activities. In the years since in development, searches for RNAs that bind ligands specifically and with high affinity have uncovered RNA sequences that bind to a wide range of target molecules, including proteins, sugars, vitamins, cofactors, nucleic acids, amino acids, and even ions. In a typical SELEX experiment, $10^{14}$-$10^{15}$ different RNAs are synthesized and incubated with an immobilized ligand. After extensive washing, RNAs that are specifically bound to the immobilized ligand are eluted with a buffer that contains the free ligand. The eluted RNAs are precipitated and amplified by RT-PCR. Amplified products are used to generate more RNA and the entire process is repeated several times to select for the RNAs that exhibit highest affinity. Because of the enormous combinatorial diversity of the initial library and the ability of RNAs to form diverse tertiary structures, this procedure can yield 10-100 different RNAs that bind to any given small molecule (Gold et al., "Diversity of Oligonucleotide Functions," *Ann. Rev. Biochem.* 64:763-797 (1995), which is hereby incorporated by reference in its entirety). Frequently, these ligands bind the aptamers with low micromolar to sub-nanomolar affinities. For this reason, the SELEX procedure was used in the present invention to identify RNAs with high affinity to DMHBI.

The initial SELEX library was designed with a 70 nucleotide random sequence flanked by two constant sequences which were used for RT-PCR amplification after each round of SELEX. The 5' and 3' constant sequences contained restriction enzyme sites for EcoRI and XhoI cleavage, respectively. The presence of these restriction enzyme sites allowed for subcloning of the library for screening and to check the integrity of the library after each round.

The library was obtained as a single stranded DNA sequence from the Keck Oligo Synthesis Core Facility at Yale University (New Haven, Conn.). Because long chemically synthesized libraries often contain truncated products due to errors in base coupling efficiencies, a common approach is to remove these truncated products by gel electrophoresis. Therefore, a fraction of the initial library was run on a 10% TBE-Urea acrylamide gel to purify full-length DNA products. The full-length DNA band was visualized and cut out with UV shadowing, and then recovered from the gel using the crush and soak method.

Purified ssDNA library was then used in a PCR reaction to amplify the library and to create dsDNA templates for RNA in vitro synthesis. To avoid over amplifying the library, which would induce bias and reduce its complexity, the library was amplified in a rather large (10 ml) PCR reaction for only 14 cycles. The dsDNA PCR product was then purified by a DNA extraction column to remove proteins, primers, and salts. The PCR reaction added on a 5' T7 RNA polymerase promoter sequence for RNA in vitro synthesis reactions.

The prepared dsDNA library was next prepared for use in a SELEX experiment to enrich for RNAs that could bind to DMHBI. Briefly, $2.5 \times 10^{14}$ different sequences of DNA were transcribed in a large T7 RNA polymerase transcription reaction. After treatment with DNase, RNAs were precipitated using ammonium acetate (NH$_4$Ac) and washed with cold 75% ethanol. After air drying, the RNA pellets were resuspended in 1× selection buffer containing 40 mM HEPES.KOH pH 7.4, 150 mM KCl, 5 mM MgCl$_2$, and 5% DMSO. The RNA was then heat denatured at 75° C. for 5 min and quickly moved to an ice bath to cool.

To remove RNAs that bind to the agarose affinity matrix or recognize the linker portion of the DMHBI resin, the RNA library was first incubated with a "mock" resin. The mock resin consisted of NHS-activated agarose that had been treated with free hexylamine under the exact same reaction conditions as the DMHBI resin coupling. RNAs were then incubated with DMHBI agarose and washed extensively with selection buffer. Those sequences from the pool that bind DMHBI directly were retained on the resin, while those sequences that do not bind were removed in washing steps. Bound RNAs were eluted with selection buffer containing 2 mM free DMHBI. RNAs were eluted over the course of two hours to ensure the enrichment of high affinity aptamers. Eluting RNAs with free DMHBI rather than with RNA denaturing reagents such as EDTA or heat, further ensures that selected RNAs do not require the affinity matrix or the aminohexyl linker for binding.

The eluted RNAs were then ethanol precipitated, reverse-transcribed, PCR amplified and in vitro transcribed to yield the pool for the next round. After several rounds, shorter incubation times and less resin volume were used to further force the selection of aptamers with the highest affinity for DMHBI. In later rounds, the stringency of the washing steps was also increased, including brief washes with DMHBI itself in the attempt to eliminate low and moderate affinity aptamer. It has been demonstrated previously that these brief pre-elution steps can help enrich for aptamers with low off-rate and thus high affinity (Davis and Szostak, "Isolation of High-Affinity GTP Aptamers from Partially Structured RNA Libraries," *Proc. Nat'l Acad. Sci. USA* 99(18):11616-11621 (2002), which is hereby incorporated by reference in its entirety). From rounds five through ten, both the number and incubation time of the DMHBI wash steps was slowly increased.

After each round of SELEX, $^{32}$P-UTP labeled RNA was synthesized to monitor binding of the RNA to the beads. Within a few rounds of SELEX, significant amounts of the radiolabeled RNA bound to the resin were detected. By round five, nearly half of the RNA library could bind to DMHBI agarose. To determine if RNA aptamers that could switch on the fluorescence of DMHBI were also enriched, the RNA from each round was incubated with DMHBI. As shown in FIG. 3A, RNA beginning from round five exhibited an ability to switch on DMHBI fluorescence. However, the DMHBI-inducing activity of the pools was weak, even after ten rounds (FIG. 3A), which could reflect that the RNA pool contained only a few aptamers that bind in a way that is conducive to switching on the fluorescence of DMHBI. Further rounds of selection resulted in a decrease in overall fluorescence of the library, so clones from round ten were screened. Upon testing 50 individual clones from round 10, it was found that none of the clones were capable of switching on DMHBI fluorescence, even though many were capable of binding DMHBI agarose. Thus, to screen more quickly, 40 pools of 10 clones were screened, and only two pools were found that contained the ability to switch on DMHBI fluorescence. After deconvolving the pools by screening 5 pools of 5, and then individual clones, two unique RNAs were identified that switched on DMHBI fluorescence. These clones were named after the pools from which they were identified, 3-6 and 13-2, and their sequences are shown below by their encoding DNA sequences:

Clone 3-6
(SEQ ID NO: 34)
GGGAGATACGCTCTAGAATTCAATTGCATGGTGGTCTGGGACAGACGTGT

GGACGGCACACAGCGTGAGGCTTTGGTGGGTTATGGCTGTCATGCGAGAT

AGCTCGAGCAATGC

Clone 13-2
(SEQ ID NO: 35)
GGGAGATACGCTCTAGAATTCAATTTGCGTATTGAGACAGGGCCGCGCTA

TTTCTGGAGGGGCGCTACATGAAAGTGGTGGTTGGGTGCGGTCGGAGATA

GCTCGAGCAATGC

Both aptamers 3-6 and 13-2 exhibit roughly the same excitation spectra with a peak at ~400 nm (FIG. 3B). Interestingly, although the emission spectra of these two clones was found to be slightly different, with 3-6 peaking at ~535 nm and 13-2 peaking at ~525 nm, both clones exhibit roughly the same fluorescence brightness when compared mole per mole. This means that these difference in emission could not be due to an artifact of the fluorimeter readout levels. This indicates that the RNA structure is capable of subtle change to the fluorophore color, something known to occur in the context of different fluorescent protein mutants but never before shown for aptamers. This opens up the exciting possibility that these RNAs may be evolved such that a wider range of colors can be achieved using a single fluorophore. This was precisely demonstrated in Example 13, infra.

The fluorescence of both clones was remarkably bright as can be seen in FIG. 3C. Neither aptamer nor DMHBI, alone, is fluorescent even at micromolar concentrations. However, when mixed, the resulting aptamer-fluorophore complex exhibits a bright green fluorescence that can readily be seen by eye.

This example confirms that SELEX can be used to search for RNA aptamers that bind specifically to and induce enhanced fluorescent emission of novel fluorophores of the invention. SELEX was therefore used to identify aptamers that bind to other fluorophores described herein.

Example 5—Truncation Studies to Identify a Minimal Aptamer Domain

Once RNA aptamers capable of inducing DMHBI fluorescence were identified (in Example 5), the next step was to identify a minimal domain required for binding and inducing fluorescence. The 3-6 and 13-2 RNA sequences in their entirety, including constant regions, were over 100 nucleotides in length (see FIGS. 4A (SEQ ID NO: 1) and 4B (SEQ ID NO: 2)).

Figure 8:
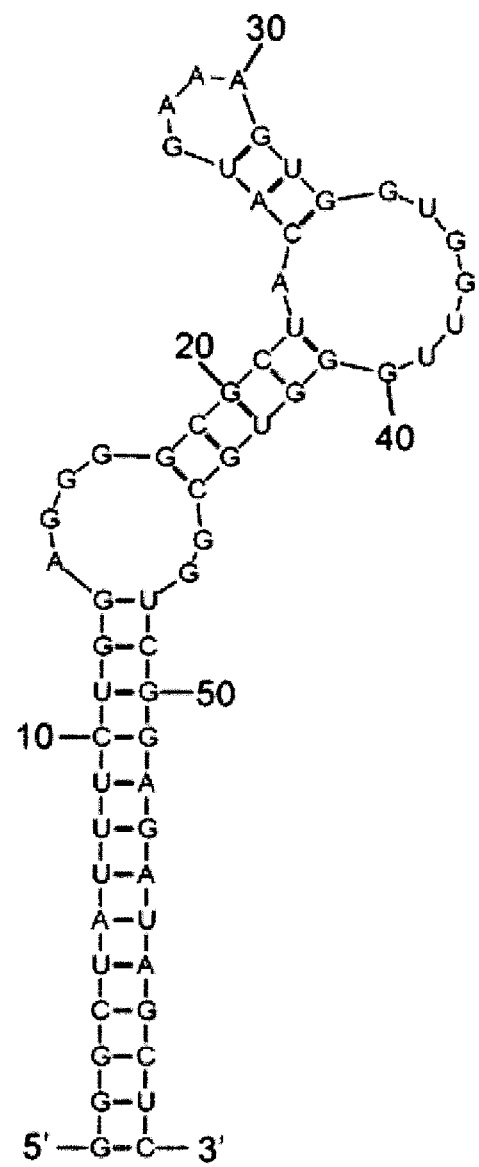
FIG. 8 shows the predicted secondary structure for 13-2 minimal sequence, designated "13-2-min" (SEQ ID NO: 3).

Because one of the goals was to incorporate these aptamers into the 3' UTR of an mRNA (to monitor mRNA trafficking in vivo, it was important to identify the smallest possible sequence to limit any effect on mRNA structure. The approach taken was to truncate aptamers by 5 nucleotides at a time on either the 5' or 3' end and then test the ability of the new truncated aptamers to induce DMHBI fluorescence. Unlike most aptamers reported in the literature, both 3-6 and 13-2 were highly sensitive to truncation, including the constant region. Clone 3-6 could not tolerate any truncation without significant loss of fluorescence, and 13-2 could only tolerate a modest truncation down to 60 nucleotides (FIG. 8). Because clone 13-2 could be truncated (13-2-min) and was slightly more fluorescent than 3-6, it was selected for use in the Examples below.

Example 6—Characterization of DMHBI Aptamer Complexes

The first step in characterizing the interaction between fluorescence-inducing aptamers of DMHBI was to determine their binding affinities. Because binding of the RNA to DMHBI results in fluorescence, the dissociation constant ($K_d$) was obtained by titrating increasing amounts of DMHBI to a solution of the aptamer. To correct for any increases in DMHBI background fluorescence, measurements of DMHBI alone at the same concentrations were taken and subtracted from the binding data. These measurements were then used to extrapolate RNA-fluorophore dissociation constants. DMHBI bound to both 3-6 and 13-2 with roughly equal dissociation constants of 500 nM (FIG. 5A).

Fluorescence was also used to measure thermal unfolding of these aptamers. The thermal denaturation profile of the aptamers showed that the melting temperature ($T_m$) for aptamer 13-2 was around 45° C. (FIG. 5B), indicating that these RNA-fluorophore complexes would remain folded in cultured cells at 37° C. Interestingly, aptamer 3-6 becomes slightly more fluorescent as the temperature is increased from 25° C. to 37° C., and then rapidly begins unfolding as temperatures increase further. This indicates that 3-6 may have several stable conformations at 25° C., only one of which is capable of binding to the fluorophore. However, at 37° C., the fluorophore binding conformation becomes more thermodynamically favorable resulting in increased fluorescence.

Lucifer Yellow and Cascade Yellow, two fluorophores with known quantum yields, were used as standards and the relative slope changes in the curve depicting absorbance vs. total fluorescence were compared. Values were calculated for DMHBI alone and DMHBI with aptamer 13-2 to identify the underlying reason for fluorescence increase. As expected, the molar extinction coefficient remained relatively unchanged between unbound and bound DMHBI at 13,164 and 15,358 $M^{-1}cm^{-1}$, respectively. Quantum yield, however, increased enormously from 0.0006 for DMHBI alone to 0.08 for the aptamer-DMHBI complex—an over 100-fold increase. Total brightness, measured as the product of extinction coefficient and quantum yield, went from 0.008 to 1.23 (150-fold). Although not quite as bright as GFP, these complexes were comparable in brightness to some of the less bright fluorescent protein derivatives such as mHoneydew. More importantly, the fold-increases in both quantum yield and brightness are more than sufficient for detection of the aptamer-fluorophore complex.

Because DMHBI-aptamers can be used in cells for live cell imaging of RNA, it was tested how resistant the RNA-DMHBI complex was to different solvent conditions. Aptamers were originally tested in buffers selected to reflect the condition of the intracellular milieu, including neutral pH, 150 mM KCl and 5 mM $MgCl_2$. However, cellular conditions are known to vary in both pH and ionic conditions, so the resistance of 13-2 to these changes was tested.

The pH tolerance of 13-2 was tested according to the following method. In live cells, pH can vary between 5-8 in different cellular compartments. Susceptibility to changes in pH could hamper the utility of aptamer-fluorophore complex in living cells. In fact, one of the major problems associated with the wild type (wt) GFP protein is its pH-sensitivity. Because the RNAs more closely resemble the fluorescence profile of wt GFP, it was necessary to determine if the complexes of the present invention would also be sensitive to pH changes. In the presence of excess DMHBI, 13-2 retained its fluorescence in a pH range from 6-8.

The dependence of aptamer 13-2:DMHBI fluorescence on potassium levels was also tested. Selection conditions used 150 mM KCl to reflect the monovalent ion concentrations of the cytosol. KCl was used instead of the more commonly used NaCl because several RNA structures are known to require $K^+$ in their structure and to better reflect cytosolic conditions. As can be seen in FIG. 6A, decreasing KCl concentrations had a more dramatic effect on 13-2:DMHBI fluorescence than magnesium levels. Replacing KCl with another monovalent ion such as NaCl did not restore fluorescence, implying a specific $K^+$-RNA interaction is required for aptamer 13-2 fluorescence induction of DMHBI. However, this may not be the case with other RNA aptamers selected for binding to fluorophores.

Next, the importance of $Mg^{2+}$ for RNA-induced DMHBI fluorescence was tested. The selection conditions contained 5 mM $MgCl_2$; however, intracellular free $Mg^{2+}$ concentrations are thought to be much lower, around 0.5-0.1 mM. While increasing the $Mg^{2+}$ did not affect the fluorescence, removing $Mg^{2+}$ from the buffer decreased the fluorescence by approximately 25% (FIG. 6B). Fluorescence remained even in the absence of $Mg^{2+}$, indicating that aptamer 13-2 was not entirely dependent on divalent cations for folding. This was somewhat surprising, considering that most reported aptamers to small molecules require some level of divalent cation for binding.

The results of these tests confirmed that the 13-2:DMHBI complexes would be able to fluoresce across the range of pH/ion conditions found in live cells.

Example 7—Characterization of Aptamer Concatemers on DMHBI Fluorescence

Given the low quantum yield of 13-2 when compared to GFP, it was concluded that single aptamers might be difficult to visualize in cells. Therefore, several aptamer units were concatenated to increase the relative fluorescence per molecule. To determine if adding 13-2 sequences in tandem repeats could increase fluorescence, 13-2 RNA monomers, dimers, or tetramers were prepared and compared. Fluorescence at equimolar concentrations of RNA molecules was obtained. As shown in FIG. 7, increasing the number of concatenated aptamers resulted in linearly increasing levels of fluorescence. These results demonstrate that multiple molecules of DMHBI bound to concatenated aptamers do not quench each other as multiple fluorophores often do when conjugated to a single protein. Therefore, for the purposes of the present invention, increased brightness is attainable if multiple units of fluorophore-binding aptamers are linked in series. Indeed, it has been shown that up to 32 tandem 13-2 aptamers do not exhibit cross interference and anomalously low fluorescence due to resonance energy transfer or inter-aptamer interactions. This should allow for monitoring of small numbers of molecules, even single molecules, when the aptamer concatemers are linked to or are otherwise made to bind to a target molecule of interest.

Example 8—Optimizing DMHBI Aptamers

For DMHBI aptamers to be potent tools for live cell imaging of RNA, brightness of the RNA-DMHBI complexes may have to be increased. To do this, a combination of both rational design and random mutagenesis was used to screen for mutants of aptamer 13-2 that could further increase the fluorescence of DMHBI upon binding. Increases in quantum yield might be attained, for example, if the RNA-fluorophore complex adopts a more rigid structure to prevent more non-radiative decay of the fluorophore or simply by designing fluorescent fluorophores with higher quantum yield.

The optimization of 13-2 was done by closely analyzing the predicted secondary structure of the minimal sequence of 13-2 (designated "13-2-min", SEQ ID NO: 3), which was capable of eliciting maximum fluorescence. The predicted secondary structure of 13-2-min can be seen in FIG. 8. Noticing several weak structural points, single point mutations were made and tested for their effect on fluorescence intensity. First, the minimal domain revealed several stem-bulge junctions where the junction was closed by a G-U base pair, which were mutated to G-C pair. Next, any other G-U base pairs were replaced with G-C base pairs. Finally, any A-U base pairs were replaced with G-C base pairs. This led to the discovery of several point mutations that increased DMHBI fluorescence upon binding. To determine whether several of these mutations together would have an additive effect, several of the best mutations were tested together. The results obtained are summarized in Table 1. Overall, three critical mutations were identified, which together increased the fluorescence of the RNA-fluorophore complex two-fold.

TABLE 1

Mutations to 13-2-min Sequence (SEQ ID NO: 3) and Their Effect on DMHBI Fluorescence

| Base Position | Base Mutation | Percentage of 13-2-min Fluorescence (%) |
|---|---|---|
| 6, 55 | A to C, U to G | 95 |
| 8 | U to C | 97 |
| 9, 52 | U to G, A to C | 115 |
| 11 | U to C | 68 |
| 22 | U to C | 157 |
| 43 | U to C | 32 |
| 59 | U to C | 86 |
| 9, 22, 52 | U to G, U to C, A to C | 192 |
| 6, 8, 9, 22, 52, 55, 59 | A to C, U to C, U to G, U to G, A to C, U to G, U to C | 163 |
| Remove bases 27-30 (GAAA) | Replace with GCUUCGGC | 27 |
| 5, 56 | U to C, A to G | 94 |
| 7, 54 | U to G, A to C | 87 |
| 48 | U to C | 12 |
| 26 | U to C | 49 |
| 5, 6, 8, 9, 22, 52, 55, | U to C, A to C, U to C, U to | 86 |
| 56, 59, | G, U to G, A to C, U to G, A to C, U to C | |

Next, random mutagenesis coupled with in vitro selection was used to optimize aptamer 13-2 in a non-biased approach. To do this, an affinity maturation strategy was used which is commonly used in aptamer selections. The original parent library used in the DMHBI selection had a stretch of 70 randomized nucleotides. This would correspond to $10^{42}$ possible different sequences. However, since oligonucleotide libraries for SELEX are made at the μmole scale, and only a fraction of this can be used for in vitro transcription reactions, only $10^{14}$-$10^{15}$ different RNAs can be sampled at a time. This is a minute fraction of the potential sequence space that could be sampled. A more thorough sampling of the sequence space can be achieved through affinity maturation in which a new library is created with a bias for the sequence of 13-2.

In this process, the 13-2 DNA sequence was chemically re-synthesized, such that each position was mutagenized at a level of 30%. This was achieved by doping each phosphoramidite solution with 10% of each of the other bases. In other words, in each step of the DNA synthesis, instead of making the aptamer with a 25% mix of each of the four dNTPs, the dNTP mixture comprised the dNTP that is found in 13-2 and the other three dNTPs in a 7:1:1:1 ratio. This produced a completely novel library of $10^{14}$ different sequences, all with increased potential to bind DMHBI.

When SELEX was performed with this library, more rigorous washing conditions were used, including buffers preheated to 37° C., larger wash volumes, and washing with higher salt buffers. Unlike the original screen where fluorescence appeared in later rounds and was faint, fluorescence appeared in early rounds during this process and was robust. After round 5, individual clones were screened. Each of the fluorescent clones exhibited emission maxima that peaked at 525 nm. Several dozen clones were screened, and four clones were selected that were brighter than the original 13-2. The sequences of these four clones are presented below by their encoding DNA sequences:

Clone 13-2-1
(SEQ ID NO: 36)
GGGTATCCGGAATCTTATACATTGTTATGTCTGGAGGGGCGCCGCATGAA

CGCGGTGGTGAGGTGCGGTCGGATATAACTGGTGGAGTGCAAGAGTCTGA

GCACACTGG

Clone 13-2-3
(SEQ ID NO: 37)
GGGTATCCGGAATCTTATACATTGCTATTTCTGGAGGGGCGCCCCATGAA

AGGGGTGGTTGAGAGCGGTCGGAGATAGCGGAAACAGTGCAAGAGTCTGA

GCACACTGG

TABLE 1-continued

Mutations to 13-2-min Sequence (SEQ ID NO: 3) and Their Effect on DMHBI Fluorescence

| Base Position | Base Mutation | Percentage of 13-2-min Fluorescence (%) |
|---|---|---|
| 56, 59, | G, U to G, A to C, U to G, A to C, U to C | |

Clone 13-2-4

(SEQ ID NO: 38)
GGGTATCCGGAATCTTATACATTGCTATTGTTGGAGGGGCGCTACGTGAA

AGTGGTGGTACGGTGCGGTCGGCAATAGCTCGTATAGTGCAAGAGTCTGA

GCACACTGG

Clone 13-2-5

(SEQ ID NO: 39)
GGGTATCCGGAATCTTATACATTGCTCTGTTTGGAGGGGCGCTACTTTCA

AGTAGTGGTTGAGTGCGGTCGAACAGAGCTTGGGCGTTGCAAGAGTCTGA

GCACACTGG

Figure 9:
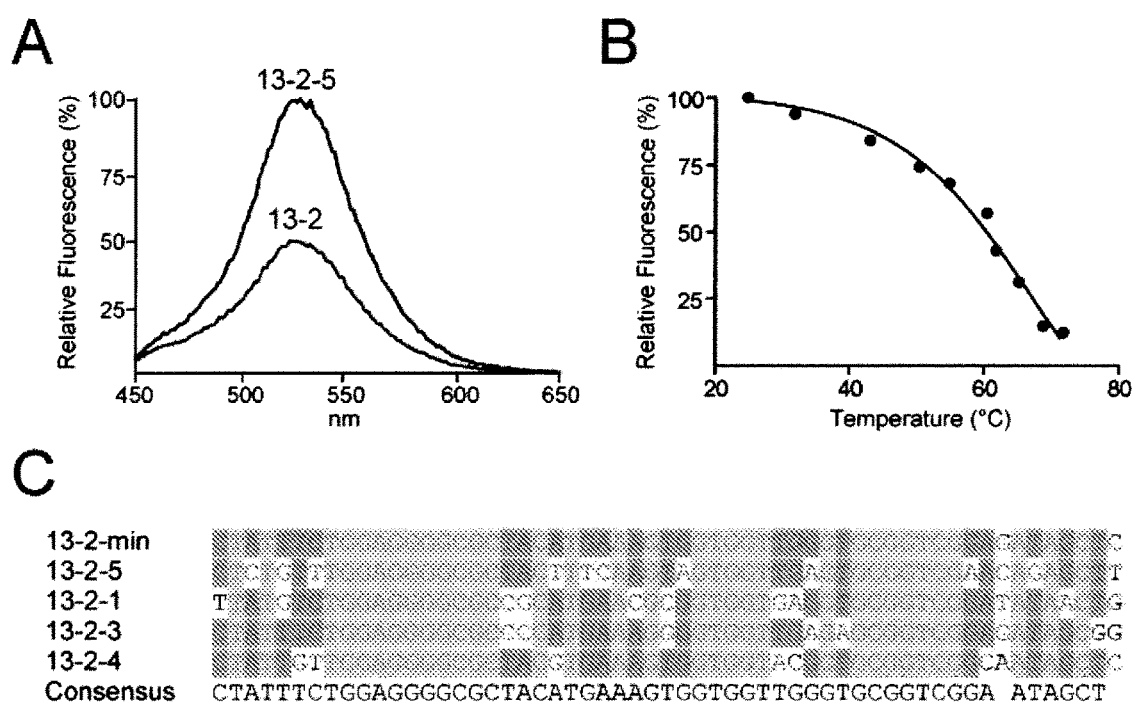
FIGS. 9A-C show that affinity maturation results in DMHBI aptamers with increased brightness and melting temperatures.

Clone 13-2-5 was the most promising of these clones, exhibiting nearly twice the fluorescence (FIG. 9A) of 13-2. Additionally, 13-2-5 had a $T_m$ of ~45° C. (FIG. 9B), which makes it much more stable at 37° C. used for live cell imaging. An alignment of the doped library hits with 13-2-min reveals several regions of consensus among all clones, indicating the importance of these regions in fluorophore recognition (FIG. 9C, SEQ ID NO: 40).

Figure 10:
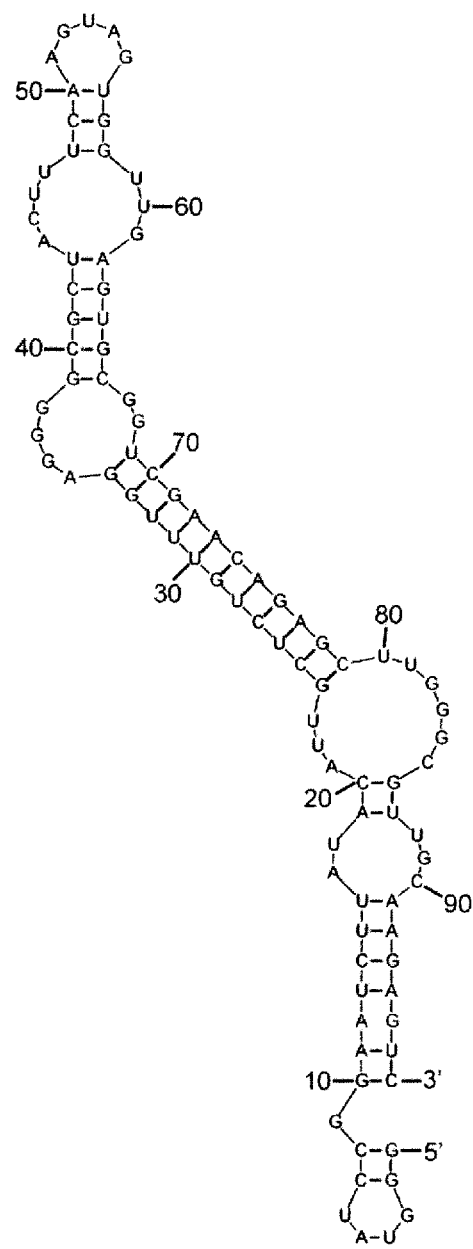
FIG. 10 shows the predicted secondary structure for 13-2-5 minimal sequence, designated "13-2-5-min" (SEQ ID NO: 15).

The predicted secondary structure of clone 13-2-5 had several similarities in overall structure to 13-2-min, including the sequence of stem-bulge motifs. Truncation analysis of 13-2-5 revealed a requirement of the 5' constant region and the entire randomized sequence. However, part of the 3' constant region could be removed without a reduction in fluorescence, leading to a minimal sequence named 13-2-5-min (FIG. 10, SEQ ID NO: 15). Using the same strategy for rational mutagenesis, several point mutations were made systematically that subtly increased the fluorescence intensity. These mutations and their effect on the fluorescence of DMHBI are shown in Table 2.

TABLE 2

Mutations to 13-2-5-min Sequence (SEQ ID NO: 15) and Their Effect on DMHBI Fluorescence

| Base Position | Base Mutation | Percentage of 13-2-5-min Fluorescence (%) |
|---|---|---|
| 26, 77 | U to G, A to C | 82 |
| 28, 75 | U to C, A to G | 110 |
| 30, 73 | U to C, A to G | 109 |
| 31, 72 | U to G, A to C | 114 |
| 32 | U to C | 112 |
| 64 | U to C | 113 |
| 32, 30, 73, 26, 77 | U to C, U to C, A to G, U to G, A to C | 111 |
| 31, 72, 28, 75 | U to G, A to C, U to C, A to G | 105 |
| 26, 28, 30, 31, 32, 72, 73, 75, 77 | U to G, U to C, U to C, U to G, U to C, A to C, A to G, A to G, A to C | 92 |
| 48 | U to C | 44 |
| 43, 62 | U to G, A to C | 4 |
| 43, 62 | U to C, A to G | 5 |
| 69 | U to C | 15 |
| Remove bases 50-55 (AAGUAG) | Replace with GGCUUCGGC (5'-3') | 5 |
| 19, 87 | A to G, U to C | 99 |
| 16, 91 | U to C, A to G | 88 |
| 11, 12, 15, 92, 94 | A to G, A to C, U to G, A to G, A to G | 58 |

Example 9—Synthesis of a Novel Fluorophore with Reduced Phenolic pKa

Most commonly used GFP variants, for example enhanced GFP (eGFP), have chromophores predominantly in the higher-absorbing phenolate form. The fluorescence spectra of the RNA-DMHBI aptamer implies that all the fluorophore was in the phenol form, and none was in the phenolate form, indicating that the RNA-fluorophore complex was more analogous to the original wt GFP than it was to eGFP. This can be explained by the negative charge of the RNA phosphate backbone. There have only been a handful of prior reports of RNA aptamers selected against negatively charged molecules, and in most cases the aptamers against these molecules do not interact directly with the negative charge. Thus, future selections made against DMHBI are unlikely to result in phenolate binding aptamers due to the overabundance of phenol containing molecules at neutral pH. Obtaining significant increases in brightness, therefore, would require selecting for aptamers that can bind the phenolate form of a particular fluorophore.

To overcome this limitation, a novel fluorophore was designed in which the methoxy groups of DMHBI were replaced with fluoro groups (FIG. 11A). It was predicted that the high electronegativity of fluorine would create an inductive effect on the benzylidene ring, resulting in a decreased $pK_a$ of the phenolic proton. Indeed, the effect of adding fluoro groups to phenol has been reported to reduce the $pK_a$ of phenol by several pH units (Gross and Seybold, "Substituent Effects on the Physical Properties and $pK_a$ of Phenol," Int. J. Quantum Chem. 85(4-5):569-579 (2001), which is hereby incorporated by reference in its entirety). To synthesize this novel fluorophore, the same azalactone synthesis was used as for DMHBI, but instead using 3,5-difluoro-4-hydroxybenzaldehyde as a starting material. As before, azalactone reacted with either methylamine or with N—BOC-1,6-hexanediamine under alkaline conditions to produce ligand and linker forms of 3,5-difluoro-4-hydroxy-benzylidene-imidazolin-5-one (DFHBI) fluorophore, respectively.

The $pK_a$ of DFHBI was calculated using the presence of the distinct phenol and phenolate absorbance peaks. The addition of the fluoro groups caused a blue shift on both peaks to a maxima of 363 nm for the phenol and 420 nm for the phenolate; however, the peak ratios still changed in a pH-dependent way and the $pK_a$ was calculated to be ~6.0 (FIG. 11B). This dramatic reduction in pH would ensure that a majority of fluorophore molecules would now be in the phenolate form at physiological pH.

As with the DMHBI fluorophore, DFHBI also exhibited negligible fluorescence in non-viscous solutions but became robustly fluorescent in both ethanol glass and at high glycerol concentrations. Additionally, DFHBI was nonfluorescent when administered to HEK 293 cells, proving its utility for methods involving live cells.

Example 10—Selection of Novel Aptamers to DFHBI Using a Pre-Structured Library

To identify RNAs that bound to DFHBI, SELEX was performed using DFHBI-derivatized agarose. However, unlike the selection against DMHBI, the library was not a completely random library. Instead, the initial RNA library was partially structured with a central 12-nt sequence encoding a 4-bp stem closed by a stable UUCG loop, flanked by 26 random bases on either side. SELEX was then carried out as described in Example 4.

The fluorescence of the library was assayed after each round of SELEX. Unlike the gradual increase in fluorescence seen after each round of the DMHBI selection, in this case fluorescence went up exponentially after round 4 and then quickly leveled off after round 6. This indicates that the partially structured library had more potential hits than the completely random library (used for DMHBI selection). Clones from rounds 6 and 7 were screened, and dozens of hits were identified. After sequencing it was discovered that most hits were redundant and there were only three unique sequences that induced DFHBI fluorescence. The three sequences are presented below by their encoding DNA sequences:

```
Clone 10-6
                                          (SEQ ID NO: 42)
GGGAGACGCAACTGAATGAATGAACGGGGTAAATAGGCGTGGGTCGGGTC

CTGCTTCGGCAGTTGAGTGTGAGAGCGAACTCTGTAGTTCCGTAACTAGT

CGCGTCAC

Clone 24-1
                                          (SEQ ID NO: 43)
GGGAGACGCAACTGAATGAACCTGTAGAACGACTTGGTCGGGTCAGCTGC

TTCGGCAGCTTCGAGAATAGAGTGTGGGGTCGTATCCGCGTAACTAGTCG

CGTCAC

Clone 24-2
                                          (SEQ ID NO: 44)
GGGAGACGCAACTGAATGAAATGGTGAAGGACGGGTCCAGGTGTGGCTGC

TTCGGCAGTGCAGCTTGTTGAGTAGAGTGTGAGCTCCGCGTAACTAGTCG

CGTCAC
```

Example 11—Characterization of DFHBI-Aptamer Complex

All three aptamers to DFHBI exhibited bright green fluorescence that could be seen by eye. The addition of the fluoro groups appeared to cause a slight blue shift in the fluorescence with excitation and emission maxima at 460 nm and 500 nm, respectively (FIG. 12A). All three aptamers shared identical emission spectra, but 24-1 and 24-2 had about twice the fluorescence intensity as 10-6. Thus, further characterization was only carried out on these two brightest clones. Compared to aptamers for either DMHBI or DMABI, aptamers to DFHBI were significantly brighter with an approximately six-fold increase in fluorescence intensity (FIG. 12B). This increased brightness derived mainly from an increase in the quantum yield from 0.08 for DMHBI-RNA complexes to over 0.6 for DFHBI-RNA complexes. The extinction coefficient for DFHBI remained unchanged between unbound and bound fluorophore: 26,000 $M^{-1}cm^{-1}$.

Equimolar solutions of 24-1-DFHBI complex and eGFP were prepared to measure their relative fluorescence intensity. 24-1 RNA was only three-fold less bright than EGFP (FIG. 12C), suggesting that 24-1 is bright enough to be readily visible in cells. Incubating 24-1 and 24-2 in different solvent conditions also indicated that at least 24-2 should fold correctly in cells. Both aptamers are relatively unaffected by changes in pH between 7-8. Dropping the pH to 6.0 resulted in a 50% drop in fluorescence intensity, which is likely due to the preference of the aptamers for the deprotonated form of DFHBI ($pK_a$=6.0). Unlike 13-2, neither 24-1 nor 24-2 required monovalent ions to be fluorescent; however, switching KCl for NaCl resulted in a 10 nm red shift in the emission spectra. $Mg^{2+}$ ion requirement, on the other hand, is much greater for 24-1 and 24-2 than for 13-2 (FIG. 12D). Both 24-1 and 24-2 are optimally fluorescent at 25 mM $MgCl_2$ with only a subtle decrease when the concentration is dropped to 5 mM (the concentration used for SELEX). However, dropping $MgCl_2$ concentration from 5 mM to a more physiological concentration of 0.5 mM results in a 50% drop in fluorescence for both aptamers. Further decreasing the $MgCl_2$ concentration completely abolishes 24-1 fluorescence at ~0.01 mM, while 24-2 levels out at ~45% intensity at 0.01 mM $MgCl_2$.

The large increase in fluorescence could not be accounted for by an increased affinity for the fluorophore as both 24-1 and 24-2 bound DFHBI with binding constants around 600 nM—similar to the $K_d$ determined for 13-2-DMHBI binding. Thus, the increased brightness of these RNA-fluorophore complexes is likely due to an increase in the fluorophore's inherent brightness: namely, the fact that DFHBI is predominantly deprotonated at neutral pH and, thus, resembles the fluorophore of eGFP. To determine if these aptamers were binding to the phenolate version rather than the phenol, the changing ratio of phenol to phenolate absorbance peaks of DFHBI at pH 6, 7, and 8 were measured and compared to changes in excitation spectra at different pH levels. As the pH is changed from 6 to 8, the ratio of peaks in the absorbance spectra changed, but the excitation spectra ratio does not change (FIGS. 13A and 13B). In fact, the absorbance spectra shows a rise in a blue-shifted shoulder peak when the pH is dropped from 7 to 6, while the excitation spectra displays no similar rise in shoulder peak. While the total intensity of the phenolate excitation peak decreases somewhat at pH 6.0, it is most likely due to denaturation of the RNA and/or a decrease in the concentration of deprotonated DFHBI, because the emission spectra is also decreased proportionally (FIG. 13B).

Studies with DMHBI provided further evidence that 24-1 binds to the phenolate form of DFHBI. In these experiments, 24-1 was incubated with 10 μM DMHBI at either pH 7 or 8 and then excited at either 400 nm (representing phenol excitation) or 470 nm (representing phenolate excitation). As shown in FIG. 13C, at pH 7 only weak fluorescence was seen with excitation at either wavelength, suggesting that 24-1 interacts only weakly with DMHBI when a majority of the fluorophore is protonated. However, at pH 8 when ~50% of the DMHBI is deprotonated, 24-1 exhibited a dramatic increase in fluorescence when excited at 470 nm, but still only weak fluorescence when excited at 400 nm. These experiments indicate that 24-1 is only capable of interacting with DMHBI when it is deprotonated. Thus, 24-1 is interacting directly with the phenolate moiety.

Both 24-1 and 24-2 were resistant to any truncations including the constant regions. For 24-1, several residues were removed from the ends of the sequence, which did not seem to play any role in the structure predicted by mFOLD (Zuker, "On Finding All Suboptimal Foldings of an RNA Molecule," *Science* 244:48-52 (1989), which is hereby incorporated by reference in its entirety). The predicted secondary structure for both sequences, 24-1 and 24-2, are provided in FIGS. 14A-B, respectively.

Example 12—Live-Cell Imaging of DFHBI Aptamers

The RNA-fluorophore complexes of the present invention have useful photophysical properties for live cell imaging. Visualizing fluorescence in fixed cells is very efficient since anti-quenching agents, such as DABCO or "Fluoromount," are added to samples. However, these agents cannot be added to live cells, so intracellular small molecule fluorophores exhibit blinking and rapid photobleaching when imaged in living cells. These effects reflect potentially reversible transitions into long-lived dark states, as occurs with the GFP fluorophore (Zumbusch, "Single Molecule Spectroscopy of the Green Fluorescent Protein," *Single Molecules* 2:287-288 (2001); Jung et al, "The Role of Dark States in the Photodynamics of the Green Fluorescent Protein Examined with Two-Color Fluorescence Excitation Spectroscopy," *J. Phys. Chem. A* 104:873-877 (2000), each of which is hereby incorporated by reference in its entirety), but can also involve photo-oxidative destruction (Longin et al., "Comparison of Anti-fading Agents Used in Fluorescence Microscopy Image Analysis and Laser Confocal Microscopy Study," *J Histo Cytochem* 41:1833-1840 (1993); Rasnik et al., "Nonblinking and Long-lasting Single-molecule Fluorescence Imaging," *Nat Methods* 3:891-893 (2006), each of which is hereby incorporated by reference in its entirety). This is a major limitation, especially when imaging small numbers of molecules (Nie et al., "Optical Detection of Single Molecules," *Annual Rev. Biophys. Biomol. Structure* 26:567-596 (1997); Weiss, "Fluorescence Spectroscopy of Single Biomolecules," *Science* 283:1676-1683 (1999), each of which is hereby incorporated by reference in its entirety).

RNA-fluorophore complexes are unique in not having this problem. Because the DMHBI fluorophore is not covalently attached to the aptamer, if it becomes photobleached, it may dissociate and exchange with fluorophores in solution. Indeed, RNA-bound DMHBI is likely to be in rapid equilibrium with DMHBI in solution since the $K_d$ of the complex (500 nM) indicates a dissociation rate that is likely to have a $\tau_{1/2}$ of <0.1 sec, even after assuming diffusion-limited association rates (Silverman, "The Organic Chemistry of Enzyme-catalyzed Reactions," New York: Academic Press, (2002), which is hereby incorporated by reference in its entirety). This will permit higher illumination intensity and longer continuous imaging.

Another experiment was conducted to determine whether these brighter RNA-fluorophore complexes were detectable in live cells. To do this, a transgene was prepared by ligating DNA encoding either 24-1 or 24-2 to the 3' side of the Glutathione S-transferase (GST) open reading frame. These transgenes should afford expression of a GST:24-1 and GST:24-2 fusion mRNA, respectively, when transformed into *E. coli*. The bacteria were then visualized with an epifluorescent microscope using a common GFP filter set. However, no signal was detected.

Northern blot with a probe against the aptamer sequence showed that the RNAs were being expressed in full and were not getting degraded within the cell. Therefore, it was hypothesized that the RNA might be denatured or misfolded when in the context of a long mRNA molecule. To stabilize the sequence it was fused in the middle of a tRNA sequence for Lys to stabilize its structure. This technique has been shown to increase the stability and folding of several aptamers expressed in bacteria (Ponchon and Dardel, "Recombinant RNA Technology: The tRNA Scaffold," *Nature Methods* 4(7):571-6 (2007), which is hereby incorporated by reference in its entirety). Cells were then transformed with tRNA cassette containing a control aptamer which binds to sephadex or fluorophore binding aptamers. *E. coli* expressing 24-1 or 24-2 aptamers were brilliantly fluorescent when compared to control expressing cells (FIGS. 15A and 15B, respectively). 24-2 was about five-fold brighter than 24-1 in cells.

Example 13—Additional DMHBI Aptamer Selection

In the original selection for aptamers against DMHBI, two unique aptamers were identified with slightly shifted emission spectra maxima (525 and 535 nm). This indicates that RNAs, like proteins, have the potential to impose different environments on the fluorophore that may result in spectral changes.

To explore this idea further, SELEX was repeated against the original DMHBI fluorophore. However, two changes where made. First, a partially structured library was used. As demonstrated in Example 10, this should yield more hits than the original completely randomized library. Second, while the original selection had been done at pH 7.4, raising the pH to 8.5 might result in additional structures. All other aspects of the selection were carried out as described above. Screening after ten rounds of SELEX led to the identification of five novel aptamers that switch on DMHBI fluorescence. The sequences of these aptamers are presented below by their encoding DNA sequences:

```
Clone 23-11
                                             (SEQ ID NO: 57)
GGGAGACGCAACTGAATGAAATGACAGTACAGTGGAGGGTGCGGTACTGC

TTCGGCAGGGAAGGGGCGCTGTTCTTGTCTCATATCCGTAACTAGTCGCG

TCAC

Clone 17-3,
                                             (SEQ ID NO: 58)
where N is C or T
GGGAGACGCAACTGAATGAAGAGCAGTAGCGAGTAGTTCACAANAGCTGC

TTCGGCAGGATCTTGTAGGAAGTAAATGTGCAAATCCGTAACTAGTCGCG

TCAC

Clone 2-4
                                             (SEQ ID NO: 59)
GGGAGACGCAACTGAATGAAACCTAGAGTTATGCCAGGCTCTGAGCCTGC

TTCGGCAGGTGCTATGATCGCCAGCGGTATGCAGTCCGTAACTAGTCGCG

TCAC

Clone 17-17,
                                             (SEQ ID NO: 60)
where N is C or T
GGGAGACGCAACTGAATGAAANNAAATATTCGGGATANATANNATTACTG

CTTCGGCAGANAGCGGTTAATTNTTGNAANTCNAATCCCGAACTAGTCGC

GTCAC

Clone 18-16,
                                             (SEQ ID NO: 61)
where N is C or T
GGGAGACGCAACTGAATGAANGGACTCGTCTGGCNGGATGGGCGNGTGGT

ACTGCTTTCGGGCAGGATNGGGTATAACGGTANANGCNCTAACTAGTCGC

GTCAC
```

Surprisingly, while all aptamers had the same excitation spectra at 400 nm, each varied widely in their emission spectra (FIG. 16). Clone 23-11, the brightest of these aptamers, was twice as fluorescent as the original aptamer 13-2 and had an emission spectra very similar to that of 13-2. Clone 17-3, on the other hand, had a much more red shifted emission spectra with a maximum at 550 nm (FIG. 16). Clone 2-4 had the most unusual spectra with an emission peak in the blue range at 460 nm (FIG. 16). This is unusual, because all blue shifted GFP-variants to date have evolved from a removal of the phenolate by a mutation of tyrosine to either phenylalanine or tryptophan. Therefore, it was not known if a phenol-containing fluorophore was even capable of bright blue fluorescence because of the dramatic drop in the phenolic pK$_a$ during excitation. Both of clones 18-16 and 17-17 had similar emissions to 23-11, with a peak around 535 nm.

Example 14—Synthesis of Fluorophores Bearing Modification to the Benzylidene Ring and Identification of Aptamers A second approach that may be used for generating a spectrum of different aptamer-fluorophore complexes is to modify the fluorophore itself. Large changes were already observed in both excitation and emission spectra by switching the ortho-methoxy groups of DMHBI with fluoro groups. Thus, it was believed that further modifications to the benzylidene portion of the fluorophore would result in more spectral diversity.

A small collection of different benzaldehydes was purchased and their absorbance spectra were measured to identify those with the most interesting spectral shifts. These starting aldehydes included 3,4,5-trimethoxy-, 3,4,5-trihydroxy-, 3,4-dihydroxy-, 4-cyano-, 4-mercapto-, 4-dimethylamino-, 3-nitro-4-hydroxy-, 2-nitro-4-hydroxy-, and 3,5-dichloro-4-hydroxy-benzaldehyde. The primary goal of this evaluation was to creating fluorophores with more red-shifted emission, because that would be particularly desirable for live cell imaging. The majority of these above mentioned compounds, however, produced blue-shifted absorbance spectra relative to DMHBI and DFHBI. While these fluorophores and their aptamers would nevertheless be useful, as demonstrated in the preceding examples with DMHBI and DFHBI, they would not satisfy the primary goal of this analysis. Because of this, the only compound selected for further investigation was the 4-dimethylaminobenzyaldehyde.

4-dimethylaminobenzylidene-5-imidazolinone (DMABI) (FIG. 17A) was synthesized in three steps. The first was an azalactone formation with N-acetylglycine as described in Example 1. However, the second step did not proceed smoothly. Repeated attempts to react with methylamine under alkaline condition did not result in the recyclized imidazolinone product. Instead, the primary products were a mix between the amide and ethyl ester open rings. Thus, to avoid the side reaction with ethanol, the aminolysis was performed in dioxane under refluxing conditions. After 1 hour, the solvent was removed and Nuclear Magnetic Resonance (NMR) confirmed over 95% purity of the resulting amide. Without further purification, the material was then recyclized in dry dichloromethane (DCM) with lutidine and Trimethylsilyl trifluoromethanesulfonate (TMSOtf). An analogous synthesis was also used to make the hexylamine-modified version of DMABI, which was then coupled to NHS-agarose as described in Example 2.

SELEX was performed with the partially structured RNA library in conditions similar to those used in the selection of DFHBI aptamers (Example 10). Screening was performed for 8 rounds and resulted in the identification of 7 unique sequences that increased the fluorescence of DMABI. Although there was some slight variation in fluorescence spectra between different clones, all aptamers to DMABI displayed an excitation maximum between 475-485 nm and an emission maximum between 505-515 nm. There were also some variations in fluorescence intensities of the different clones, with the brightest clone, 15-1 (FIG. 17B), being approximately equal to the intensity of 13-2-5. The sequences for these aptamers to DMABI are presented below by their encoding DNA sequences:

Clone 19-4,
(SEQ ID NO: 45)
where N at each position is C or T
GGGAGACGCAACTGAATGAACGAATAGGTGGAGGTTGCNCTGTTTTCTGC

TTCGGCAGGTTAAAGATTGGTACTCATCACGGTGTCCGTAACTAGTCGCG

TCAC

Clone 19-10,
(SEQ ID NO: 46)
where N at each position is C or T
GGGAGACGCAACTGAATGAACAGTTTCGTGCAGTTTGAAATGTAGGCTGC

TTCGGCAGGATAGGTGTGGAGGTGGATGTCCGGGTCCGTAACTAGTCGCG

TCAC

Clone 9-1,
(SEQ ID NO: 47)
where N at each position is C or T
GGGAGACGCAACTGAATGAACCCTGAAAAGAGGGAAGGCCTGGNTTGCTG

CTTCGGCAGGGGATTGATCAGGGTGCACGTTGCTGTCCGTAACTAGTCGC

GTCAC

Clone 9-6,
(SEQ ID NO: 48)
where N at each position is C or T
GGGAGACGCAACTGAATGAAGCCTTGAAATAGTAGTGATCGAGTGGCTGC

TTCGGCAGACTCTGAGTGTGGCTATACGTGATCGTCCGTAACTAGTCGCG

TCAC

Clone 11-3,
(SEQ ID NO: 49)
where N at each position is C or T
GGGAGACGCAACTGAATGAAAAAGTGGTATTTNAAATTCNANTTANCTGC

TTCGGCAGACGACGGGGGGGCNNGTNTTGGANGATCCGTAACTAGTCGCG

TCAC

Clone 15-1,
(SEQ ID NO: 50)
where N at each position is C or T
GGGAGACGCAACTGAATGAATGTNGCATAATTGANGGANGATNCATGCTG

CTTCGGCAGTTGGGTGTAAAAATGGAANGAGGTCNTATCCGTAACTAGTC

GCGTCAC

Clone 8-4,
(SEQ ID NO: 51)
where N at each position is C or T
GGGAGACGCAACTGAATGAATCCAGGGGTGGTCGGTGGNNGGAGCGCTGC

TTCGGCAGTGAGCTGGGGAGTTCAGTCAATGTGGTCCGTAACTAGTCGCG

TCAC

Example 15—Identification of RNA Aptamers for o-HBDI

There have been a number of attempts to modify the chemical structure of the original HBI chromophore in an effort to alter its photophysics and to model the effect of mutations in the chromophore-forming residues of GFP. Several of these reports have focused on making red-shifted variants of the chromophore. For example, Tonge and coworkers described the synthesis and spectroscopic characterization of 4-hydroxybenzylidene imidazolinone (HBDI) derivatives containing olefinic substituents on the imidazolinone ring (He et al., "Synthesis and Spectroscopic Studies of Model Red Fluorescent Protein Chromophores," Org. Lett. 4(9):1523-26 (2002), which is hereby incorporated by reference in its entirety). However, even the most red-shifted of these compounds, 4-hydroxybenzylidene-1-methyl-2-penta-1,3-dien-1-yl-imidazolinone, had an emission maxima of only 523 nm in neutral aqueous conditions. This small red-shift combined with the increased non-polarity of the olefinic substituents made these compounds a poor starting point.

Another more recent report showed that the o-hydroxy derivative of HBDI (o-HBDI) (FIG. 18A) has a strongly red shifted emission spectrum compared to the p-hydroxy form (Chen et al., "Ortho Green Fluorescence Protein Synthetic Chromophore; Excited-state Intramolecular Proton Transfer via a Seven-membered-ring Hydrogen-bonding System," *J. Am. Chem. Soc.*, 129(15):4534-4535 (2007), which is hereby incorporated by reference in its entirety). This large red shift to emission maxima of 605 nm is due to an intramolecular proton transfer between the o-OH and the imine nitrogen on the imidazolinone ring. This large red shift is interesting. Therefore free and agarose-bound versions of o-HBDI were synthesized and RNAs against this molecule were selected. After 8 rounds of SELEX and screening, four unique sequences of RNA were selected that bound to and increased the fluorescence of o-HBDI. The aptamers isolated from this SELEX are presented below by their encoding DNA sequences:

```
Clone 2-6,
                                          (SEQ ID NO: 52)
where N at each position is C or T
GGGAGACGCAACTGAATGAAAATGGCAAAATATTCGAGAANCTGGTCTGC

TTCGGCAGGATTCTCCAAGGGGTAGATCGTGTATTCCGTAACTAGTCGCG

TCAC

Clone 2-18,
                                          (SEQ ID NO: 53)
where N at each position is C or T
GGGAGACGCAACTGAATGAAAATGTNNNATNCGAGNCNGNATTNAGCTGC

TTCGGCAGAANGNTCTCCCANAGCTNNTGNCAAATCCGTAACTAGTCGCG

TCAC

Clone 8-9,
                                          (SEQ ID NO: 54)
where N at each position is C or T
GGGAGACGCAACTGAATGAAAATGTATAGTCGGATGTGCNGANTNNACTG

CTTCGGCAGCTTAGATGTATGCAGCTGCTCGGGAGTCCGTAACTAGTCGC

GTCAC

Clone 8-20
                                          (SEQ ID NO: 55)
GGGAGACGCAACTGAATGAATCTCCGTGTCAGGGCAGAGCAGGGCGCTGC

TTCGGCAGATAATGTATAGTCGGGATCGCTGAACTCCGTAACTAGTCGCG

TCAC
```

All sequences had excitation maxima at 400 nm and emission maxima at 590 nm (FIG. 18B). However, while the percentage increase in red fluorescence was quite dramatic for bound versus unbound o-HDBI, the total intensity of these RNA-fluorophore complexes was too weak to move forward with live cell imaging. One reason for this weak fluorescence may be due to the phenol/phenolate ratio of the fluorophore, as was the case with DMHBI fluorophore. Unfortunately, the intramolecular hydrogen bond responsible for the large red-shift relies on a protonated OH. Thus, lowering the $pK_a$ with electron withdrawing groups might result in brighter fluorescence but also impede the red shift.

The $pK_a$ for free o-HBDI was around 10. This strongly indicates that interactions between the hydrogen on the phenol and the imine nitrogen are occurring.

In an attempt to increase the brightness without affecting the hydroxyl $pK_a$ (and thus the intramolecular hydrogen bonding), the 4-dimethylamino version of o-HBDI (o-H-DMABI) (FIG. 18C) was synthesized to determine whether the amino moiety would further increase the brightness. When aptamers originally selected against either DMABI or o-HBDI were incubated with o-H-DMABI, the emission completely shifted back to ~500 nm with no red-shifted peaks (FIG. 18D).

Example 16—Synthesis of Fluorophores with N-Oximes and Generation of Aptamers

When the initial attempts to red shift the fluorescence of the fluorophores failed to produce robust and specific fluorescence complexes, a biomimetic approach was taken for fluorophore design. Most red shifted fluorophores, to date, have been based on the fluorophore of DsRed, a bright red fluorescent protein from coral (*Discosoma* spp.). DsRed has been tremendously useful as a complement to the widely utilized GFP, due to its significantly red-shifted excitation and emission maxima of 558 nm and 583 nm (FIG. 19B), respectively. Like GFP, the fluorophore in DsRed is formed by an autocatalytic, intramolecular cyclization of an internal tripeptide ($Q_{66}Y_{67}G_{68}$). However, while both the DsRed and GFP fluorophores share the same 4-HBDI core, the fluorophore in DsRed differs from that in GFP by the presence of an acylimino group at the 2-position of the imidazolinone ring (FIG. 19A). This adds to the conjugation of the fluorophore leading to the red-shifted spectroscopic properties of DsRed.

Due to the susceptibility of acylimines to nucleophilic attack, a synthetic fluorophore based on this structure is not feasible. Instead, a biomimetic fluorophore was designed using an N-oxime moiety in place of the imine (FIG. 19C). To prepare O-methyloxime derivatives, the phenolic hydroxyl group was first protected with tert-butyldimethyl-silyl chloride (TBS-Cl). To do this, imizalinone DMHBI or DFHBI (1 equiv) was dissolved in dry dichloromethane and treated with diisopropylethylamine (2 equiv) and TBS-Cl (2 equiv) and stirred at room temperature for 2 hours. The reaction was then concentrated and purified by column chromatography (silica, 4:1 ethyl acetate:hexanes). The $R_2$ group of TBS-protected product was then oxidized to an aldehyde by refluxing in dioxane with selenium dioxide, according to Yampolsky et al. ("Synthesis and Properties of the Red Chromophore of the Green-to-Red Photoconvertible Fluorescent Protein Kaede and Its Analogs," *Bioorganic Chem.* 36(2):96-104 (2008), which is hereby incorporated by reference in its entirety). After 1 hr the solution was carefully decanted from the selenium solid, concentrated and used directly in the next step. In the final step aldehyde (1 equiv) was dissolved in dry dimethylformamide and to this solution was added pyridine (2 equiv) and methoxyamine hydrochloride (2 equiv), and the mixture was stirred at room temperature over night. The reaction was then diluted in ethyl acetate, washed with 1 M HCl, water and saturated aqueous NaCl. The solutions was then concentrated and purified by column chromatography (silica, 20:1 dichloromethane:methanol).

SELEX for RNAs against this fluorophore resulted in a pool of aptamers that elicit fluorescent increases in this fluorophore (FIG. 19D).

Example 17—Rational Design of RNA Sensors for ATP, Adenosine, and cGMP

A tool used in biotechnology and biomedical research is fluorescence resonance energy transfer (FRET)-based sensors that report on the spatial and temporal localization of small molecules in cells. FRET-based sensors have been developed for numerous intracellular signaling molecules such as cAMP, calcium, hydrogen peroxide, $IP_3$, $PIP_2$, and numerous other important intracellular signaling molecules (Medintz, "Recent Progress in Developing FRET-based Intracellular Sensors for the Detection of Small Molecule Nutrients and Ligands," *Trends Biotechnol.* 24(12):539-42 (2006), which is hereby incorporated by reference in its entirety). A critical requirement for these sensors is that there must exist a protein that can specifically bind to the molecule and undergo a conformational change upon binding. FRET sensors typically are fusion proteins that comprise a small molecule-sensing domain and genetically-encoded FRET pairs, such as CFP and YFP (Medintz, "Recent Progress in Developing FRET-based Intracellular Sensors for the Detection of Small Molecule Nutrients and Ligands," *Trends Biotechnol.* 24(12):539-42 (2006), which is hereby incorporated by reference in its entirety). Small molecule binding results in a change in the proximity of the FRET pairs, which alters the FRET. This approach is useful as long as a protein exists which binds the small molecule, and that protein undergoes a conformational change. Additionally, sophisticated microscopic techniques are needed when the change in FRET between the bound and unbound form is small (Medintz, "Recent Progress in Developing FRET-based Intracellular Sensors for the Detection of Small Molecule Nutrients and Ligands," *Trends Biotechnol.* 24(12):539-42 (2006), which is hereby incorporated by reference in its entirety).

A major area of endeavor in chemical and biomedical research is the development of simple, sensitive, and specific sensors to assay for analytes in vitro and in vivo. A simple and repeatable approach for generating analyte sensors could have a substantial impact on many aspects of biomedical research and biotechnology, including studies of cell signaling and in drug screening.

Because of the above mentioned limitation in current FRET-based sensors, it would be better to generate an approach that would allow the sensing of essentially any small molecule analyte. The rational approach would be to generate RNA aptamers in which small molecule binding switches on DFHBI fluorescence. There is considerable precedent for the design of small molecules affecting the function of RNAs, including small molecule-regulated ribozymes (Tang et al., "Rational Design of Allosteric Ribozymes," *Chem Biol.* 4(6):453-9 (1997); Soukup et al., "Design of Allosteric Hammerhead Ribozymes Activated by Ligand-induced Structure Stabilization," *Structure* 7(7): 783-91 (1999), each of which is hereby incorporated by reference in its entirety), small molecule-regulated transcriptional activators (Buskirk et al., "In vivo Evolution of an RNA-based Transcriptional Activator," *Chem Biol.* 10(6): 533-40 (2003), which is hereby incorporated by reference in its entirety), and small molecules that affect the fluorescence of malachite green-binding aptamers (Stojanovic et al., "Modular Aptameric Sensors," *J Am Chem Soc.* 126(30): 9266-70 (2004), which is hereby incorporated by reference in its entirety). These approaches typically rely on the destabilization of a critical stem or stem loop which is replaced by a weakened stem fused to an aptamer or to the analyte to be sensed. Therefore, in the absence of analyte, the stem remains only partially closed and reduces the functionality of the RNA. However, upon fluorophore binding, the meta stable stem is brought together and the structure is reinforced and the function of the RNA is restored.

Because the aptamers to DFHBI were selected using a library with constant stem-loop region, this stem loop is not likely to interact with the fluorophore directly. Instead, the stem loop merely plays a structural role. In fact, when this loop was replaced with another very stable stem loop, minimal loss in fluorescence signal was detected for either 24-1 or 24-2. 24-1 was chosen for further analysis because the secondary structure prediction showed this stem loop to close a bulge, whereas in 24-2 the stable stem loop was followed by more stem. It was found that in 24-1 the stem-loop could essentially be changed to any nucleotide combination as long as a stem-forming sequence was retained (FIG. 20A). Additionally, the loop could be changed to any nucleotide sequence without affecting the fluorescence.

A requirement for a folded stem was an important finding since conditional folding of a stem was previously exploited to make flavin mononucleotide (FMN), ATP, and theophylline-regulated ribozymes (Tang et al., "Rational Design of Allosteric Ribozymes," *Chem Biol.* 4(6):453-9 (1997); Soukup et al., "Design of Allosteric Hammerhead Ribozymes Activated by Ligand-induced Structure Stabilization," *Structure* 7(7):783-91 (1999), each of which is hereby incorporated by reference in its entirety). In these analyte-regulated ribozymes, a ribozyme stem was replaced with a stem from the analyte-binding aptamer (Soukup et al., "Design of Allosteric Hammerhead Ribozymes Activated by Ligand-induced Structure Stabilization," *Structure* 7(7): 783-91 (1999), which is hereby incorporated by reference in its entirety). The stability of the stem was reduced with G-U and A-U base pairs, so that its folding could be readily influenced by the folded state of the aptamer—like many aptamers, these aptamers are largely unfolded when analyte is not bound, but become folded into a compact structure upon analyte binding. The presence of analyte causes the aptamer to fold and to bring together the strands that form the stem, thereby augmenting ribozyme activity.

It was predicted that the common stem-loop of aptamer 24-1 could be used as an entry point for another aptamer. To do this, weakening mutations were introduced into the stem to assess their effect on fluorescence. These weakening mutations were introduced along with an aptamer for adenosine (FIG. 20B, marked *), resulting in a fusion 24-1:ATP aptamer (SEQ ID NO: 32) that could be employed with DFHBI.

Incubation of these fusion RNAs with or without ATP in the presence of DFHBI revealed that they acted as potent fluorescent sensors of ATP (FIG. 21A). The most potent sensor resulted from a single mutation in the stem by switching a G-C base pair to a less stable G-U pair (FIG. 20B). 24-1 was also fused to several aptamers with varied weakened stems. This resulted in the discovery of sensors for both an ATP (specific of triphosphate) and cyclic GMP with impressive increases in fluorescence intensity upon addition of analyte (FIG. 21B-D).

Example 18—Rational Design of ATP Sensor Using Aptamer 13-2

The mutagenesis studies described in Example 8 confirmed that stem loop A of aptamer 13-2 (see FIG. 22A) could be mutated as long as a stem-forming sequence was retained. Using the same approach identified in Example 17

(for aptamer 24-1), stem-loop A was used as an entry point for introducing an ATP aptamer along with stem destabilization. Simply fusing an ATP-binding aptamer to 13-2 via a modified stem A resulted in a fusion 13-2:ATP aptamer (SEQ ID NO: 62) that could be employed with DMHBI.

The fusion 24-1:ATP aptamer behaved as a sensor that responded to an increase in ATP concentration with a corresponding increase in fluorescence (FIG. 22B). These data demonstrate that 13-2 can be converted into an analyte-regulated fluorescence sensor.

Example 19—Generation of De Novo Fluorescent Sensors Using SELEX

The rationale design approach, described in Examples 17 and 18, can be used for development of simple, sensitive, and specific sensors to assay for analytes in vitro and in vivo. However, rational design requires knowledge of the sequence and predicted structures of the aptamers (to be fused), and does not necessarily predict the most sensitive fusion construct. A method for generating novel sensors to any molecule, even those without a pre-existing aptamer, would be a substantial advancement. This development would allow detection of molecules in solution or when expressed in cells.

A SELEX-based approach can be used to discover analyte-regulated fluorescent sensors. For example, the SELEX-based approach can use the 24-1 aptamer scaffold as the basis for a randomized library. In this library, most of the 24-1 structure can be retained, except for the region encompassing the critical stem-loop, in which a 40 nt randomized region can be inserted (FIG. 23A).

A design strategy for such selection is depicted schematically in FIG. 23B. In the first step of this strategy, RNAs can be "precleared" by passing the RNAs over DFHBI agarose. This will remove all library members that retain constitutive DFHBI-binding activity. In the next step, the flow-through could be rebound to DFHBI agarose, except that the analyte of interest will be added to the incubation buffer. All washes will also contain analyte. After washing, the elution will occur in the same buffer, except that no analyte will be present. Thus, any RNAs whose binding to DFHBI is dependent on analyte will elute. These RNAs will be recovered and used for subsequent rounds of SELEX to enrich for analyte-regulated sensors. The fluorescence of each pool will be tested as above in the presence of DFHBI with or without analyte, and individual clones that exhibit analyte-dependent fluorescence can be therefore isolated.

It is important that negative selection is used to ensure that the sensors do not respond to structurally related molecules. For example, sensors developed against ATP should not detect adenosine, ADP, AMP, or NAD. To do this, these molecules can also be introduced in the elution buffer, so that if they promote DFHBI binding they will be retained on the DFHBI agarose (whereas sensor constructs that are unaltered by these structurally related molecules will elute).

As a proof of principle, the above selection strategy was performed using either 1 µM nicotinamide adenine dinucleotide (NAD) or 1 µM biotin as the analyte of interest. After 8 rounds, the fluorescence of the library was measured at each round in the presence or absence of either NAD or biotin. Until round 4, for both NAD and biotin selections there was essentially no change in fluorescence upon addition of the respective analyte. However, by round 5, subtle increases started to emerge in the fluorescence upon analyte addition for both selections. This increase clearly demonstrates the existence of a clone or several clones capable of eliciting fluorescence of DFHBI only in the presence of a specific analyte. This increase had leveled out by round 6-8. Screening of these pools of clones and identification of the individual clones, using the methods described in the present invention, will result in identification of aptamers that acts as analyte-regulated fluorescent sensors (FIG. 24A).

The selected pool of biotin-specific sensor molecules was titrated against increasing concentrations of biotin, resulting in a linear increase in fluorescence emissions by the DFHBI: aptamer pool (FIG. 24B). The measured $EC_{50}$ was 400 µM.

The selected pool of NAD-specific sensor molecules was titrated against increasing concentrations of NAD, resulting in a linear increase in fluorescence emissions by the DFHBI: aptamer pool (FIG. 24C). The measured $EC_{50}$ was 100 µM.

These sensors will be sequenced, and may be subjected to mutational studies to enhance their properties.

Example 20—Development of Total Internal Reflection Fluorescence (TIRF) Microscopy Detection Platform To simplify detection of fluorescence following sensor binding to the fluorophore, a prism-based total internal reflection fluorescence (TIRF) microscopy system was implemented for the detection of aptamer 13-2 binding to DMHBI (FIG. 25A). The set-up and principles of TIRF are well known. The equipment includes a waveguide through which a light source transmits a propagated signal, a flow cell that is formed on one side of the waveguide, and a microscope along with camera and other imaging equipment on the opposite side of the waveguide. In generating the results shown in FIG. 25B, glass slides were used as the waveguide and DMHBI was coupled to the glass surface using the hexylamine derivative and standard glass-coupling protocols. The fluorescence of the glass surface is negligible in the presence of control RNA, but is markedly enhanced when exposed to aptamer 13-2 (FIG. 25B, compare left and right images). This demonstrates the ability of TIRF to detect low levels of RNA in solution.

This TIRF detection system will afford the preparation and use of protein microarrays. In particular, microarrays could be used to assay a set of specific proteins, such as clinically relevant biomarkers, or could be used to assay large sections of the proteome, such as proteins of specific functional classes. Current protein microarray technologies requires complex sample preparation, because proteins from biological samples have to be labeled with fluorescent dyes, such as Cy5-NHS, in order for the protein to be detected when its binds to a microarrayed antibody. This is problematic since this labeling procedure could also affect the epitope recognized by the antibody. However, these problems can be overcome in a TIRF-based microarray system of the present invention. In particular, the fluorescent sensors described in the preceding examples can overcome these technical challenges due to: (1) their low cost; (2) ease with which oligonucleotides can be coupled to microarrays; (3) the ability to reliably synthesize homogeneous preparation of oligonucleotides, which is a challenge with antibodies; (4) the increased stability of oligonucleotides compared to antibodies; (5) the highly specific nature of aptamer-protein interactions, which typically involve large surfaces rather than short epitopes as with antibodies; and (6) the ease of sample preparation—fluorescent signaling obtained using the sensors of the present invention do not require the sample processing step of fluorescent dye tagging the protein of interest. Binding of the protein to the sensor is sufficient to elicit a fluorescent signal, dramatically simplifying the analysis of protein mixtures.

Until recently, no microarray scanners used TIRF. However, advances in technology (e.g., objectives) and concomitant cost reductions have resulted in an emergence of TIRF-based assays and devices. TIRF-based scanners result in exceptionally higher sensitivity (e.g. <5 fluorophores/$\mu m^2$ for the Genorama QuattroImager) than standard scanners (100-200 fluorophores/$\mu m^2$). The protein microarrays of the invention will take advantage of the sensitivity of TIRF. If the density of a sensor in a microspot is 106 $\mu m^2$, and the $EC_{50}$ of the sensor is 10 nM, protein levels at 1 $\mu$M would give a signal of 100 fluorophores/$\mu m^2$, which is significantly higher than the sensitivity level of TIRF. Thus, as seen, TIRF can be used to measure fluorescent signals on a conventional DNA microarray. TIRF is especially useful for detection of low levels of analytes.

TIRF can also be used to enhance the signal of fluorescent aptamers when expressed in cells. If RNA aptamers are expressed in cells and then localized to the membrane, TIRF can be used to detect on the membrane bound RNAs that bind to the dye. This method reduces the problem of autofluorescence in the cell and allows the researcher to detect much weaker signals. One strategy to localize the RNA aptamers to the plasma membrane of cells was performed using the MS2 RNA sequence. To do this, aptamer 24-1 was expressed with an MS2 RNA sequence tag. MS2 RNA is a bacteriophage RNA that binds specifically and tightly to an MS2-binding protein only found in bacteriophages (SenGupta et al., "Three-hybrid System to Detect RNA-protein Interactions in vivo," *Proc. Natl. Acad. Sci USA* 93:8496-8501 (1996), which is hereby incorporated by reference in its entirety).

The MS2 binding protein can be localized to the cell membrane by tagging the protein with an N-terminal palmitoylation (palm) sequence (Skene and Virag, "Posttranslational Membrane Attachment and Dynamic Fatty Acylation of a Neuronal Growth Cone Protein, GAP-43," *J. Cell Biol* 108:613-625 (1989), which is hereby incorporated by reference in its entirety). This was confirmed by expressing MS2 binding protein tagged with GFP in cells with or without the palm sequence. FIG. 26A shows that GFP signal is relocated to the membrane of HEK 293 cells only when the palm sequence is present. Thus, coexpression of both palm-MS2 binding protein and 24-1-MS2 RNA sensor, the MS2 RNA and binding protein will interact and recruit the RNA to the cell membrane. RNAs were expressed from a Pol III promoter for the 5S ribosomal RNA and also contain the first ~100 nucleotides of the 5S RNA which act as a localization element to ensure that the RNA gets exported to the cytosol were it can interact with the MS2 binding protein (Paul et al., "Localized Expression of Small RNA Inhibitors in Human Cells," *Mol. Ther.* 7(2):237-247 (2003), which is hereby incorporated by reference in its entirety). This was confirmed by expressing both the protein and RNA fusions in HEK 293 cells and performing a subcellular fractionation to separate membrane fragments from the cytosolic fractions. The membrane and cytosolic fractions were then compared using a Western blot (using anti-GFP) and a Northern blot with a probe to 24-1. As can be seen in FIG. 26B, GFP localized to the membrane only in palm-positive cells. As can be seen in FIG. 26C, 24-1 RNA is enriched in the membrane of cells which express palm-MS2 binding protein when compared to cells that express only MS2-binding protein. Future sensors to target molecules can be tagged to membranes as is shown in the scheme in FIG. 27.

Example 21—Using Directed Evolution to Modify Aptamer Sequences

Another method that may be used for modulating the fluorescence emission profile of a particular fluorophore is directed evolution of the aptamer that induces fluorescence of the fluorophore. The directed evolution process is described by Shaner et al., "Improved Monomeric Red, Orange and Yellow Fluorescent Proteins Derived from *Discosoma* sp. Red Fluorescent Protein," *Nat Biotechnol.* 22:1567-1572 (2004), which is hereby incorporated by reference in its entirety. Basically, the process as described by Shaner et al. involves the use of directed evolution using random mutagenesis and FACS screening to obtain GFP variants with a range of fluorescent colors. Applying this to the present invention, the fluorescence of 13-2-DMHBI complexes will be optimized using this approach, and both red- and blue-shifted 13-2 variants will be developed by multiple rounds of expressing mutagenized 13-2 libraries in Jurkat cells and selecting those cells with desirable fluorescence emission properties as described by Shaner et al.

Another analogous approach for screening that does not use FACS is to use doped libraries of, for example, 13-2, and pick clones based on their wavelength instead of their intensity. The most red-shifted clone can be picked and used to prepare a new doped library. This process will be repeated several times, until the aptamer-fluorophore complex emission is clearly in the red channel. Each round may result in a shift of 5-10 nm, which is the rate that Shaner et al. reported in their directed evolution experiments. It is not unreasonable that RNA-DMHBI complexes could have a range of fluorescence emissions—a precedent for this is the phenomenon of "spectral tuning" of opsins, in which the same chromophore, i.e. retinal, can absorb red, green, or blue light, based on chromophore microenvironment dictated by the specific opsin protein to which it is covalently coupled. Indeed, tuning of fluorophore emissions by a panel of aptamers was demonstrated in Example 13.

Together, these methods described above will be used to develop a set of fluorophores/aptamer complexes that may be used for SELEX experiments and eventually for visualizing aptamer-tagged RNAs in, for example, live-cell experiments.

Example 22—Mutational Study of the J Stem in Adenosine Sensor

The adenosine sensor described in Example 17, bearing the J Stem illustrated in FIG. 20B, was modified by replacement of the stem and assessment of fluorescent properties of the sensor molecules. In SEQ ID NO: 32, supra, the J2 Stem sequences are identified in bold typeface. Table 3 identifies the replacement sequences.

TABLE 3

Stem Replacements for Adenosine Sensor of SEQ ID NO: 32

| Stem name | Stem Sequence (5'-3') | Fluorescence (Rel to 24-1) |
|---|---|---|
| J2 (SEQ ID NO: 32) | GCTGC . . . GTAGC | 63% |

TABLE 3-continued

Stem Replacements for Adenosine Sensor of SEQ ID NO: 32

| Stem name | Stem Sequence (5'-3') | Fluorescence (Rel to 24-1) |
|---|---|---|
| J6 | GTTGT . . . GCAGC | 5% |
| H6 | GTGTGTG . . . CGTATGC | 58% |
| H6A | GTATGTG . . . CGGATGC | 10% |
| H6B | GTGCGTG . . . CGTGTGC | 24% |
| H6C | GTGAGTG . . . CGTTCGC | 63% |
| J2D | GTAATG . . . CGTTGC | 69% |

The J2 stem was one of the best stems in terms of retaining overall fluorescence while providing the desired adenosine responsiveness. The J2D stem achieved 69% of the fluorescence of aptamer 24-1. All of the stems allowed the sensor molecules to exhibit adenosine-responsive fluorescence.

Example 23—Methods for Use of RNA-Fluorophore Complexes to Visualize mRNAs in Cells and mRNA Trafficking in Axons Recently, it was discovered found that RhoA transcripts are localized to axonal growth cones and RhoA mRNA is translated in order to mediate the growth cone collapsing effect of Semaphorin 3A (Sema3A). RhoA transcripts are localized to axonal growth cones in granule structures and are found in filopodia as well as the axon (Wu et al., "Local Translation of RhoA Regulates Growth Cone Collapse," *Nature* 436:1020-1024 (2005), which is hereby incorporated by reference in its entirety). Using Sindbis viral constructs to express RhoA fusion RNAs, it was also discovered that RhoA is targeted to the growth cone via a targeting element located in the RhoA 3'UTR.

The aptamer:fluorophore complexes of the present invention will be used to monitor RhoA mRNA localization and trafficking in growth cones during axonal turning in response to gradients of Sema3A. The RhoA mRNA will be cloned into one or more plasmid constructs that allows the RhoA RNA o to be expressed as a fusion with an array of aptamer tags. A plurality of tandem 13-2 aptamer tags will be used. pcDNA3.1 will be used as the parent plasmid, with aptamer sequences cloned into the multiple cloning site, leaving sites available for cloning RhoA cDNA. The resulting plasmid constructs will be transfected into dorsal root ganglia (DRG) neurons.

The localization of the aptamer-RhoA fusion mRNA will be monitored using live-cell microscopy. Mattek glass-bottom dishes will be used for microscopy in an environmental chamber. To confirm that the RhoA fusion mRNA is expressed, the neurons will be fixed in situ hybridization will be performed using an aptamer-specific probe. It will be determined whether the localizations of fusion-RhoA mRNA seen under live-cell conditions mimic the endogenous localization seen in the in situ hybridization experiments. Since RhoA translation mediates the effects of Sema3A in the growth cone, RhoA granule movement will be monitored in neurons that have been stimulated with Sema3A. Sema3A is typically injected 100 µm away from an axon at flow rates of approximately 1 nl/min from a pico-syringe. Axons turn away from the syringe over the course of an hour. Since RhoA mediates cytoskeletal retraction at the side of the axon that is moving away from the cue, it is possible that RhoA mRNA may migrate to this side of an axon to position the subsequent protein in the correct region of the axon. Thus, the trafficking of tagged RhoA mRNA will be monitored in axons in which the micropipet is filled with Sema3A or vehicle. If Sema3A induces RhoA RNA trafficking to sites of growth cone collapse, it would demonstrate that the Sema3A receptor, PlexinA/neuropilin, signals the recruitment of mRNA, and would represent a new and unexpected signaling effector pathway for this receptor complex. Unlike an in situ hybridization experiment, live-cell imaging would allow for a determination if RhoA granules that appear on the collapsing edge of the growth cone are derived from pre-existing granules in the growth cone, or if they are derived from granules in the axon, or if they materialize from unbound mRNAs. Further, the temporal relationship between RhoA trafficking and turning can be established. Thus, the RNA visualization technology will enable the role of RhoA mRNA in axons to be established in a way not possible using in situ hybridization.

Example 24—Use of the NAD Sensor to Detect Dynamic Changes in NAD Levels in Cells The NAD sensor described in Example 19 will be used to detect dynamic changes in NAD levels in live cells. Recently, it has been shown that β-nicotinamide riboside and a series of related amide, ester, and acid nucleosides increase intracellular NAD levels between 20-270%, as measured by a HPLC assay (Yang et al., "Syntheses of Nicotinamide Riboside and Derivatives: Effective Agents for Increasing Nicotinamide Adenine Dinucleotide Concentrations in Mammalian Cells," *J Med Chem.* 50:6458-6461 (2007), which is hereby incorporated by reference in its entirety). Using the NAD sensor and these same NAD-inducing agents, it will be determined how quickly these compounds increase NAD levels, and how long these increases in intracellular NAD levels persist.

To achieve this, the NAD-responsive RNA sensor will be expressed in cells. Aptamers are usually expressed using plasmids from either Pol II or Pol III promoters and result in high cytoplasmic levels of aptamer RNA (Paul et al., "Localized Expression of Small RNA Inhibitors in Human Cells," *Mol Ther.* 7:237-247 (2003), which is hereby incorporated by reference in its entirety). HEK293 cells with plasmids that use each type of promoter will be utilized, and expression levels of the aptamer will be monitored by Northern blot. Plasmids that produce the highest levels of RNA aptamer will be used for NAD imaging.

Next, baseline fluorescence levels will be assessed in the absence and presence of DMHBI. Additionally, endogenous NAD levels will be inhibited with FK866, an inhibitor of nicotinamide phosphoribosyltransferase (Khan et al., "Nicotinamide Adenine Dinucleotide Metabolism as an Attractive Target for Drug Discovery," *Expert Opin Ther Targets.* 11:695-705 (2007), which is hereby incorporated by reference in its entirety). It is expected that inhibiting NAD levels will reduce fluorescence from the sensor. Next, the different amide, ester, and acid nucleoside derivatives of β-nicotinamide riboside will be tested for their effects. The proper functioning of the sensors will be established by the detection of an increase in total fluorescence upon treatment of transfected HEK293 cells with these NAD precursors. Since changes in fluorescence could reflect changes in cell volume, cells will be cotransfected with a plasmid expressing Azurite, a blue fluorescent protein. Green sensor fluorescence will be normalized to blue fluorescence. The time course and levels of green fluorescence will be monitored, and the NAD precursors that most rapidly increase NAD levels will be identified. These experiments will help to establish which of these compounds is most appropriate for supplementation purposes, and will form the basis for future studies that will measure NAD levels in neurons.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. A molecular complex comprising:
    (a) an imidazolinone fluorophore selected from the group consisting of 4-(3,5-dimethoxy-4-hydroxybenzylidene)-1,2-dimethoxy-imidazole-5-one (DMHBI), 3,5-difluoro-4-hydroxybenzylidene-1,2-dimethyl-imidizolan-5-one (DFHBI), 4-(4-dimethylamino)benzylidene)-1,2-dimethyl-imidazol-5-one (DMABI), and 4-(2-hydroxybenzylidene)-1,2-dimethyl-imidazole-5-one (o-HBDI); and
    (b) a nucleic acid aptamer molecule comprising, a first domain having a secondary structure, wherein the nucleic acid aptamer molecule binds specifically and directly to the imidazolinone fluorophore to form the molecular complex, such that upon exposure to radiation of a suitable wavelength, the imidazolinone fluorophore exhibits fluorescence that is enhanced as compared to fluorescence by the imidazolinone fluorophore in the absence of specific and direct binding by the nucleic acid aptamer molecule, such that:
        (i) when the imidazolinone fluorophore is DMHBI, the nucleic acid aptamer molecule that binds specifically and directly to the imidazolinone fluorophore to form the molecular complex is selected from the group consisting of SEQ ID NOS: 34-39 and 57-61;
        (ii) when the imidazolinone fluorophore is DFHBI, the nucleic acid aptamer molecule that binds specifically and directly to the imidazolinone fluorophore to form the molecular complex is selected from the group consisting of SEQ ID NOS: 42-44;
        (iii) when the imidazolinone fluorophore is DMABI, the nucleic acid aptamer molecule that binds specifically and directly to the imidazolinone fluorophore to form the molecular complex is selected from the group consisting of SEQ ID NOS: 45-51; and
        (iv) when the imidazolinone fluorophore is o-HBDI, the nucleic acid aptamer molecule that binds specifically and directly to the imidazolinone fluorophore to form the molecular complex is selected from the group consisting of SEQ ID NOS: 52-55.

2. The molecular complex according to claim 1, wherein the nucleic acid aptamer molecule further comprises a second domain that binds specifically to a target molecule that is distinct from the imidazolinone fluorophore.

3. The molecule complex according to claim 2, wherein the first domain binds to the imidazolinone fluorophore only after binding of the second domain to the target molecule, the molecular complex further comprising the target molecule bound by the second domain.

4. A host cell containing the molecular complex according to claim 1.

5. The molecular complex according to claim 1, wherein the nucleic acid aptamer molecule comprises a plurality of the first domains that bind the imidazolinone fluorophore.

6. The molecular complex according to claim 2, wherein the nucleic acid aptamer molecule comprises a plurality of the first domains that each bind to the imidazolinone fluorophore.

7. The molecular complex according to claim 2, wherein the nucleic acid aptamer molecule comprises a plurality of first and second domain concatemers.

8. The molecular complex according to claim 2, wherein the nucleic acid aptamer molecule comprises a nucleotide sequence selected from the group consisting of SEQ ID NO: 31, SEQ ID NO: 32, and SEQ ID NO: 33.

9. The molecular complex according to claim 3, wherein the target molecule is selected from the group consisting of adenosine triphosphate, cyclic guanosine monophosphate, biotin, nicotinamide, and nicotinamide adenine dinucleotide.

10. The molecular complex according to claim 3, wherein the target molecule is selected from the group consisting of proteins, nucleic acids, lipids, carbohydrates, hormones, cytokines, chemokines, metabolites, organic molecules, and metal ions.

11. The molecular complex according to claim 1, wherein the imidazolinone fluorophore is 3,5-difluoro-4-hydroxybenzylidene-1,2-dimethyl-imidizolan-5-one.

* * * * *

SEQUENCE LISTING

```
<160> NUMBER OF SEQ ID NOS: 62

<210> SEQ ID NO 1
<211> LENGTH: 114
<212> TYPE: RNA
<213> ORGANISM: Artificial
<220> FEATURE:
<223> OTHER INFORMATION: Aptamer 3-6, binds to DMHBI

<400> SEQUENCE: 1
gggagauacg cucuagaauu caauugcaug guggucuggg acagacgugu ggacggcaca      60
cagcgugagg cuuuggguggg uuauggcugu caugcgagau agcucgagca augc          114

<210> SEQ ID NO 2
<211> LENGTH: 69
<212> TYPE: RNA
<213> ORGANISM: Artificial
<220> FEATURE:
<223> OTHER INFORMATION: Aptamer 13-2, binds to DMHBI

<400> SEQUENCE: 2
gggcuauuuc uggaggggcg cuacaugaaa guggugguug ggugcggucg gagauagcuc      60
gagcaaugc                                                              69

<210> SEQ ID NO 3
<211> LENGTH: 60
<212> TYPE: RNA
<213> ORGANISM: Artificial
<220> FEATURE:
<223> OTHER INFORMATION: Aptamer 13-2 min, binds to DMHBI

<400> SEQUENCE: 3
gggcuauuuc uggaggggcg cuacaugaaa guggugguug ggugcggucg gagauagcuc      60

<210> SEQ ID NO 4
<211> LENGTH: 72
<212> TYPE: RNA
<213> ORGANISM: Artificial
<220> FEATURE:
<223> OTHER INFORMATION: Aptamer 2-4, binds to DMHBI

<400> SEQUENCE: 4
ugaaaccuag aguuaugcca ggcucugagc cugcuucggc aggugcuaug aucgccagcg      60
guaugcaguc cg                                                          72

<210> SEQ ID NO 5
<211> LENGTH: 72
<212> TYPE: RNA
```

```
<213> ORGANISM: Artificial
<220> FEATURE:
<223> OTHER INFORMATION: Aptamer 4-19, binds to DMHBI
<220> FEATURE:
<221> NAME/KEY: misc_feature
<222> LOCATION: (27)..(27)
<223> OTHER INFORMATION: N is C or U

<400> SEQUENCE: 5
ugaaaugaca guacagugga gggugcngua cugcuucggc agggaagggg cgcuguucuu      60
gucucauauc cg                                                         72

<210> SEQ ID NO 6
<211> LENGTH: 72
<212> TYPE: RNA
<213> ORGANISM: Artificial
<220> FEATURE:
<223> OTHER INFORMATION: Aptamer 17-3, binds to DMHBI
<220> FEATURE:
<221> NAME/KEY: misc_feature
<222> LOCATION: (28)..(28)
<223> OTHER INFORMATION: N is C or U

<400> SEQUENCE: 6
ugaagagcag uagcgaguag uucacaanag cugcuucggc aggaucuugu aggaaguaaa      60
ugugcaaauc cg                                                         72

<210> SEQ ID NO 7
<211> LENGTH: 74
<212> TYPE: RNA
<213> ORGANISM: Artificial
<220> FEATURE:
<223> OTHER INFORMATION: Aptamer 17-17, binds to DMHBI
<220> FEATURE:
<221> NAME/KEY: misc_feature
<222> LOCATION: (6)..(7)
<223> OTHER INFORMATION: N is C or U
<220> FEATURE:
<221> NAME/KEY: misc_feature
<222> LOCATION: (22)..(22)
<223> OTHER INFORMATION: N is C or U
<220> FEATURE:
<221> NAME/KEY: misc_feature
<222> LOCATION: (26)..(27)
<223> OTHER INFORMATION: N is C or U
<220> FEATURE:
<221> NAME/KEY: misc_feature
<222> LOCATION: (45)..(45)
<223> OTHER INFORMATION: N is C or U
<220> FEATURE:
<221> NAME/KEY: misc_feature
<222> LOCATION: (57)..(57)
<223> OTHER INFORMATION: N is C or U
<220> FEATURE:
<221> NAME/KEY: misc_feature
<222> LOCATION: (61)..(61)
<223> OTHER INFORMATION: N is C or U
<220> FEATURE:
<221> NAME/KEY: misc_feature
<222> LOCATION: (64)..(64)
<223> OTHER INFORMATION: N is C or U
<220> FEATURE:
<221> NAME/KEY: misc_feature
<222> LOCATION: (67)..(67)
<223> OTHER INFORMATION: N is C or U

<400> SEQUENCE: 7
ugaaannaaa uauucgggau anauannauu acugcuucgg caganagcgg uuaauunuug      60
naanucnaau cccg                                                       74
```

```
<210> SEQ ID NO 8
<211> LENGTH: 73
<212> TYPE: RNA
<213> ORGANISM: Artificial
<220> FEATURE:
<223> OTHER INFORMATION: Aptamer 18-16, binds to DMHBI
<220> FEATURE:
<221> NAME/KEY: misc_feature
<222> LOCATION: (5)..(5)
<223> OTHER INFORMATION: N is C or U
<220> FEATURE:
<221> NAME/KEY: misc_feature
<222> LOCATION: (19)..(19)
<223> OTHER INFORMATION: N is C or U
<220> FEATURE:
<221> NAME/KEY: misc_feature
<222> LOCATION: (29)..(29)
<223> OTHER INFORMATION: N is C or U
<220> FEATURE:
<221> NAME/KEY: misc_feature
<222> LOCATION: (53)..(53)
<223> OTHER INFORMATION: N is C or U
<220> FEATURE:
<221> NAME/KEY: misc_feature
<222> LOCATION: (67)..(67)
<223> OTHER INFORMATION: N is C or U
<220> FEATURE:
<221> NAME/KEY: misc_feature
<222> LOCATION: (69)..(69)
<223> OTHER INFORMATION: N is C or U
<220> FEATURE:
<221> NAME/KEY: misc_feature
<222> LOCATION: (72)..(72)
<223> OTHER INFORMATION: N is C or U

<400> SEQUENCE: 8
ugaanggacu cgucuggcng gaugggcgng ugguacugcu uucgggcagg aunggguaua      60
acgguanang cnc                                                        73

<210> SEQ ID NO 9
<211> LENGTH: 72
<212> TYPE: RNA
<213> ORGANISM: Artificial
<220> FEATURE:
<223> OTHER INFORMATION: Aptamer 23-7, binds to DMHBI

<400> SEQUENCE: 9
ugaaaugaca guacagugga gggugcggua cugcuucggc agggaagggg cgcuguucuu      60
gucucauauc cg                                                         72

<210> SEQ ID NO 10
<211> LENGTH: 104
<212> TYPE: RNA
<213> ORGANISM: Artificial
<220> FEATURE:
<223> OTHER INFORMATION: Aptamer 23-11, binds to DMHBI

<400> SEQUENCE: 10
gggagacgca acugaaugaa augacaguac aguggagggu gcgguacugc uucggcaggg      60
aaggggcgcu guucuugucu cauauccgua acuagucgcg ucac                     104

<210> SEQ ID NO 11
<211> LENGTH: 109
<212> TYPE: RNA
<213> ORGANISM: Artificial
<220> FEATURE:
<223> OTHER INFORMATION: Aptamer 12-2-1, binds to DMHBI

<400> SEQUENCE: 11
```

```
ggguauccgg aaucuuauac auuguuaugu cuggaggggc gccgcaugaa cgcgguggug    60
aggugcgguc ggauauaacu ggggagugc aagagucuga gcacacugg              109
```

<210> SEQ ID NO 12
<211> LENGTH: 109
<212> TYPE: RNA
<213> ORGANISM: Artificial
<220> FEATURE:
<223> OTHER INFORMATION: Aptamer 13-2-3, binds to DMHBI

<400> SEQUENCE: 12

```
ggguauccgg aaucuuauac auugcuauuu cuggaggggc gccccaugaa aggggugguu    60
gagagcgguc ggagauagcg gaaacagugc aagagucuga gcacacugg              109
```

<210> SEQ ID NO 13
<211> LENGTH: 109
<212> TYPE: RNA
<213> ORGANISM: Artificial
<220> FEATURE:
<223> OTHER INFORMATION: Aptamer 13-2-4, binds to DMHBI

<400> SEQUENCE: 13

```
ggguauccgg aaucuuauac auugcuauug uuggaggggc gcuacgugaa aguggugguu    60
cggugcgguc ggcaauagcu cguauagugc aagagucuga gcacacugg              109
```

<210> SEQ ID NO 14
<211> LENGTH: 109
<212> TYPE: RNA
<213> ORGANISM: Artificial
<220> FEATURE:
<223> OTHER INFORMATION: Aptamer 13-2-5, binds to DMHBI

<400> SEQUENCE: 14

```
ggguauccgg aaucuuauac auugcucugu uuggaggggc gcuacuuuca aguagugguu    60
gagugcgguc gaacagagcu ugggcguugc aagagucuga gcacacugg              109
```

<210> SEQ ID NO 15
<211> LENGTH: 97
<212> TYPE: RNA
<213> ORGANISM: Artificial
<220> FEATURE:
<223> OTHER INFORMATION: Aptamer 13-2-5-min, binds to DMHBI

<400> SEQUENCE: 15

```
ggguauccgg aaucuuauac auugcucugu uuggaggggc gcuacuuuca aguagugguu    60
gagugcgguc gaacagagcu ugggcguugc aagaguc                            97
```

<210> SEQ ID NO 16
<211> LENGTH: 106
<212> TYPE: RNA
<213> ORGANISM: Artificial
<220> FEATURE:
<223> OTHER INFORMATION: Aptamer 24-4, binds to DFHBI

<400> SEQUENCE: 16

```
gggagacgca acugaaugaa cggggtaaau aggcgugggu cgggccugc uucggcaguu    60 gagugugaga gcgaacucug uaguuccgcg uaacuagucg cgucac                 106
```

<210> SEQ ID NO 17
<211> LENGTH: 106
<212> TYPE: RNA
<213> ORGANISM: Artificial

```
<220> FEATURE:
<223> OTHER INFORMATION: Aptamer 24-1, binds to DFHBI

<400> SEQUENCE: 17
gggagacgca acugaaugaa ccuguagaac gacuuggucg ggucagcugc uucggcagcu    60
ucgagaauag agugugggu cguauccgcg uaacuagucg cgucac                  106

<210> SEQ ID NO 18
<211> LENGTH: 106
<212> TYPE: RNA
<213> ORGANISM: Artificial
<220> FEATURE:
<223> OTHER INFORMATION: Aptamer 24-2, binds to DFHBI

<400> SEQUENCE: 18
gggagacgca acugaaugaa auggugaagg acggguccag guguggcugc uucggcagug    60
cagcuuguug aguagagugu gagcuccgcg uaacuagucg cgucac                  106

<210> SEQ ID NO 19
<211> LENGTH: 76
<212> TYPE: RNA
<213> ORGANISM: Artificial
<220> FEATURE:
<223> OTHER INFORMATION: Aptamer 10-6, binds to DFHBI

<400> SEQUENCE: 19
ugaaugaacg ggguaaauag gcgugggucg gguccugcuu cggcaguuga gugugagagc    60
gaacucugua guuccg                                                    76

<210> SEQ ID NO 20
<211> LENGTH: 72
<212> TYPE: RNA
<213> ORGANISM: Artificial
<220> FEATURE:
<223> OTHER INFORMATION: Aptamer J2-6, binds to o-HBI
<220> FEATURE:
<221> NAME/KEY: misc_feature
<222> LOCATION: (25)..(25)
<223> OTHER INFORMATION: N is C or U

<400> SEQUENCE: 20
ugaaaauggc aaaauauucg agaancuggu cugcuucggc aggauucucc aaggggauaga    60 ucguguauuc cg                                                        72

<210> SEQ ID NO 21
<211> LENGTH: 72
<212> TYPE: RNA
<213> ORGANISM: Artificial
<220> FEATURE:
<223> OTHER INFORMATION: Aptamer J2-18, binds to o-HBI
<220> FEATURE:
<221> NAME/KEY: misc_feature
<222> LOCATION: (10)..(12)
<223> OTHER INFORMATION: N is C or U
<220> FEATURE:
<221> NAME/KEY: misc_feature
<222> LOCATION: (15)..(15)
<223> OTHER INFORMATION: N is C or U
<220> FEATURE:
<221> NAME/KEY: misc_feature
<222> LOCATION: (20)..(20)
<223> OTHER INFORMATION: N is C or U
<220> FEATURE:
<221> NAME/KEY: misc_feature
<222> LOCATION: (22)..(22)
<223> OTHER INFORMATION: N is C or U
<220> FEATURE:
```

```
<221> NAME/KEY: misc_feature
<222> LOCATION: (24)..(24)
<223> OTHER INFORMATION: N is C or U
<220> FEATURE:
<221> NAME/KEY: misc_feature
<222> LOCATION: (28)..(28)
<223> OTHER INFORMATION: N is C or U
<220> FEATURE:
<221> NAME/KEY: misc_feature
<222> LOCATION: (45)..(45)
<223> OTHER INFORMATION: N is C or U
<220> FEATURE:
<221> NAME/KEY: misc_feature
<222> LOCATION: (47)..(47)
<223> OTHER INFORMATION: N is C or U
<220> FEATURE:
<221> NAME/KEY: misc_feature
<222> LOCATION: (55)..(55)
<223> OTHER INFORMATION: N is C or U
<220> FEATURE:
<221> NAME/KEY: misc_feature
<222> LOCATION: (60)..(61)
<223> OTHER INFORMATION: N is C or U
<220> FEATURE:
<221> NAME/KEY: misc_feature
<222> LOCATION: (64)..(64)
<223> OTHER INFORMATION: N is C or U

<400> SEQUENCE: 21
ugaaaaugun nnauncgagn cngnauunag cugcuucggc agaangnucu cccanagcun    60
nugncaaauc cg                                                        72

<210> SEQ ID NO 22
<211> LENGTH: 73
<212> TYPE: RNA
<213> ORGANISM: Artificial
<220> FEATURE:
<223> OTHER INFORMATION: Aptamer S8-9, binds to o-HBI
<220> FEATURE:
<221> NAME/KEY: misc_feature
<222> LOCATION: (24)..(24)
<223> OTHER INFORMATION: N is C or U
<220> FEATURE:
<221> NAME/KEY: misc_feature
<222> LOCATION: (27)..(27)
<223> OTHER INFORMATION: N is C or U
<220> FEATURE:
<221> NAME/KEY: misc_feature
<222> LOCATION: (29)..(30)
<223> OTHER INFORMATION: N is C or U

<400> SEQUENCE: 22 ugaaaugua uagucggaug ugcnganunn acugcuucgg cagcuuagau guaugcagcu    60
gcucgggagu ccg                                                      73

<210> SEQ ID NO 23
<211> LENGTH: 72
<212> TYPE: RNA
<213> ORGANISM: Artificial
<220> FEATURE:
<223> OTHER INFORMATION: Aptamer S8-20, binds to o-HBI

<400> SEQUENCE: 23
ugaaucuccg ugucagggca gagcagggcg cugcuucggc agauaaugua uagucgggau    60
cgcugaacuc cg                                                        72

<210> SEQ ID NO 24
<211> LENGTH: 72
<212> TYPE: RNA
<213> ORGANISM: Artificial
```

```
<220> FEATURE:
<223> OTHER INFORMATION: Aptamer N19-4, binds to DMABI
<220> FEATURE:
<221> NAME/KEY: misc_feature
<222> LOCATION: (23)..(23)
<223> OTHER INFORMATION: N is C or U

<400> SEQUENCE: 24
ugaacgaaua ggugggagguu gcncuguuuu cugcuucggc agguuaaaga uugguacuca      60 ucacggxguc cg                                                           72

<210> SEQ ID NO 25
<211> LENGTH: 72
<212> TYPE: RNA
<213> ORGANISM: Artificial
<220> FEATURE:
<223> OTHER INFORMATION: Aptamer N19-10, binds to DMABI

<400> SEQUENCE: 25
ugaacaguuu cgugcaguuu gaaauguagg cugcuucggc aggauaggug uggaggugga      60
uguccggguc cg                                                           72

<210> SEQ ID NO 26
<211> LENGTH: 73
<212> TYPE: RNA
<213> ORGANISM: Artificial
<220> FEATURE:
<223> OTHER INFORMATION: Aptamer N9-1, binds to DMABI
<220> FEATURE:
<221> NAME/KEY: misc_feature
<222> LOCATION: (28)..(28)
<223> OTHER INFORMATION: n is a, c, g, or u

<400> SEQUENCE: 26
ugaacccuga aaagagggaa ggccuggnuu gcugcuucgg caggggauug aucagggugc      60
acguugcugu ccg                                                          73

<210> SEQ ID NO 27
<211> LENGTH: 72
<212> TYPE: RNA
<213> ORGANISM: Artificial
<220> FEATURE:
<223> OTHER INFORMATION: Aptamer N9-6, binds to DMABI

<400> SEQUENCE: 27
ugaagccuug aaauaguagu gaucgagugg cugcuucggc agacucugag uuggcuaua      60 cgugaucguc cg                                                           72

<210> SEQ ID NO 28
<211> LENGTH: 72
<212> TYPE: RNA
<213> ORGANISM: Artificial
<220> FEATURE:
<223> OTHER INFORMATION: Aptamer N11-3, binds to DMABI
<220> FEATURE:
<221> NAME/KEY: misc_feature
<222> LOCATION: (17)..(17)
<223> OTHER INFORMATION: N is C or U
<220> FEATURE:
<221> NAME/KEY: misc_feature
<222> LOCATION: (24)..(24)
<223> OTHER INFORMATION: N is C or U
<220> FEATURE:
<221> NAME/KEY: misc_feature
<222> LOCATION: (26)..(26)
<223> OTHER INFORMATION: N is C or U
<220> FEATURE:
```

```
<221> NAME/KEY: misc_feature
<222> LOCATION: (30)..(30)
<223> OTHER INFORMATION: N is C or U
<220> FEATURE:
<221> NAME/KEY: misc_feature
<222> LOCATION: (56)..(57)
<223> OTHER INFORMATION: N is C or U
<220> FEATURE:
<221> NAME/KEY: misc_feature
<222> LOCATION: (60)..(60)
<223> OTHER INFORMATION: N is C or U
<220> FEATURE:
<221> NAME/KEY: misc_feature
<222> LOCATION: (66)..(66)
<223> OTHER INFORMATION: N is C or U

<400> SEQUENCE: 28
ugaaaaagug guauuunaaa uucnanuuan cugcuucggc agacgacggg ggggcnngun    60
uuggangauc cg                                                      72

<210> SEQ ID NO 29
<211> LENGTH: 75
<212> TYPE: RNA
<213> ORGANISM: Artificial
<220> FEATURE:
<223> OTHER INFORMATION: Aptamer N15-1, binds to DMABI
<220> FEATURE:
<221> NAME/KEY: misc_feature
<222> LOCATION: (8)..(8)
<223> OTHER INFORMATION: N is C or U
<220> FEATURE:
<221> NAME/KEY: misc_feature
<222> LOCATION: (19)..(19)
<223> OTHER INFORMATION: N is C or U
<220> FEATURE:
<221> NAME/KEY: misc_feature
<222> LOCATION: (23)..(23)
<223> OTHER INFORMATION: N is C or U
<220> FEATURE:
<221> NAME/KEY: misc_feature
<222> LOCATION: (27)..(27)
<223> OTHER INFORMATION: N is C or U
<220> FEATURE:
<221> NAME/KEY: misc_feature
<222> LOCATION: (62)..(62)
<223> OTHER INFORMATION: N is C or U
<220> FEATURE:
<221> NAME/KEY: misc_feature
<222> LOCATION: (69)..(69)
<223> OTHER INFORMATION: N is C or U

<400> SEQUENCE: 29
ugaaugungc auaauugang gangauncau gcugcuucgg caguugggug uaaaaaugga    60
angaggucnu auccg                                                   75

<210> SEQ ID NO 30
<211> LENGTH: 72
<212> TYPE: RNA
<213> ORGANISM: Artificial
<220> FEATURE:
<223> OTHER INFORMATION: Aptamer N8-4, binds to DMABI
<220> FEATURE:
<221> NAME/KEY: misc_feature
<222> LOCATION: (23)..(24)
<223> OTHER INFORMATION: N is C or U

<400> SEQUENCE: 30
ugaauccagg gguggucggu ggnnggagcg cugcuucggc agugagcugg ggaguucagu    60
caaugugguc cg                                                      72
```

```
<210> SEQ ID NO 31
<211> LENGTH: 163
<212> TYPE: RNA
<213> ORGANISM: Artificial
<220> FEATURE:
<223> OTHER INFORMATION: bivalent ATP sensor, binds to DMHBI

<400> SEQUENCE: 31
gggagacgca acugaaugaa ccuguagaac gacuuggucg ggucagugug uggggagauc      60
uacggaucuc agggcuguua cgggagcuac auggaaggag uccaugugac guaugcuucg     120
agaauagagu guggggucgu auccgcguaa cuagucgcgu cac                      163

<210> SEQ ID NO 32
<211> LENGTH: 118
<212> TYPE: RNA
<213> ORGANISM: Artificial
<220> FEATURE:
<223> OTHER INFORMATION: bivalent adenosine sensor, binds to DMHBI

<400> SEQUENCE: 32
cgcaacugaa ugaaccugua gaacgacuug gucgggucag cugcggaaga aacuguggca      60
cuucggugcc agguagcuuc gagaauagag uguggggucg uauccguaac caguugcg      118

<210> SEQ ID NO 33
<211> LENGTH: 126
<212> TYPE: RNA
<213> ORGANISM: Artificial
<220> FEATURE:
<223> OTHER INFORMATION: bivalent cGMP sensor, binds to DMHBI

<400> SEQUENCE: 33
gggagacgca acugaaugaa ccuguagaac gacuuggucg ggucagcccu gcgaugcaga      60
aaggugcuga cgacacaucu ucgagaauag aguguggggu cguauccgcg uaacuagucg     120
cgucac                                                               126

<210> SEQ ID NO 34
<211> LENGTH: 114
<212> TYPE: DNA
<213> ORGANISM: Artificial
<220> FEATURE:
<223> OTHER INFORMATION: clone 3-6

<400> SEQUENCE: 34
gggagatacg ctctagaatt caattgcatg gtggtctggg acagacgtgt ggacggcaca      60
cagcgtgagg ctttggtggg ttatggctgt catgcgagat agctcgagca atgc           114

<210> SEQ ID NO 35
<211> LENGTH: 113
<212> TYPE: DNA
<213> ORGANISM: Artificial
<220> FEATURE:
<223> OTHER INFORMATION: clone 13-2

<400> SEQUENCE: 35
gggagatacg ctctagaatt caatttgcgt attgagacag gccgcgcta tttctggagg       60 ggcgctacat gaaagtggtg gttgggtgcg gtcggagata gctcgagcaa tgc            113

<210> SEQ ID NO 36
<211> LENGTH: 60
<212> TYPE: DNA
<213> ORGANISM: Artificial
<220> FEATURE:
```

<223> OTHER INFORMATION: 13-2-min coding sequence

<400> SEQUENCE: 36
gggctatttc tggaggggcg ctacatgaaa gtggtggttg ggtgcggtcg agatagctc    60

<210> SEQ ID NO 37
<211> LENGTH: 109
<212> TYPE: DNA
<213> ORGANISM: Artificial
<220> FEATURE:
<223> OTHER INFORMATION: clone 13-2-1

<400> SEQUENCE: 37
gggtatccgg aatcttatac attgttatgt ctggaggggc gccgcatgaa cgcggtggtg    60
aggtgcggtc ggatataact ggtggagtgc aagagtctga gcacactgg              109

<210> SEQ ID NO 38
<211> LENGTH: 109
<212> TYPE: DNA
<213> ORGANISM: Artificial
<220> FEATURE:
<223> OTHER INFORMATION: clone 13-2-3

<400> SEQUENCE: 38
gggtatccgg aatcttatac attgctatttct ctggaggggc gccccatgaa aggggtggtt    60
gagagcggtc ggagatagcg gaaacagtgc aagagtctga gcacactgg              109

<210> SEQ ID NO 39
<211> LENGTH: 109
<212> TYPE: DNA
<213> ORGANISM: Artificial
<220> FEATURE:
<223> OTHER INFORMATION: clone 13-2-4

<400> SEQUENCE: 39
gggtatccgg aatcttatac attgctattg ttggaggggc gctacgtgaa agtggtggta    60
cggtgcggtc ggcaatagct cgtatagtgc aagagtctga gcacactgg              109

<210> SEQ ID NO 40
<211> LENGTH: 109
<212> TYPE: DNA
<213> ORGANISM: Artificial
<220> FEATURE:
<223> OTHER INFORMATION: clone 13-2-5

<400> SEQUENCE: 40
gggtatccgg aatcttatac attgctctgt ttggaggggc gctactttca agtagtggtt    60
gagtgcggtc gaacagagct tgggcgttgc aagagtctga gcacactgg              109

<210> SEQ ID NO 41
<211> LENGTH: 57
<212> TYPE: DNA
<213> ORGANISM: Artificial
<220> FEATURE:
<223> OTHER INFORMATION: 13-2 variable region consensus
<220> FEATURE:
<221> NAME/KEY: misc_feature
<222> LOCATION: (50)..(50)
<223> OTHER INFORMATION: N is A, C, T, or G
<220> FEATURE:
<221> NAME/KEY: misc_feature
<222> LOCATION: (57)..(57)
<223> OTHER INFORMATION: N is A, C, T, or G

<400> SEQUENCE: 41

```
ctatttctgg aggggcgcta catgaaagtg gtggttgggt gcggtcggan atagctn        57
```

\<210\> SEQ ID NO 42
\<211\> LENGTH: 108
\<212\> TYPE: DNA
\<213\> ORGANISM: Artificial
\<220\> FEATURE:
\<223\> OTHER INFORMATION: Clone 10-6

\<400\> SEQUENCE: 42

```
gggagacgca actgaatgaa tgaacggggt aaataggcgt gggtcgggtc ctgcttcggc     60
agttgagtgt gagagcgaac tctgtagttc cgtaactagt cgcgtcac                108
```

\<210\> SEQ ID NO 43
\<211\> LENGTH: 106
\<212\> TYPE: DNA
\<213\> ORGANISM: Artificial
\<220\> FEATURE:
\<223\> OTHER INFORMATION: Clone 24-1

\<400\> SEQUENCE: 43

```
gggagacgca actgaatgaa cctgtagaac gacttggtcg ggtcagctgc ttcggcagct     60
tcgagaatag agtgtggggt cgtatccgcg taactagtcg cgtcac                   106
```

\<210\> SEQ ID NO 44
\<211\> LENGTH: 106
\<212\> TYPE: DNA
\<213\> ORGANISM: Artificial
\<220\> FEATURE:
\<223\> OTHER INFORMATION: Clone 24-2

\<400\> SEQUENCE: 44

```
gggagacgca actgaatgaa atggtgaagg acgggtccag gtgtggctgc ttcggcagtg     60
cagcttgttg agtagagtgt gagctccgcg taactagtcg cgtcac                   106
```

\<210\> SEQ ID NO 45
\<211\> LENGTH: 104
\<212\> TYPE: DNA
\<213\> ORGANISM: Artificial
\<220\> FEATURE:
\<223\> OTHER INFORMATION: Clone 19-4
\<220\> FEATURE:
\<221\> NAME/KEY: misc_feature
\<222\> LOCATION: (39)..(39)
\<223\> OTHER INFORMATION: N is C or T

\<400\> SEQUENCE: 45

```
gggagacgca actgaatgaa cgaataggtg gaggttgcnc tgttttctgc ttcggcaggt     60
taaagattgg tactcatcac ggtgtccgta actagtcgcg tcac                     104
```

\<210\> SEQ ID NO 46
\<211\> LENGTH: 104
\<212\> TYPE: DNA
\<213\> ORGANISM: Artificial
\<220\> FEATURE:
\<223\> OTHER INFORMATION: Clone 19-10

\<400\> SEQUENCE: 46

```
gggagacgca actgaatgaa cagtttcgtg cagtttgaaa tgtaggctgc ttcggcagga     60
taggtgtgga ggtggatgtc cgggtccgta actagtcgcg tcac                     104
```

\<210\> SEQ ID NO 47

```
<211> LENGTH: 105
<212> TYPE: DNA
<213> ORGANISM: Artificial
<220> FEATURE:
<223> OTHER INFORMATION: Clone 9-1
<220> FEATURE:
<221> NAME/KEY: misc_feature
<222> LOCATION: (44)..(44)
<223> OTHER INFORMATION: N is C or T

<400> SEQUENCE: 47
gggagacgca actgaatgaa ccctgaaaag agggaaggcc tggnttgctg cttcggcagg      60
ggattgatca gggtgcacgt tgctgtccgt aactagtcgc gtcac                     105

<210> SEQ ID NO 48
<211> LENGTH: 104
<212> TYPE: DNA
<213> ORGANISM: Artificial
<220> FEATURE:
<223> OTHER INFORMATION: Clone 9-6

<400> SEQUENCE: 48
gggagacgca actgaatgaa gccttgaaat agtagtgatc gagtggctgc ttcggcagac      60
tctgagtgtg gctatacgtg atcgtccgta actagtcgcg tcac                      104

<210> SEQ ID NO 49
<211> LENGTH: 104
<212> TYPE: DNA
<213> ORGANISM: Artificial
<220> FEATURE:
<223> OTHER INFORMATION: Clone 11-3
<220> FEATURE:
<221> NAME/KEY: misc_feature
<222> LOCATION: (33)..(33)
<223> OTHER INFORMATION: N is C or T
<220> FEATURE:
<221> NAME/KEY: misc_feature
<222> LOCATION: (40)..(40)
<223> OTHER INFORMATION: N is C or T
<220> FEATURE:
<221> NAME/KEY: misc_feature
<222> LOCATION: (42)..(42)
<223> OTHER INFORMATION: N is C or T
<220> FEATURE:
<221> NAME/KEY: misc_feature
<222> LOCATION: (46)..(46)
<223> OTHER INFORMATION: N is C or T
<220> FEATURE:
<221> NAME/KEY: misc_feature
<222> LOCATION: (72)..(73)
<223> OTHER INFORMATION: N is C or T
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: N is C or T

<400> SEQUENCE: 49
gggagacgca actgaatgaa aaagtggtat ttnaaattcn anttanctgc ttcggcagac      60 gacgggggg cnngtnttgg angatccgta actagtcgcg tcac                       104

<210> SEQ ID NO 50
<211> LENGTH: 107
<212> TYPE: DNA
<213> ORGANISM: Artificial
<220> FEATURE:
<223> OTHER INFORMATION: Clone 15-1
```

<220> FEATURE:
<221> NAME/KEY: misc_feature
<222> LOCATION: (24)..(24)
<223> OTHER INFORMATION: N is C or T
<220> FEATURE:
<221> NAME/KEY: misc_feature
<222> LOCATION: (35)..(35)
<223> OTHER INFORMATION: N is C or T
<220> FEATURE:
<221> NAME/KEY: misc_feature
<222> LOCATION: (39)..(39)
<223> OTHER INFORMATION: N is C or T
<220> FEATURE:
<221> NAME/KEY: misc_feature
<222> LOCATION: (43)..(43)
<223> OTHER INFORMATION: N is C or T
<220> FEATURE:
<221> NAME/KEY: misc_feature
<222> LOCATION: (78)..(78)
<223> OTHER INFORMATION: N is C or T
<220> FEATURE:
<221> NAME/KEY: misc_feature
<222> LOCATION: (85)..(85)
<223> OTHER INFORMATION: N is C or T

<400> SEQUENCE: 50
gggagacgca actgaatgaa tgtngcataa ttganggang atncatgctg cttcggcagt    60
tgggtgtaaa aatggaanga ggtcntatcc gtaactagtc gcgtcac                 107

<210> SEQ ID NO 51
<211> LENGTH: 104
<212> TYPE: DNA
<213> ORGANISM: Artificial
<220> FEATURE:
<223> OTHER INFORMATION: Clone 8-4
<220> FEATURE:
<221> NAME/KEY: misc_feature
<222> LOCATION: (39)..(40)
<223> OTHER INFORMATION: N is C or T

<400> SEQUENCE: 51
gggagacgca actgaatgaa tccaggggtg gtcggtggnn ggagcgctgc ttcggcagtg    60
agctggggag ttcagtcaat gtggtccgta actagtcgcg tcac                    104

<210> SEQ ID NO 52
<211> LENGTH: 104
<212> TYPE: DNA
<213> ORGANISM: Artificial
<220> FEATURE:
<223> OTHER INFORMATION: Clone 2-6
<220> FEATURE:
<221> NAME/KEY: misc_feature
<222> LOCATION: (41)..(41)
<223> OTHER INFORMATION: N is C or T

<400> SEQUENCE: 52
gggagacgca actgaatgaa aatggcaaaa tattcgagaa nctggtctgc ttcggcagga    60
ttctccaagg ggtagatcgt gtattccgta actagtcgcg tcac                    104

<210> SEQ ID NO 53
<211> LENGTH: 104
<212> TYPE: DNA
<213> ORGANISM: Artificial
<220> FEATURE:
<223> OTHER INFORMATION: Clone 2-18
<220> FEATURE:
<221> NAME/KEY: misc_feature
<222> LOCATION: (26)..(28)
<223> OTHER INFORMATION: N is C or T
<220> FEATURE:

<221> NAME/KEY: misc_feature
<222> LOCATION: (31)..(31)
<223> OTHER INFORMATION: N is C or T
<220> FEATURE:
<221> NAME/KEY: misc_feature
<222> LOCATION: (36)..(36)
<223> OTHER INFORMATION: N is C or T
<220> FEATURE:
<221> NAME/KEY: misc_feature
<222> LOCATION: (38)..(38)
<223> OTHER INFORMATION: N is C or T
<220> FEATURE:
<221> NAME/KEY: misc_feature
<222> LOCATION: (40)..(40)
<223> OTHER INFORMATION: N is C or T
<220> FEATURE:
<221> NAME/KEY: misc_feature
<222> LOCATION: (44)..(44)
<223> OTHER INFORMATION: N is C or T
<220> FEATURE:
<221> NAME/KEY: misc_feature
<222> LOCATION: (61)..(61)
<223> OTHER INFORMATION: N is C or T
<220> FEATURE:
<221> NAME/KEY: misc_feature
<222> LOCATION: (63)..(63)
<223> OTHER INFORMATION: N is C or T
<220> FEATURE:
<221> NAME/KEY: misc_feature
<222> LOCATION: (71)..(71)
<223> OTHER INFORMATION: N is C or T
<220> FEATURE:
<221> NAME/KEY: misc_feature
<222> LOCATION: (76)..(77)
<223> OTHER INFORMATION: N is C or T
<220> FEATURE:
<221> NAME/KEY: misc_feature
<222> LOCATION: (80)..(80)
<223> OTHER INFORMATION: N is C or T

<400> SEQUENCE: 53
gggagacgca actgaatgaa aatgtnnnat ncgagncngn attnagctgc ttcggcagaa      60
ngntctccca nagctnntgn caaatccgta actagtcgcg tcac                      104

<210> SEQ ID NO 54
<211> LENGTH: 105
<212> TYPE: DNA
<213> ORGANISM: Artificial
<220> FEATURE:
<223> OTHER INFORMATION: Clone 8-9
<220> FEATURE:
<221> NAME/KEY: misc_feature
<222> LOCATION: (40)..(40)
<223> OTHER INFORMATION: N is C or T
<220> FEATURE:
<221> NAME/KEY: misc_feature
<222> LOCATION: (43)..(43)
<223> OTHER INFORMATION: N is C or T
<220> FEATURE:
<221> NAME/KEY: misc_feature
<222> LOCATION: (45)..(46)
<223> OTHER INFORMATION: N is C or T

<400> SEQUENCE: 54
gggagacgca actgaatgaa aatgtatagt cggatgtgcn gantnnactg cttcggcagc      60
ttagatgtat gcagctgctc gggagtccgt aactagtcgc gtcac                     105

<210> SEQ ID NO 55
<211> LENGTH: 104
<212> TYPE: DNA
<213> ORGANISM: Artificial
<220> FEATURE:
<223> OTHER INFORMATION: Clone 8-20

<400> SEQUENCE: 55
gggagacgca actgaatgaa tctccgtgtc agggcagagc agggcgctgc ttcggcagat    60
aatgtatagt cgggatcgct gaactccgta actagtcgcg tcac                   104

<210> SEQ ID NO 56
<211> LENGTH: 94
<212> TYPE: RNA
<213> ORGANISM: Artificial
<220> FEATURE:
<223> OTHER INFORMATION: 24-1 derived aptamer, sensor scaffold

<400> SEQUENCE: 56
cgcaacugaa ugaaccugua gaacgacuug gucgggucag cugcuucggc agcuucgaga    60
auagagugug gggucguauc cguaaccagu ugcg                              94

<210> SEQ ID NO 57
<211> LENGTH: 104
<212> TYPE: DNA
<213> ORGANISM: Artificial
<220> FEATURE:
<223> OTHER INFORMATION: Clone 23-11

<400> SEQUENCE: 57
gggagacgca actgaatgaa atgacagtac agtggagggt gcggtactgc ttcggcaggg    60
aaggggcgct gttcttgtct catatccgta actagtcgcg tcac                   104

<210> SEQ ID NO 58
<211> LENGTH: 104
<212> TYPE: DNA
<213> ORGANISM: Artificial
<220> FEATURE:
<223> OTHER INFORMATION: Clone 17-3
<220> FEATURE:
<221> NAME/KEY: misc_feature
<222> LOCATION: (44)..(44)
<223> OTHER INFORMATION: N is C or T

<400> SEQUENCE: 58
gggagacgca actgaatgaa gagcagtagc gagtagttca caanagctgc ttcggcagga    60
tcttgtagga agtaaatgtg caaatccgta actagtcgcg tcac                   104

<210> SEQ ID NO 59
<211> LENGTH: 104
<212> TYPE: DNA
<213> ORGANISM: Artificial
<220> FEATURE:
<223> OTHER INFORMATION: Clone 2-4

<400> SEQUENCE: 59
gggagacgca actgaatgaa acctagagtt atgccaggct ctgagcctgc ttcggcaggt    60
gctatgatcg ccagcggtat gcagtccgta actagtcgcg tcac                   104

<210> SEQ ID NO 60
<211> LENGTH: 105
<212> TYPE: DNA
<213> ORGANISM: Artificial
<220> FEATURE:
<223> OTHER INFORMATION: Clone 17-17
<220> FEATURE:
<221> NAME/KEY: misc_feature
<222> LOCATION: (22)..(23)
<223> OTHER INFORMATION: N is C or T
<220> FEATURE:

<221> NAME/KEY: misc_feature
<222> LOCATION: (38)..(38)
<223> OTHER INFORMATION: N is C or T
<220> FEATURE:
<221> NAME/KEY: misc_feature
<222> LOCATION: (42)..(43)
<223> OTHER INFORMATION: N is C or T
<220> FEATURE:
<221> NAME/KEY: misc_feature
<222> LOCATION: (61)..(61)
<223> OTHER INFORMATION: N is C or T
<220> FEATURE:
<221> NAME/KEY: misc_feature
<222> LOCATION: (73)..(73)
<223> OTHER INFORMATION: N is C or T
<220> FEATURE:
<221> NAME/KEY: misc_feature
<222> LOCATION: (77)..(77)
<223> OTHER INFORMATION: N is C or T
<220> FEATURE:
<221> NAME/KEY: misc_feature
<222> LOCATION: (80)..(80)
<223> OTHER INFORMATION: N is C or T
<220> FEATURE:
<221> NAME/KEY: misc_feature
<222> LOCATION: (83)..(83)
<223> OTHER INFORMATION: N is C or T

<400> SEQUENCE: 60
gggagacgca actgaatgaa annaaatatt cgggatanat annattactg cttcggcaga      60
nagcggttaa ttnttgnaan tcnaatcccg aactagtcgc gtcac                     105

<210> SEQ ID NO 61
<211> LENGTH: 105
<212> TYPE: DNA
<213> ORGANISM: Artificial
<220> FEATURE:
<223> OTHER INFORMATION: Clone 18-16
<220> FEATURE:
<221> NAME/KEY: misc_feature
<222> LOCATION: (21)..(21)
<223> OTHER INFORMATION: N is C or T
<220> FEATURE:
<221> NAME/KEY: misc_feature
<222> LOCATION: (35)..(35)
<223> OTHER INFORMATION: N is C or T
<220> FEATURE:
<221> NAME/KEY: misc_feature
<222> LOCATION: (45)..(45)
<223> OTHER INFORMATION: N is C or T
<220> FEATURE:
<221> NAME/KEY: misc_feature
<222> LOCATION: (69)..(69)
<223> OTHER INFORMATION: N is C or T
<220> FEATURE:
<221> NAME/KEY: misc_feature
<222> LOCATION: (83)..(83)
<223> OTHER INFORMATION: N is C or T
<220> FEATURE:
<221> NAME/KEY: misc_feature
<222> LOCATION: (85)..(85)
<223> OTHER INFORMATION: N is C or T
<220> FEATURE:
<221> NAME/KEY: misc_feature
<222> LOCATION: (88)..(88)
<223> OTHER INFORMATION: N is C or T

<400> SEQUENCE: 61
gggagacgca actgaatgaa nggactcgtc tggcnggatg ggcgntggt actgctttcg       60 ggcaggatng ggtataacgg tanangcnct aactagtcgc gtcac                     105

<210> SEQ ID NO 62
<211> LENGTH: 98

```
<212> TYPE: RNA
<213> ORGANISM: Artificial
<220> FEATURE:
<223> OTHER INFORMATION: Bivalent ATP sensor, binds DMHBI

<400> SEQUENCE: 62
cuauuucugg aggggcgcua cuguguggga agaaacugug gcacuucggu gccagcguau      60
gggugguugg gugcggucgg agauagcucg agcaaugc                              98
```